United States Patent [19]

Di Malta et al.

[11] Patent Number: 5,585,394
[45] Date of Patent: Dec. 17, 1996

[54] 1-BENZENESULFONYL-1,3-DIHYDRO-2H-BENZIMIDAZOL-2-ONE DERIVATIVES

[75] Inventors: Alain Di Malta, Saint Clement de Riviere; Georges Garcia, Saint Gely du Fesc; Daniel Mettefeu, Grabels; Dino Nisato, Saint Georges d'Orques; Richard Roux, Vailhauques; Claudine Serradeil-Legal, Escalquens, all of France

[73] Assignee: Sanofi, Paris, France

[21] Appl. No.: 282,547

[22] Filed: Jul. 29, 1994

[30] Foreign Application Priority Data

Jul. 30, 1993 [FR] France ................... 93 09403

[51] Int. Cl.$^6$ ............ A16K 31/415; C07D 235/26; C07D 235/22; C07D 403/02
[52] U.S. Cl. ............ 514/387; 514/210; 514/212; 514/228.2; 514/253; 514/254; 514/256; 514/234.5; 514/322; 514/359; 514/381; 514/383; 514/338; 544/62; 544/139; 544/238; 544/242; 544/336; 544/370; 546/199; 546/273.7; 548/250; 548/255; 548/262.2
[58] Field of Search ............ 548/306.4, 306.7, 548/304.7, 306.1; 514/387, 322, 234.5, 338, 254; 546/199, 273.7; 544/139, 370

[56] References Cited

U.S. PATENT DOCUMENTS

| | | | |
|---|---|---|---|
| 3,405,136 | 10/1968 | Wright | 260/309.2 |
| 3,849,431 | 11/1974 | Gallay et al. | 260/306.6 |
| 4,205,077 | 5/1980 | Aufderhaar et al. | 424/273 |
| 4,916,149 | 4/1990 | Palosi et al. | 514/387 |
| 5,338,755 | 8/1994 | Wagnon et al. | 514/414 |

FOREIGN PATENT DOCUMENTS

| | | |
|---|---|---|
| 0324988 | 7/1989 | European Pat. Off. . |
| 0470514 | 2/1992 | European Pat. Off. . |
| 0526348 | 2/1993 | European Pat. Off. . |
| WO93/15051 | 8/1993 | WIPO ............ C07D 209/96 |

OTHER PUBLICATIONS

Achour, Reddouane; Zniber, Rachid Bull. Soc. Chim. Belg. (1987), 96(10), 787–92.

Primary Examiner—Joseph McKane
Assistant Examiner—Laura L. Stockton
Attorney, Agent, or Firm—Bacon & Thomas

[57] ABSTRACT

The present invention relates to 1-benzenesulfonyl-1,3-dihydro-2H-benzimidazol-2-one derivatives of the formula:

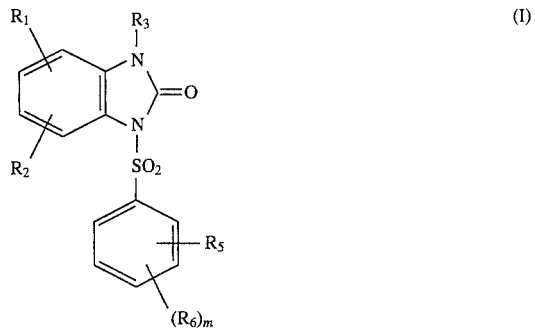

to their preparation and to the pharmaceutical compositions in which they are present. These derivatives have an affinity for the vasopressin and oxytocin receptors.

14 Claims, No Drawings

1-BENZENESULFONYL-1,3-DIHYDRO-2H-BENZIMIDAZOL-2-ONE DERIVATIVES

The present invention relates to 1-benzenesulfonyl-1,3-dihydro-2H-benzimidazol-2-one derivatives, to their preparation and to the pharmaceutical compositions in which they are present.

Several patent applications have recently described families of compounds of non-peptide structure which are active on the vasopressin and/or oxytocin receptors. The following may be mentioned: European patent applications EP 382 185, EP 444 945, EP 514 667, EP 469 984 and EP 526 348, patent applications WO 91/05 549 and WO 93/15 051 and Japanese patent applications JP-04/321 669 and 03/127 732.

The 1-benzenesulfonyl-1,3-dihydro-2H-benzimidazol-2-one derivatives according to the present invention have an affinity for the vasopressin and oxytocin receptors.

Vasopressin is a hormone known for its antidiuretic effect and its effect in the regulation of arterial pressure. It stimulates several types of receptors, namely $V_1$ ($V_{1a}$, $V_{1b}$) and $V_2$. These receptors are localized in the liver, vessels (coronary, renal, cerebral), platelets, kidney, uterus, suprarenal glands, central nervous system and pituitary gland. Oxytocin has a peptide structure similar to that of vasopressin. The oxytocin receptors are also found on the smooth muscle of the uterus, as well as on myoepithelial cells of the mammary gland, in the central nervous system and in the kidney. The localization of the different receptors is described in: S. JARS et al., Vasopressin and oxytocin receptors: an overview, in Progress in Endocrinology; H. IMURA and K. SHIZURNE ed., Experta Medica, Amsterdam, 1988, 1183–1188, and in the following articles: Presse Médicale, 1987, 16 (10), 481–485; J. Lab. Clin. Med., 1989, 114 (6), 617–632; and Pharmacol. Rev., 1991, 43 (1), 73–108. Vasopressin thus exerts cardiovascular, hepatic, antidiuretic and aggregating effects and effects on the central and peripheral nervous system. Oxytocin is involved in parturition, lactation and sexual behavior.

The compounds according to the present invention make it possible selectively either to mimic the effects of the hormone (in the case of anatgonists) or to inhibit them (in the case of antagonists). Vasopressin receptor antagonists can affect the regulation of the central and peripheral circulation, especially the coronary, renal and gastric circulation, as well as the regulation of hydration and the release of adrenocorticotrophic hormone (ACTH). Vasopressin antagonists can advantageously replace vasopressin or its analogs in the treatment of diabetes insipidus; they can also be used in the treatment of enuresis and in the regulation of hemostasis: treatment of hemophilia and von Willebrand's syndrome, antidote to platelet aggregating agents, F. A. LASZLO, Pharmacol. Rev., 1991, 43, 73–108; and Drug Investigation, 1990, 2 (Suppl. 5), 1–47. The hormones themselves, namely vasopressin and oxytocin, and some of their peptide or non-peptide analogs are used in therapeutics and have been found to be effective. Several reviews and numerous literature articles may be mentioned: Vasopressin, P. GROSS et al. ed., John Libbey Eurotext, 1993, in particular 243–257 and 549–562; F. A. LASZLO and F. A. LASZLO Jr., Clinical perspectives for vasopressin antagonists, Drug News Perspect., 1993, 6 (8); W. G. NORTH, J. Clin. Endocrinol., 1991, 73, 1316–1320; J. J. LEGROS et al., Prog. Neuro-Pharmacol. Biol. Psychiat., 1988, 12, 571–586; K. E. ANDERSSON et al., Drugs Today, 1988, 24 (7), 509–528; D. L. STUMP et al., Drugs, 1990, 39, 38–53; S. CALTABIANO et al., Drugs Future, 1988, 13, 25–30; Y. MURA et al., Clin. Nephrol., 1993, 40, 60–61; and Faseb J., 1994, 8 (5), A587: 3398.

Thus the compounds according to the invention are useful especially in the treatment of complaints of the central and peripheral nervous system, the cardiovascular system, the renal domain and the gastric domain and in disorders of sexual behavior, in man and animals.

According to one of its features, the present invention relates to compounds of the formula

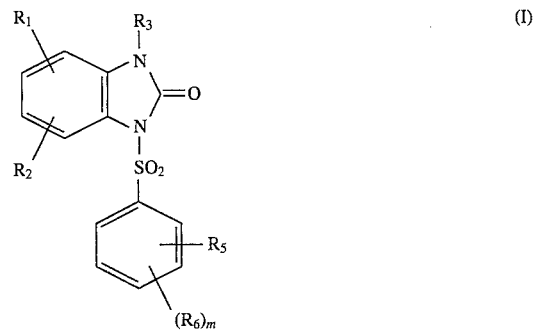

in which:

$R_1$ and $R_2$ are each independently a hydrogen; a halogen; a hydroxyl; an ω-halogeno($C_1$–$C_7$)alkoxy; a ($C_1$–$C_7$)alkyl; a trifluoromethyl; a ($C_1$–$C_7$)alkoxy; a polyhalogeno($C_1$–$C_7$)alkoxy; an ω-hydroxy($C_2$–$C_7$)alkoxy; an ω-methoxy($C_2$–$C_7$)alkoxy; an ω-amino($C_2$–$C_7$)alkoxy in which the amino is free or substituted by one or two ($C_1$–$C_7$)alkyls; a ($C_3$–$C_7$)cycloalkoxy; a ($C_3$–$C_7$)cycloalkylmethoxy; a phenoxy; a benzyloxy; a ($C_1$–$C_7$)alkylthio; a phenylthio; a nitro; an amino which is free or substituted by one or two ($C_1$–$C_7$)alkyls; a cyano; a ($C_1$–$C_7$)alkylcarbonyl; a formyl; a benzoyl; a formyloxy; a ($C_1$–$C_7$)alkylcarbonyloxy; a benzoyloxy; a ($C_1$–$C_7$)alkylsulfonamido; a phenylsulfonamido; a benzylsulfonamido; a ($C_1$–$C_7$)alkylcarbonylamino; a ($C_1$–$C_7$)alkoxycarbonylamino; a ureido which is unsubstituted or substituted by a phenyl, a benzyl or one or two ($C_1$–$C_7$)alkyls; or a thioureido which is unsubstituted or substituted by a phenyl, a benzyl or one or two ($C_1$–$C_7$)alkyls;

$R_3$ is $R_4$; a ($C_1$–$C_8$)alkyl; a ($C_1$–$C_8$)alkylene substituted by $R_4$; a ($C_1$–$C_8$)alkylene substituted by a ($C_1$–$C_4$)alkoxy; an indanyl; a hexahydroindanyl; an adamantyl; a noradamantyl; a norbornyl; or a cyclohexyl substituted by a di($C_1$–$C_7$)alkylamino, a carboxyl, a ($C_1$–$C_4$)alkoxycarbonyl, a hydroxyl, a tetrahydropyran-2-yloxy, a ($C_1$–$C_4$)alkoxy($C_1$–$C_4$)alkoxy or a phenyl($C_1$–$C_2$)alkoxy($C_1$–$C_4$)alkoxy;

$R_4$ is a group —$NR_{16}R_{17}$; a ($C_3$–$C_7$)cycloalkyl which is unsubstituted or monosubstituted or disubstituted by a ($C_1$–$C_4$)alkyl or a ($C_1$–$C_4$)alkoxy; a group Ar; a furyl; a thienyl; a pyrrolyl; a triazolyl; a tetrazolyl; a pyridyl; a pyridyl N-oxide; a pyrimidinyl; a pyrazolyl; a pyrazinyl; a tetrahydropyran-4-yl; an azetidin-3-yl substituted in the 1-position by $R_{18}$; a piperid-4-yl substituted in the 1-position by $R_{18}$ or disubstituted in the 1-position by one or two ($C_1$–$C_7$)alkyls and/or one or two benzyls; a pyrrolidinyl; a perhydroazepinyl; or a morpholinyl;

$R_5$ and $R_6$ are each independently a hydrogen; a halogen; a ($C_1$–$C_7$)alkyl; a trifluoromethyl; a cyano; a nitro; a hydroxylamino; a carboxyl; a guanidino which is unsubstituted or substituted in the 1-position by a ($C_1$–$C_7$)alkyl and/or in the 3-position by one or two ($C_1$–$C_7$)alkyls, a phenyl or a benzyl and/or in the 2-position by a cyano; a group —$OR_7$; a group —$SR_7$; a $(C_1-C_7)$alkylcarbonyl; a formyl; a benzoyl; a $(C_1-C_7)$alkoxycarbonyl; a phenoxycarbonyl; a benzyloxycarbonyl; a group —$CONR_{19}R_{20}$; a group —$CSNR_{11}R_{27}$; a group —$SO_2$—$NR_{21}R_{22}$; a $(C_1-C_7)$alkylsulfonamido; a benzylsulfonamido; a group —$NHSO_2$—Ar; a group —$NR_8R_9$; a group —CO—NH—$CR_{10}R_{23}$—CO—$R_{12}$; or a group —$CH_2NR_8R_9$;

$R_7$ is a hydrogen; a $(C_1-C_7)$alkyl; a phenyl; a benzyl; a $(C_3-C_7)$cycloalkyl; a $(C_2-C_7)$alkenyl; an ω-halogen$(C_2-C_7)$alkyl; a polyhalogeno$(C_1-C_7)$alkyl; an ω-hydroxy$(C_2-C_7)$alkyl; a $(C_1-C_7)$alkylcarbonyl; a formyl; a benzoyl; an ω-carboxy$(C_1-C_7)$alkyl; an ω-$(C_1-C_7)$alkoxycarbonyl$(C_1-C_7)$alkyl; an ω-benzyloxycarbonyl$(C_1-C_7)$alkyl; an ω-amino$(C_2-C_7)$alkyl in which the amino group is free or substituted by one or two $(C_1-C_7)$alkyls, or in the form of an ammonium ion; or an ω-carbamoyl$(C_1-C_7)$alkyl in which the carbamoyl is free or substituted by one or two $(C_1-C_7)$alkyls;

$R_8$ and $R_9$ are each independently a hydrogen; a $(C_1-C_7)$alkyl; or a group —$CH_2$—Ar; $R_9$ can also be a group Ar; a $(C_3-C_8)$alkenyl; a $(C_1-C_7)$alkylcarbonyl; a formyl; a $(C_1-C_7)$alkylthiocarbonyl; a $(C_3-C_7)$cycloalkylcarbonyl; a $(C_3-C_7)$cycloalkylthiocarbonyl; an ω-amino$(C_2-C_7)$alkylcarbonyl in which the amino is free or substituted by one or two $(C_1-C_7)$alkyls; an ω-hydroxy$(C_1-C_7)$alkylcarbonyl; an ω-benzyloxy$(C_1-C_7)$alkylcarbonyl; a pyridylcarbonyl; a methylpyridylcarbonyl; a thienylcarbonyl; a group —CO—Ar; a group —CO—$CH_2$—Ar; a $(C_1-C_7)$alkoxycarbonyl; a phenoxycarbonyl; a phenoxythiocarbonyl; a benzyloxycarbonyl; a group —CO—$CR_{10}R_{23}$—$NR_{11}R_{27}$; a group —$CR_{10}R_{23}COR_{12}$; a group —$(CH_2)_tCOR_{12}$; a group —CO$(CH_2)_uCOR_{12}$; a group —$CONR_{14}R_{24}$; a group —$CSNR_{14}R_{24}$; or a heterocyclic radical selected from pyrazolyl, imidazolyl, triazolyl, tetrazolyl, pyridyl, pyridazinyl, pyrimidinyl and thiazolyl;

or else $R_8$ and $R_9$, together with the nitrogen atom to which they are bonded, form hydantoin, N-methylhydantoin or a heterocyclic radical selected from morpholin-4-yl, pyrrol-1-yl, Δ3-pyrrolin-1-yl, pyrrolidin-1-yl and isoindolin-2-yl, in which the benzene ring is unsubstituted or substituted by a halogen, a $(C_1-C_7)$alkyl, a trifluoromethyl or a methoxy;

$R_{10}$ and $R_{23}$ are each independently hydrogen; a $(C_1-C_7)$alkyl; or a benzyl;

or else $R_{10}$ and $R_{23}$, together with the carbon atom to which they are bonded, form a $(C_3-C_7)$cycloalkyl;

$R_{11}$ and $R_{27}$ are each independently hydrogen; or a $(C_1-C_7)$alkyl;

$R_{12}$ is a hydroxyl; a $(C_1-C_7)$alkoxy; or an amino which is free or substituted by one or two $(C_1-C_7)$alkyls;

$R_{14}$ and $R_{24}$ are each independently hydrogen; or a $(C_1-C_7)$alkyl; $R_{24}$ can also be a $(C_1-C_7)$alkyl substituted by $R_{15}$; a group Ar; a $(C_3-C_7)$cycloalkyl; or an adamantyl;

or $R_{14}$ and $R_{24}$, together with the nitrogen atom to which they are bonded, form a heterocycle selected from morpholine, thiomorpholine, piperazine, azetidine, pyrrolidine, piperidine and perhydroazepine, said heterocycle being unsubstituted or substituted by one or more methyl groups, a phenyl or an amino group which is free or carries a protecting group;

$R_{15}$ is a group Ar; a pyridyl; a hydroxyl; a $(C_1-C_7)$alkoxy; a group —$NR_{11}R_{27}$; a carboxyl; or a $(C_1-C_7)$alkoxycarbonyl;

$R_{16}$ and $R_{17}$ are each independently hydrogen; or a $(C_1-C_7)$alkyl;

or else $R_{16}$ and $R_{17}$, together with the nitrogen atom to which they are bonded, form a heterocycle selected from morpholine, thiomorpholine, azetidine, pyrrolidine, piperidine and piperazine, substituted in the 4-position by $R_{18}$, and perhydroazepine;

$R_{18}$ is a hydrogen; a $(C_1-C_7)$alkyl; a phenyl; a benzyl; a $(C_1-C_7)$alkylcarbonyl; a formyl; a benzoyl; a $(C_1-C_7)$alkoxycarbonyl; a phenoxycarbonyl; or a carbamoyl which is free or substituted by one or two $(C_1-C_7)$alkyls;

$R_{19}$ and $R_{20}$ are each independently hydrogen; or a $(C_1-C_8)$alkyl; $R_{20}$ can also be a $(C_3-C_7)$cycloalkyl which is unsubstituted or substituted by a $(C_1-C_4)$alkyl; a group Ar; a pyridyl; a methylpyridyl; a piperid-4-yl substituted in the 1-position by $R_{18}$; a piperid-1-yl; a pyrrolidin-1-yl; a morpholin-4-yl; a thiazol-2-yl; an indanyl; an adamantyl; or a $(C_1-C_7)$alkyl substituted by one or more halogens or $R_{26}$;

or else $R_{19}$ and $R_{20}$, together with the nitrogen atom to which they are bonded, form a heterocyclic radical $R_{25}$;

$R_{21}$ and $R_{22}$ are each independently hydrogen; or a $(C_1-C_7)$alkyl;

or else $R_{21}$ and $R_{22}$, together with the nitrogen atom to which they are bonded, form a heterocyclic radical $R_{25}$;

$R_{25}$ is a morpholin-4-yl; a thiomorpholin-4-yl; an azetidin-1-yl which is unsubstituted or substituted in the 3-position by a group —$NR_{11}R_{27}$, a $(C_1-C_7)$alkyl, a phenyl, a benzyl or a $(C_1-C_7)$alkylcarbonyl; a perhydroazepin-1-yl; a piperazin-1-yl which is unsubstituted or substituted in the 4-position by a $(C_1-C_7)$alkyl, a phenyl, a benzyl, a $(C_1-C_7)$alkylcarbonyl, a $(C_1-C_7)$alkoxycarbonyl or a benzyloxycarbonyl; a piperid-1-yl which is unsubstituted or substituted in the 4-position by a $(C_1-C_7)$alkyl, a phenyl, a benzyl, a $(C_1-C_7)$alkylcarbonyl or a group —$NR_{11}R_{27}$; or a pyrrolidin-1-yl which is unsubstituted or substituted by a $(C_1-C_7)$alkyl, a phenyl, a benzyl, a $(C_1-C_7)$alkylcarbonyl, a hydroxymethyl, a carboxyl, a $(C_1-C_7)$alkoxycarbonyl or a carbamoyl which is unsubstituted or substituted by one or two $(C_1-C_7)$alkyls;

$R_{26}$ is a hydroxyl; a $(C_1-C_7)$alkoxy; a cyano; a carboxyl; a $(C_1-C_7)$alkoxycarbonyl; a benzyloxycarbonyl; a group —$NR_{11}R_{27}$; a carbamoyl which is free or substituted by one or two $(C_1-C_7)$alkyls; a pyrrolidin-1-ylcarbonyl; a piperid-1-ylcarbonyl; a perhydroazepin-1-ylcarbonyl; a group Ar; a $(C_3-C_7)$cycloalkyl; an adamantyl; or a heterocyclic radical selected from a pyridyl, a methylpyridyl, a furanyl, a tetrahydrofuranyl, a thienyl, a methylthienyl, a pyrrolidin-1-yl, a piperid-1-yl and a perhydroazepin-1-yl;

Ar is a phenyl which is unsubstituted or monosubstituted or polysubstituted by a substituent selected from a halogen atom, a $(C_1-C_7)$alkyl, a trifluoromethyl, a hydroxyl, a $(C_1-C_7)$alkoxy, a carboxyl, a $(C_1-C_7)$alkoxycarbonyl, a $(C_1-C_7)$alkylcarbonyloxy, a nitro, a cyano, an amino, a $(C_1-C_7)$alkylamino and a di$(C_1-C_7)$alkylamino, said substituents being identical or different;

t is an integer which can vary from 2 to 5;

u is an integer which can vary from 0 to 5; and m is 1 or, if $R_6$ is a halogen, a $(C_1-C_7)$alkyl or a $(C_1-C_7)$alkoxy, m can also be 2, 3 or 4, or else $(R_6)_m$ can be m substituents having different meanings selected from halogen, $(C_1-C_7)$alkyl and $(C_1-C_7)$alkoxy; and their salts where appropriate.

If a compound according to the invention has one or more asymmetric carbons, the invention includes all the optical isomers of this compound.

The salts of the compounds of formula (I) according to the present invention include those with mineral or organic acids which permit a suitable separation or crystallization of the compounds of formula (I), such as picric acid, oxalic acid or an optically active acid, for example a mandelic acid or a camphosulfonic acid, and mineral or organic acids which form physiologically acceptable salts such as the hydrochloride, hydrobromide, sulfate, hydrogensulfate, dihydrogenphosphate, maleate, fumarate and naphthalene-2-sulfonate.

The salts of the compounds of formula (I) also include those with organic or mineral bases, for example the salts with alkali metals or alkaline earth metals, such as the sodium, potassium and calcium salts, the sodium and potassium salts being preferred, or with an amine such as trometamol, or else those with arginine, lysine or any physiologically acceptable amine.

According to the present invention, halogen is understood as meaning an atom selected from fluorine, chlorine, bromine and iodine, preferably fluorine or chlorine.

According to the present invention, nitrogen-protecting group is understood as meaning a group such as a $(C_1-C_7)$alkyl, for example a methyl or a tert-butyl; a benzyl; a substituted benzyl such as p-nitrobenzyl, p-chlorobenzyl or p-methoxybenzyl; a benzhydryl; a trityl; a benzoyl; a $(C_1-C_4)$alkylcarbonyl, for example an acetyl; a $(C_1-C_4)$alkoxycarbonyl, for example a methoxycarbonyl, an ethoxycarbonyl or a tert-butoxycarbonyl; or a benzyloxycarbonyl.

According to the present invention, $C_1-C_7$-, $C_1-C_8$- or $C_1-C_4$-alkyl is understood as meaning a linear or branched $C_1-C_7$-, $C_1-C_8$- or $C_1-C_4$-alkyl. $C_1-C_7$- or $C_1-C_4$-alkoxy is understood as meaning a linear or branched $C_1-C_7$- or $C_1-C_4$-alkoxy.

By convention, in the following description and in the claims, the 1,3-dihydro-2H-benzimidazol-2-one heterocycle is numbered as follows for the compounds according to the invention:

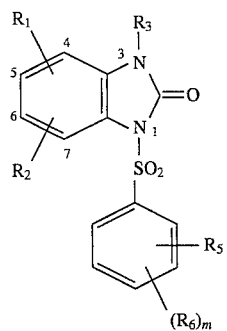

Advantageously, the present invention relates to compounds of the formula

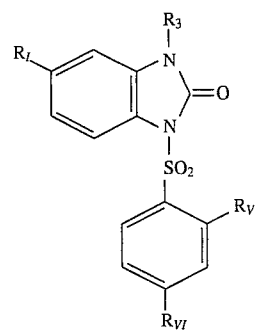

in which:

$R_I$ is a $(C_1-C_4)$alkoxy or a chlorine or fluorine atom;

$R_V$ is hydrogen or a methoxy;

$R_{VI}$ is a $(C_1-C_7)$alkylcarboxamido, a group —NHCO—Ar, a group —CONR$_{19}$R$_{20}$, a group —NR$_8$CONR$_{14}$R$_{24}$, a $(C_1-C_7)$alkoxy or an amino which is free or substituted by one or two $(C_1-C_7)$alkyls; and the substituents $R_3$, Ar, $R_8$, $R_{19}$, $R_{20}$, $R_{14}$ and $R_{24}$ are as defined above for the compounds of formula (I); and their salts.

Very particularly preferred compounds are those of the formula

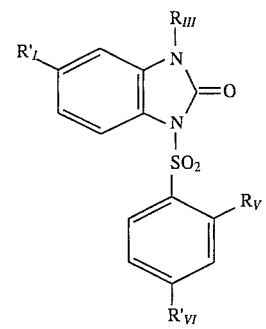

in which:

$R'_I$ is an ethoxy or a chlorine;

$R_{III}$ is a cyclohexyl or a group Ar;

$R_V$ is hydrogen or a methoxy;

$R'_{VI}$ is a group —CONR$_{19}$R$_{20}$ or a group —NR$_8$CONR$_{14}$R$_{24}$; and the substituents Ar, $R_{19}$, $R_{20}$, $R_8$, $R_{14}$ and $R_{24}$ are as defined above for the compounds of formula (I); and their salts.

The following abbreviations are in used the description and in the Examples:

DCM: dichloromethane
ether: diethyl ether
iso ether: diisopropyl ether
MeOH: methanol
EtOH: ethanol
Me, OMe: methyl, methoxy
Et, OEt: ethyl, ethoxy
iPr, nPr: isopropyl, n-propyl
nBu, iBu, tBu: n-butyl, isobutyl, tert-butyl
Ph: phenyl
Bz: benzyl
Ac: acetyl
AcOEt: ethyl acetate
AcOH: acetic acid
HCl: hydrochloric acid DMF: dimethylformamide
THF: tetrahydrofuran
DMSO: dimethyl sulfoxide
DIPEA: diisopropylethylamine
NaOH: sodium hydroxide
NaHCO₃: sodium hydrogencarbonate
Na₂SO₄: sodium sulfate
BOP: benzotriazol-1-yloxytris(dimethylamino)phosphoniumhexafluorophosphate
Lawesson's reagent: 2,4-bis(4-methoxyphenyl)-1,3-dithia-2,4-diphosphetane-2,4-disulfide
M.p.: melting point
Hg: mercury
TLC: thin layer chromatography
HPLC: high pressure liquid chromatography aqueous hydrochloric acid: dilute hydrochloric acid, about 1N
B.p.: boiling point
NMR: nuclear magnetic resonance
s: singlet
t: triplet
q: quadruplet
m: unresolved signals
RT: room temperature The present invention further relates to a process for the preparation of the compounds according to the invention and of their salts, which comprises:

1/ reacting a benzenesulfonyl halide of the formula

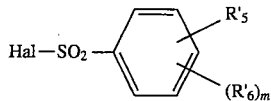

in which $R'_5$ and $R'_6$ are respectively either $R_5$ and $R_6$ as defined above for (I), or precursor groups of $R_5$ and $R_6$, with a compound of the formula

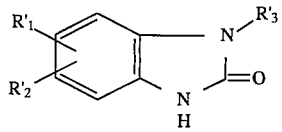

in which $R'_1$, $R'_2$ and $R'_3$ are respectively either $R_1$, $R_2$ and $R_3$ as defined for (I), or precursor groups of $R_1$, $R_2$ and $R_3$; and 2/ either, if $R'_1=R_1$, $R'_2=R_2$, $R'_3=R_3$, $R'_5=R_5$ and $R'_6=R_6$, isolating the resulting compound of formula (I);

3/ or, if any one of the groups $R'_1$, $R'_2$, $R'_3$, $R'_5$ and/or $R'_6$ is respectively a precursor group of $R_1$, $R_2$, $R_3$, $R_5$ and/or $R_6$, subjecting the compound obtained, hereafter called compound (I'), to a subsequent treatment in order to prepare the compound of formula (I) by converting any one of the groups $R'_1$, $R'_2$, $R'_3$, $R'_5$ and/or $R'_6$ to $R_1$, $R_2$, $R_3$, $R_5$ and/or $R_6$ respectively; and 4/ optionally converting the compound obtained in step 2 or in step 3 to one of its salts.

The conversion of a substituent $R'_1$, $R'_2$, $R'_3$, $R'_5$ and/or $R'_6$ to $R_1$, $R_2$, $R_3$, $R_5$ and/or $R_6$ respectively can be effected either from the compound of formula (I') or from one of the intermediates useful in the preparation of (I).

The reaction of step 1 is carried out in an anhydrous solvent such as DMF or THF, in the presence of a metal hydride such as, for example, sodium hydride, or in the presence of an alcoholate such as potassium tert-butylate.

The benzimidazol-2-one derivatives (II) are known or can be prepared by known methods according to different procedures.

N-Substituted benzimidazol-2-one derivatives (II), useful as starting materials for the preparation of the compounds according to the invention, can be prepared by processes described in patents GB 2 127 408 and GB 1 575 386, patent applications JP 62-249 982, JP 53-009 770 and JP 51-131 875, patents BE 770 911, BE 859 415 and BE 830 403 and patent applications EP 477 819, EP 454 330 and EP 526 434.

The following publications likewise describe N-substituted benzimidazol-2-one derivatives:

Monatsh. Chem., 1985, 116 (5), 639–644.

Eur. J. Med. Chem.-Chim. Ther., 1983, 18 (6), 495–500.

N-Substituted benzimidazol-2-one derivatives can also be prepared by methods such as those described in the following publications:

Pharmazie, 1979, 34 (9), 576.

Pol. J. Chem., 1979, 53 (9), 1883–1887.

J. Heterocycl. Chem., 1970, 7 (4), 807–813.

Eur. J. Med. Chem.-Chim. Ther., 1981, 10 (4), 321–326.

In one particular embodiment, the benzimidazolones can be prepared by the process described in Eur. J. Med. Chem., 1981, 16 (4), 321–326, in the following manner:

The reaction of a primary amine of the formula $$H_2N-R'_3 \quad (IV)$$

with substituted orthodinitrobenzenes or orthochloronitrobenzenes (V) of the formula

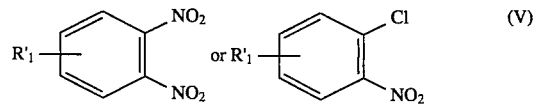

in which $R'_1$ is other than a nitro group, in alcoholic solution, in the presence or absence of a base such as triethylamine, at room temperature or under reflux, gives the N-substituted 2-nitroanilines of the formula

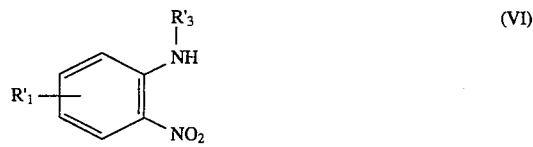

The compounds (VI) can also be obtained by heating the compounds (IV) and (V) in 2-ethoxyethanol (J. Chem. Soc., 1960, 314–318), in ethylene glycol in the presence of sodium acetate, in 1,2,3,4-tetramethylbenzene or in DE'CALINE®.

The compounds (VI) in which $R'_1$ is a $(C_1-C_7)$alkoxy, $(C_3-C_7)$cycloalkoxy, $(C_3-C_7)$cycloalkylmethoxy, phenoxy, benzyloxy or ω-methoxy$(C_2-C_7)$alkoxy group are obtained by reacting a compound (VI) in which $R'_1$=Cl with a sodium alcoholate by the process described in J. Org. Chem., 1963, 28, 3117, or with a sodium alcoholate in the presence of a phase transfer catalyst such as tris[2-(2-methoxyethoxy)ethyl]amine (TDA-1).

The compounds (VI) in which $R'_3$ is a $(C_1-C_8)$alkylene group substituted by a $(C_1-C_4)$alkoxy can be prepared by reacting a compound (VI) in which the substituent $R'_3$ is a $(C_1-C_8)$alkyl substituted by a hydroxyl with a $(C_1-C_4)$alkyl halide in the presence of a metal hydride such as, for example, sodium hydride, in an anhydrous solvent such as DMF or THF.

The compounds of formula (VI) are reduced to N-substituted orthophenylenediamines of formula (VII):

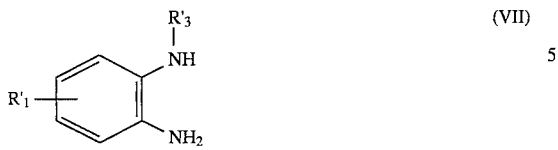

The reduction can be catalytic, for example using palladium-on-charcoal or Raney® nickel, or chemical using iron, zinc or tin under acid conditions (J. Chem. Soc., 1960, 314).

The compounds of formula (VII) react with ethyl chloroformate or methyl chloroformate, in a solvent such as chloroform or dichloromethane, in the presence or absence of a base such as triethylamine, or in a DMF/water mixture in the presence of potassium carbonate, to give the compounds of formulae (VIII) and/or (VIII'):

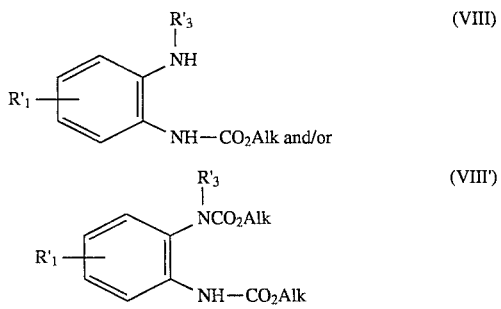

in which Alk is an ethyl or a methyl.

The compounds of formulae (VIII) and/or (VIII') are cyclized to the benzimidazol-2-one (IX):

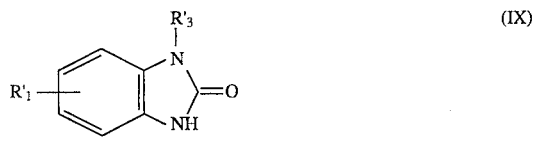

by heating with sodium ethylate.

The compounds (IX) can also be obtained by reacting a compound of formula (VII) with urea by the process described in J. Chem. Soc., 1960, 314, or with 1,1-carbonyldiimidazole by a process described in European patent 92 391.

The compounds of formula (II) carrying certain substituents $R'_1$, $R'_2$ on their benzene moiety are used as precursors for the preparation of compounds of formula (II) carrying other substituents $R'_1$, $R'_2$. For example, the compounds (II) in which $R'_1$ and/or $R'_2$=H can be nitrated with conventional reagents. They can also be acylated by reaction with an acid chloride of the formula RCOCl, in which R is a ($C_1$–$C_7$)alkyl or a phenyl, in the presence of a Lewis acid such as aluminum chloride, in order to prepare a compound (II) in which $R'_1$ and/or $R'_2$=—COR. The compound (II) in which $R'_1$ is an amino group is prepared by the catalytic hydrogenation or chemical reduction of a compound (II) in which $R'_1$ is a nitro group and $R'_2$ is hydrogen.

In the particular case where $R'_3$ is an azetidin-3-yl, a piperid-4-yl, a piperazin-1-yl or a ($C_1$–$C_7$)alkylene group substituted by an azetidin-3-yl, a piperid-4-yl or a piperazin-1-yl, in which the nitrogen atom is substituted by $R_{18}$=a ($C_1$–$C_7$)alkylcarbonyl, a formyl, a benzoyl, a ($C_1$–$C_7$)alkoxycarbonyl, a phenoxycarbonyl or a carbamoyl which is unsubstituted or substituted by one or two ($C_1$–$C_7$)alkyls, the substitution on the nitrogen atom can be effected either on the benzimidazol-2-one compound (II) or on the final compound (I) starting from a compound in which the nitrogen atom is unsubstituted ($R_{18}$=H). Thus, if the nitrogen atom is substituted by $R_{18}$=a formyl, a ($C_1$–$C_7$)alkylcarbonyl or a benzoyl, formic acid in the presence of acetic anhydride or respectively an acid chloride or an anhydride is reacted with a compound (II) or a compound (I) in which the nitrogen atom of the heterocyclic radical as defined above is unsubstituted ($R_{18}$=H). If the nitrogen atom is substituted by $R_{18}$=a ($C_1$–$C_7$)alkoxycarbonyl or a phenoxycarbonyl, the appropriate chloroformate is reacted with a compound (II) or a compound (I) in which $R_{18}$=H. A compound (II) or a compound (I) in which $R_{18}$ is a carbamoyl is prepared by reacting ammonia with a compound of formula (II) or a compound of formula (I) in which $R_{18}$= phenoxycarbonyl; a compound of formula (II) or a compound of formula (I) in which $R_{18}$ is an N-($C_1$–$C_7$)alkylcarbamoyl or N,N-di($C_1$–$C_7$)alkylcarbamoyl is prepared by reacting a mono- or di-($C_1$–$C_7$)alkylamine with a compound (II) or a compound (I) in which $R_{18}$ is a carbamoyl. It is also possible to prepare a compound (II) or a compound (I) in which $R_{18}$ is an N-alkylcarbamoyl by reacting an alkyl isocyanate with a compound (II) or a compound (I) in which $R_{18}$=H.

The compounds of formula (IV) are known or can be prepared by known methods. For example, the variously substituted cyclohexylamines are prepared according to J. Org. Chem., 1962, 27, 3568–3572.

The benzenesulfonyl halides (III) are prepared by known methods. Thus, for example, 4-dimethylaminobenzenesulfonyl chloride is prepared according to C. N. Sukenik et al., J. Amer. Chem. Soc., 1977, 99, 851–858.

More generally, the benzenesulfonyl halides (III) in which the substituent $R'_6$ is a dimethylamino group are known or prepared by known methods; p-benzyloxybenzenesulfonyl chloride is prepared according to European patent application EP 229 566.

The alkoxybenzenesulfonyl chloride is prepared from the sodium alkoxybenzenesulfonate, which is itself prepared by reacting an alkyl halide with sodium hydroxybenzenesulfonate.

2,4-Dimethoxybenzenesulfonyl chloride is prepared according to J. Am. Chem. Soc., 1952, 74, 2008.

The halogenoalkoxybenzenesulfonyl chlorides can be prepared according to U.S. Pat. No. 2,540,057.

The benzenesulfonyl halides of the formula

in which:

Alk is a ($C_1$–$C_7$)alkyl;

Y is O or S; and $R''_6$ is a ($C_1$–$C_7$)alkyl, a ($C_3$–$C_7$)cycloalkyl, a ($C_2$–$C_7$)alkenyl, an ω-halogeno($C_2$–$C_7$)alkyl, a polyhalogeno-($C_1$–$C_7$)alkyl, a benzyl, a ($C_1$–$C_7$)alkylcarbonyl, a formyl, a benzoyl or an ω-carboxy($C_1$–$C_7$)alkyl esterified by a ($C_1$–$C_7$)alkyl or a benzyl, are prepared according to D. Hofmann et al. in Liebigs Ann. Chem., 1982, 282–297.

Trimethylsilyl chlorosulfonate is reacted with benzene compounds carrying the substituents $YR''_6$ and OAlk in the 1,3-position, in a solvent such as DCM, at RT. This is followed by application of the method of R. Passerini et al. in Gazz. Chim. Ital., 1960, 90, 1277–89, and then by neutralization, for example with alkali metal carbonate, after which the product is reacted with a halide, such as $POCl_3$, to give the desired benzenesulfonyl halide.

The benzenesulfonyl halides (III) in which the substituent $R'_6$ is an alkoxycarbonyl, a phenoxycarbonyl, a benzyloxycarbonyl, an alkylthio, a phenylthio, a benzylthio or a group —$SR_7$, $R_7$ being as defined for (I), are prepared according to Col. Czechoslov. Chem. Commun., 1984, 49, 1184, from an aniline derivative substituted by the same group $R'_6$, said aniline derivative itself being obtained from the corresponding nitro derivative.

The nitrobenzoic acid derivatives are known; an appropriate esterification reaction with this acid gives the corresponding alkyl and phenyl esters.

The benzenedisulfonyl dihalides (III, $R'_6=SO_2Hal$) are known or prepared by known methods. For example, 2,4-dimethoxybenzene-1,5-disulfonyl dichloride is described in R. J. W. Cremlyn, J. Chem. Soc. C, 1969, 1341–1345.

The halogenoalkoxybenzenesulfonyl chlorides (III, $R'_6=$ ω-halogenoalkoxy) are used for the preparation of compounds according to the invention in which the substituent $R_6$ is an ω-aminoalkoxy which is unsubstituted or substituted by one or two alkyls, in accordance with the following equation:

in which Alk' is a $(C_2–C_7)$alkyl and A and A' are each independently a hydrogen or a $(C_1–C_7)$ alkyl.

The benzenesulfonyl halides (III) in which $R'_6$ in the 4-position is a sulfamoyl substituted by $R_{21}$ and $R_{22}$ ($R'_6=$ —$SO_2NR_{21}R_{22}$) and $R'_5$ in the 2-position is a $C_1–C_7$-alkoxy can be prepared by the following process: 3-Alkoxy- 4-nitrobenzenesulfonyl halides are prepared by reacting chlorosulfonic acid with 2-alkoxynitrobenzene compounds and the resulting sulfonyl chloride is reacted with compounds $HNR_{21}R_{22}$. The corresponding benzenesulfonyl halides are obtained according to Col. Czechoslov. Chem. Commun., 1984, 49, 1184, from the aniline derivatives substituted by the same group, said aniline derivatives themselves being obtained from the corresponding nitro derivatives.

The benzenesulfonyl halide (III) in which $R'_6$ in the 4-position is an N',N'-diethylureido group ($R'_6=$—NHCO-N(Et)$_2$) can be prepared by reacting chlorosulfonic acid with N',N'-diethyl-N-phenylurea, which is itself obtained by reacting aniline with diethylcarbamoyl chloride.

4-(Morpholin-4-yl)benzenesulfonyl chloride is prepared according to R. J. Cremlyn et al. in Phosphor. Sulfur. Silicon., 1992, 73 (1–4), 107–120.

For certain meanings of the substituents $R_1$, $R_2$, $R_3$, $R_5$ and/or $R_6$, the compounds (I) according to the invention can be prepared from a precursor of formula (I') substituted by a group $R'_1$, $R'_2$, $R'_3$, $R'_5$ and/or $R'_6$, called a precursor group of $R_1$, $R_2$, $R_3$, $R_5$ and/or $R_6$, using methods known to those skilled in the art.

The following description relates to the preparation of the compounds of formula (I) carrying substituents $R_1$ and/or $R_6$; the same methods are applied to the preparation of the compounds in which the substituents $R_2$ and/or $R_5$ have the meanings indicated for $R_1$ and/or $R_6$.

The compounds (I) in which $R_1$ and/or $R_6$ is a hydroxyl can be obtained by the catalytic hydrogenation of a compound of formula (I') in which $R'_1$ and/or $R'_6$ is a benzyloxy, for example in the presence of palladium-on-charcoal. These compounds can also be prepared from analogous compounds of formula (I') in which $R'_1$ and/or $R'_6$ is an amino group by using the method described in J. Org. Chem., 1977, 42, 2053.

The compounds of formula (I) in which $R_1$ and/or $R_6$ is a $(C_1–C_7)$alkoxy can be prepared directly by the process according to the invention starting from the correctly substituted compounds of formulae (II) and (III).

The compounds (I') in which $R'_1$ and/or $R'_6$ is a hydroxyl can also be used to prepare compounds (I) in which $R_1$ and/or $R_6$ is a $(C_1–C_7)$alkoxy by reaction with a $C_1–C_7$-alkyl halide in the presence of a base such as a metal hydride or an alkali metal or alkaline earth metal carbonate like $K_2CO_3$ or $Cs_2CO_3$, in a solvent such as THF or DMF. Likewise, the compounds of formula (I) in which $R_1$ and/or $R_6$ is an ω-aminoalkoxy are prepared by reacting an ω-chloroalkylamine with the compounds in which $R'_1$ and/or $R'_6$=OH; again, the compounds in which $R_1$ and/or $R_6$ is an ω-hydroxyalkoxy are prepared by reaction with a chloroalkyl alcohol; in the particular case of the preparation of a compound (I) in which $R_1$ and/or $R_6$=—$O(CH_2)_2OH$, it is also possible to react ethylene carbonate with a compound (I') in which $R'_1$ and/or $R'_6$=OH.

The compounds of formula (I) in which $R_1$ and/or $R_6$ is a formyloxy or respectively a $(C_1–C_7)$alkylcarbonyloxy or a benzoyloxy are obtained by reacting formic acid in the presence of dicyclohehylcarbodiimide (J. Huang et al., J. Chem. Res. (S), 1991, 292–293) or respectively an acid halide or an anhydride with a compound (I') in which $R'_1$ and/or $R'_6$ is a hydroxyl.

The compounds of formula (I) in which $R_6$ is a group —$OR_7$, $R_7$ being an ω-carbamoyl$(C_1–C_7)$alkyl which is free or substituted by one or two $C_1–C_7$-alkyls, can be prepared from a compound (I') in which $R'_6$ is a group —$OR''_6$, $R''_6$ being an ω-carboxy$(C_1–C_7)$alkyl esterified by a $C_1–C_7$-alkyl. This preparation is carried out in a manner conventional to those skilled in the art by reaction with a correctly chosen amine.

To prepare compounds of formula (I) in which $R_1$ and/or $R_6$ is a $(C_1–C_7)$monoalkylamino, a compound of formula (I') in which $R'_1$ and/or $R'_6$ is an amino group is reacted with an aldehyde or a ketone in an acid medium, in the presence of a reducing agent such as sodium cyanoborohydride; the compounds (I) in which $R_1$ and/or $R_6$ is a dialkylamino are prepared by an identical reaction.

The compounds of formula (I) in which $R_6$ is an amino group substituted by a benzyl, which is itself optionally substituted, or by a $(C_3–C_8)$alkene can be prepared by reacting a benzyl chloride or a $(C_3–C_8)$-chloroalkene with a compound of formula (I') in which $R'_6$ is an amino or $(C_1–C_7)$alkylamino group.

The compounds of formula (I) in which $R_6$ is a Δ3-pyrrolin-1-yl group are prepared by reacting cis-1,4-dichlorobut-2-ene with the compounds of formula (I') in which $R'_6$ is an amino group, in the presence of a base such as triethylamine, under an inert atmosphere. The compounds of formula (I) in which $R_6$ is a pyrrolidin-1-yl group are then prepared by hydrogenation.

The reaction of cis-1,4-dichlorobut-2-ene with the compounds of formula (I') in which $R'_6$ is an amino group can also be carried out in air, in the presence of a base such as sodium carbonate, and gives, under these conditions, a mixture of a compound of formula (I) in which $R_6$ is a Δ3-pyrrolin-1-yl group and a compound of formula (I) in which $R_6$ is a pyrrol-1-yl group, which can be separated by chromatography.

The compounds of formula (I) in which $R_6$ is an isoindolin-2-yl group are prepared by reacting α,α'-dibromo-o-xylene with the compounds of formula (I') in which $R'_6$ is an amino group, in the presence of a base such as triethylamine, and in a solvent such as dimethyl-formamide, under reflux.

The compounds of formula (I) in which $R_6$ is a 1-methyl-2,4-dioxoimidazolin-3-yl group are prepared in two steps: sarcosine is reacted with a compound of formula (I') in which $R'_6$ is a phenoxycarboxamido, in the presence of a base such as triethylamine, to give a compound of formula (I') in which $R'_6$ is an N'-carboxymethyl-N'-methylureido; the previously obtained product then cyclizes on heating at 100° C. under vacuum.

If $R'_1$ and/or $R'_6$ is an amino, it is also possible to perform a nitrosation, for example in the presence of nitrous acid or sodium nitrite, in order to prepare a compound (I') in which $R'_1$ and/or $R'_6$ is a diazonium salt; the compounds (I) according to the invention in which $R_1$ and/or $R_6$ is a cyano, a halogeno or a $C_1$–$C_7$-thioalkyl are then obtained by reactions known to those skilled in the art. Finally, compounds (I) in which $R_1$ and/or $R_6$ is a group of the formula RCONH—, ROCONH—, RNHCONH— or $RSO_2NH$—, in which R is a ($C_1$–$C_7$)alkyl, a group Ar or a group —$CH_2Ar$, can be prepared by conventional reactions starting from compounds (I') in which $R'_1$ and/or $R'_6=NH_2$.

The compounds of formula (I) in which $R_6$ is a ($C_1$–$C_7$)alkoxycarbonyl can be prepared directly by the process according to the invention. Using methods known to those skilled in the art, they make it possible to obtain the compounds of formula (I) in which $R_6$ is a carboxyl group.

The compounds of formula (I') in which $R'_6$ is a benzyloxycarbonyl make it possible, by catalytic hydrogenation, to obtain the compounds (I) in which $R_6$ is a carboxyl. Reaction with a thionyl halide gives the compounds of formula (I') in which $R'_6$ is a halogenocarbonyl. Such compounds are reacted with a compound $HNR_{19}R_{20}$ in order to prepare compounds of formula (I) in which $R_6$ is a carbamoyl substituted by $R_{19}$ and $R_{20}$. The compounds of formula (I') in which the substituent $R'_6$ is a phenoxycarbonyl can also be used to obtain the compounds (I) in which $R_6$ is a phenylcarbamoyl or a ($C_1$–$C_7$)alkylcarbamoyl by reaction with an aniline or a ($C_1$–$C_7$)alkylamine. An aniline substituted on the phenyl by at least one of the phenyl substituents as defined for Ar, or an alkylamine substituted on the alkyl by $R_{26}$ makes it possible to obtain compounds of formula (I) in which $R_6$ is a phenylcarbamoyl substituted on the phenyl or, respectively, an alkylcarbamoyl substituted on the alkyl by $R_{26}$.

The compounds of formula (I') in which $R'_6$ is a carboxyl can be used to obtain the compounds of formula (I) in which $R_6$ is a group —$CONR_{19}R_{20}$ by reaction with a compound of the formula $HNR_{19}R_{20}$, in the presence of BOP and an amine such as diisopropylethylamine.

In the same way, the compounds of formula (I) in which $R_6$ is a group —$CONHCR_{10}R_{23}COR_{12}$ are prepared from compounds of formula (I') in which $R'_6$ is either a group —COCl or a phenoxycarbonyl group by reaction with $H_2NCR_{10}R_{23}COR_{12}$. They can also be prepared from compounds of formula (I') in which $R'_6$ is a carboxyl by reaction with a compound $H_2NCR_{10}R_{23}COR_{12}$, in the presence of BOP and an amine such as diisopropylethylamine.

The compounds of formula (I) in which $R_6$ is a group —$COR_{25}$ are prepared from corresponding compounds (I') in which $R'_6$ is a phenoxycarbonyl by reaction with $R_{25}H$.

A compound (I) in which $R_6$ is a thiocarbamoyl can be prepared by reacting Lawesson's reagent with a compound (I) in which $R_6$ is the corresponding carbamoyl.

A compound (I') in which $R'_6$ is a nitro group makes it possible to obtain a compound (I) in which $R_6$ is an amino group by catalytic hydrogenation, for example in the presence of platinum oxide, Raney® nickel or palladium-on-charcoal, or by chemical reduction, for example in the presence of tin or iron in an acid medium; other compounds in which the amino group is substituted can then be prepared using reactions well known to those skilled in the art.

The compounds (I) in which $R_6$ is a group —$NR_8R_9$, $R_9$ being a formyl, a ($C_1$–$C_7$)alkylcarbonyl, a ($C_3$–$C_7$)cycloalkylcarbonyl, an optionally substituted benzoyl, a pyridylcarbonyl, a methylpyridylcarbonyl or a thienylcarbonyl, are obtained by reacting formic acid in the presence of acetic anhydride or respectively the appropriate anhydride or the appropriate acid chloride with a compound (I') in which $R'_6$ is an amino group, in the presence of an amine such as triethylamine.

In the same way, the acid chloride $R_{11}R_{27}NCR_{10}R_{23}COCl$ is reacted with a compound of formula (I') in which $R'_6$ is a group —$NHR_8$ in order to prepare a compound of formula (I) in which $R_6$ is a group —$NR_8COCR_{10}R_{23}NR_{11}R_{27}$.

To prepare a compound of formula (I) in which $R_6$ is a group —$NR_8CO$—($C_2$–$C_7$)alkyl-NAA' in which A and A' are as defined above, a halogeno($C_3$–$C_8$)acyl halide, such as, for example, 3-chloropropionyl chloride or 4-chlorobutyryl chloride, is reacted with a compound of formula (I') in which $R'_6$ is a group —$NHR_8$, in the presence of a base such as triethylamine; the compound obtained is then reacted with an amine HNAA' to give the compound of formula (I) designated above.

Likewise, a compound of formula (I) in which $R_6$ is a group —$NR_8CO$—($C_1$–$C_7$)alkyl—O—$CH_2$–$C_6H_5$ is prepared by reacting an ω-benzyloxy-($C_1$–$C_7$)alkylcarbonyl halide with a compound of formula (I') in which $R'_6$ is a group —$NHR_8$. Hydrogenation of the previous compound, in the presence of a catalyst such as 5% palladium-on-charcoal, gives a compound of formula (I) in which $R_6$ is a group —$NR_8CO$—($C_1$–$C_7$)alkyl-OH.

According to another preparatory example, a compound (I) in which $R_6$ is a ($C_1$–$C_7$)alkylsulfonamido group, a benzylsulfonamido or a group —$NHSO_2Ar$ is obtained by reacting a ($C_1$–$C_7$)alkylsulfonyl halide, a benzene-sulfonyl halide or a compound $ArSO_2C_1$, respectively, with a compound (I') in which $R'_6$ is an amino group.

The compounds of formula (I') in which $R'_6$ is an amino group are also useful for the preparation of compounds in which this amino group is substituted by a group —$(CH_2)_t$—$COR_{12}$. In this case, a compound of the formula Hal—$(CH_2)_t$—COOAlk, in which Hal is a halogen, for example bromine, and Alk is a $C_1$–$C_7$-alkyl, is reacted with (I') in the presence of cuprous chloride; if required, the resulting ester is converted to the acid or an amide. A compound (I) in which $R_6$ is a group —$NHCO(CH_2)_2CO_2H$ or —$NHCO(CH_2)_3CO_2H$ can be prepared by reacting an anhydride, such as succinic anhydride or glutaric anhydride, with a compound (I') in which $R'_6$ is an amino. If required, the resulting acid is converted to an ester or an amide.

It is also possible to react ethyloxalyl chloride with a compound (I') in which $R'_6$ is an amino in order to prepare a compound (I) in which $R_6$ is a group —$NHCOCO_2Et$.

In the same way, the compounds of formula (I) in which $R_6$ is an amino group substituted by a group —$CR_{10}R_{23}COR_{12}$ are prepared by reacting a compound of the formula Hal-$CR_{10}R_{23}COR_{12}$ with the corresponding compounds (I') in which the substituent $R'_6$ is an amino.

A compound (I) in which $R_6$ is an amino group substituted by an alkoxycarbonyl, a phenoxycarbonyl or a benzyloxycarbonyl is prepared by reacting a $C_1$–$C_7$-alkyl, phenyl or benzyl chloroformate with a compound (I') in which the substituent $R'_6$ is an amino.

Likewise, a compound of formula (I) in which $R_6$ is a phenoxythiocarbonylamino is obtained by reacting a phenoxythiocarbonyl chloride with a compound of formula (I') in which $R'_6$ is an amino group.

A compound of formula (I) in which $R_6$ is a ureido or a thioureido is prepared by reacting ammonia with a compound of formula (I') in which $R'_6$ is an amino group substituted by a phenoxycarbonyl or a phenoxythiocarbonyl; such a compound of formula (I') is reacted with a correctly substituted aniline or a correctly substituted $C_1$–$C_7$-monoalkylamine or -dialkylamine in order to prepare a compound of formula (I) in which $R_6$ is a correctly substituted N'-phenylureido or a correctly substituted N'-alkylureido or N',N'-dialkylureido in which the alkyl is $C_1$–$C_7$.

It is also possible to prepare other compounds (I) in which $R_6$ is a ureido (—$NHCONR_{14}R_{24}$) or a thioureido (—$NHCSNR_{14}R_{24}$) by reacting a compound $NHR_{14}R_{24}$ with a compound (I') in which $R'_6$ is a phenoxycarbonylamino or, respectively, phenoxythiocarbonylamino group.

A further possibility is to prepare a compound (I) in which $R_6$ is a ureido (—$NHCONR_{14}R_{24}$) or a thioureido by reacting a carbamoyl chloride ($ClCONR_{14}R_{24}$) or, respectively, a thiocarbamoyl chloride with a compound of formula (I') in which $R'_6$ is an amino group.

It is also possible to prepare a compound (I) in which $R_6$ is a thioureido by reacting Lawesson's reagent with a compound (I') in which $R'_6$ is the corresponding ureido.

The compounds (I) in which $R_6$ is a guanidino group which is unsubstituted or monosubstituted or disubstituted by a $C_1$–$C_7$-alkyl, a phenyl or a benzyl can be prepared from the compounds (I') in which $R'_6$ is a phenoxyamido group by reaction with cyanamide or a derivative thereof correctly substituted on the nitrogen.

The compounds (I) in which $R_6$ is a guanidino group substituted in the 2-position by a cyano are prepared in two steps: dimethyl N-cyanodithioiminocarbonate is reacted with a compound (I') in which $R'_6$ is an amino, in a solvent such as n-butanol, under reflux, to give a compound (I') in which $R'_6$ is a group —$NHC(SCH_3)=N$—CN; reaction of the previous compound with an appropriate amine gives the expected compound (I).

It is also possible to prepare a compound (I) in which $R_6$ is an amino group substituted by a ($C_1$–$C_7$)-alkylcarbamoyl or a phenylcarbamoyl by reacting an alkyl or phenyl isocyanate with a compound (I') in which the substituent $R'_6$ is an amino.

Furthermore, a compound (I) in which $R_6$ is a sulfamoyl group substituted by $R_{21}R_{22}$ is prepared by reacting a compound $HNR_{21}R_{22}$ with a compound (I') in which $R'_6$ is a halogenosulfonyl group.

The affinity of the compounds according to the invention for the vasopressin receptors was determined in vitro using the method described in C.J. Lynch et al., J. Biol. Chem., 1985, 260 (5), 2844–2851. This method consists in studying the displacement of tritiated vasopressin bound to the $V_1$ sites of rat liver membranes. The concentrations of the compounds according to the invention which cause a 50% inhibition of the binding of tritiated vasopressin ($IC_{50}$) are low, ranging down to $10^{-7}M$.

The affinity of the compounds (I) according to the invention for the $V_2$ receptors was measured on a bovine kidney membrane preparation by a method adapted from P. Crause et al., Molecular and Cellular Endocrinology, 1982, 28, 529–541, and F. L. Stassen et al., J. Pharmacol. Exp. Ther., 1982, 225, 50–54. The compounds according to the invention inhibit the binding of tritiated arginine vasopressin to the receptors of the membrane preparation. The $IC_{50}$ values of the compounds according to the invention are low, ranging down to $10^{-9}M$.

The antagonistic activity of the compounds according to the invention towards the $V_2$ receptors was demonstrated by the adenylate cyclase activity assay performed by a method adapted from M. Laburthe et al., Molecular Pharmacol., 1986, 29, 23–27. A bovine kidney membrane preparation is used and each product is incubated for 10 minutes at 37° C., either by itself or in the presence of AVP (arginine vasopressin) at a concentration of $3.10^{-8}M$. The cyclic AMP (cyclic adenosine monophosphate) produced is measured by radioimmunoassay. The concentration which causes a 50% inhibition ($IC_{50}$) of the stimulation of adenylate cyclase induced by $3.10^{-8}M$ AVP is determined. The $IC_{50}$ values determined are of the order of $10^{-7}M$, ranging down to $10^{-8}M$.

The agonistic or antagonistic activity of the compounds according to the invention, administered orally, towards the vasopressin receptors is evaluated in hyperhydrated rats (OFA, Sprague-Dawley strain) treated with vasopressin. The antagonistic activity of the compounds according to the invention was also evaluated in normally hydrated rats (OFA, Sprague-Dawley strain) by the technique described in Br. J. Pharmacol., 1992, 105, 787–791. The diuretic effect was observed for some compounds at a dose of 10 mg/kg.

Likewise, the affinity of the compounds (I) according to the invention for the oxytocin receptors was determined in vitro by the displacement of a radioiodinated oxytocin analog bound to the receptors of a gestating rat mammary gland membrane preparation by a technique similar to that described by J. Eland et al. in Eur. J. Pharmacol., 1987, 147, 197–207. The $IC_{50}$ values of the compounds according to the invention reach $10^{-8}M$.

The compounds according to the invention are active after administration by different routes, especially orally.

No signs of toxicity are observed with these compounds at the pharmacologically active doses.

Thus the compounds according to the invention can be used in the treatment or prevention of various vasopressin-dependent or oxytocin-dependent complaints, cardiovascular complaints such as hypertension, pulmonary hypertension, cardiac insufficiency, myocardial infarction or coronary vasospasm, in particular in smokers, unstable angina and PTCA (percutaneous transluminal coronary angioplasty), cardiac ischemia, hemostatic disorders, especially hemophilia, and von Willebrand's syndrome; complaints of the central nervous system, for example migraine, cerebral vasospasm, cerebral hemorrhage, cerebral edemas, depression, anxiety, psychotic states and memory disorders; complaints of the renal system, such as edemas, renal vasospasm, necrosis of the renal cortex, hyponatremia, hypokalemia and Schwartz Bartter's syndrome; complaints of the gastric system, such as gastric vasospasm, hepatocirrhosis, ulcers, the pathology of vomiting, for example nausea, including nausea due to chemotherapy, travel sickness or else the syndrome of inappropriate secretion of antidiuretic hormone (SIADH), diabetes insipidus and enuresis. The compounds according to the invention can also be used in the treatment of disorders of sexual behavior; in women, the compounds according to the invention can be used for treating dysmenorrhea or premature labor. The compounds according to the invention can also be used in the treatment of small cell lung cancer, hyponatremic encephalopathy, Raynaud's disease, pulmonary syndrome and glaucoma and in postoperative treatments, especially after abdominal surgery.

The present invention further relates to pharmaceutical compositions containing an effective dose of a compound according to the invention, or a pharmaceutically acceptable salt thereof, and suitable excipients.

Said excipients are chosen according to the pharmaceutical form and the desired mode of administration.

In the pharmaceutical compositions of the present invention for oral, sublingual, subcutaneous, intramuscular, intravenous, topical, intratracheal, intranasal, transdermal or rectal administration, the active principles of formula (I) above, or their salts where appropriate, can be administered to animals and humans in unit forms of administration, mixed with conventional pharmaceutical carriers, for the prophylaxis or treatment of the above disorders or diseases. The appropriate unit forms of administration include forms for oral administration, such as tablets, gelatin capsules, powders, granules and solutions or suspensions to be taken orally, forms for sublingual, buccal, intratracheal or intranasal administration, forms for subcutaneous, intramuscular or intravenous administration and forms for rectal administration. For topical application, the compounds according to the invention can be used in creams, ointments or lotions.

To obtain the desired prophylactic or therapeutic effect, the dose of active principle can vary between 0.01 and 50 mg per kg of body weight and per day.

Each unit dose can contain from 0.5 to 1000 preferably from 1 to 500 mg, of active ingredients in combination with a pharmaceutical carrier. This unit dose can be administered 1 to 5 times a day so as to administer a daily dosage of 0.5 to 5000 mg, preferably 1 to 2500 mg.

If a solid composition is prepared in the form of tablets, the main active ingredient is mixed with a pharmaceutical vehicle such as gelatin, starch, lactose, magnesium stearate, talc, gum arabic or the like. The tablets can be coated with sucrose, a cellulose derivative or other appropriate substances, or else they can be treated so as to have a sustained or delayed activity and so as to release a predetermined amount of active principle continuously.

A preparation in the form of gelatin capsules is obtained by mixing the active ingredient with a diluent and pouring the resulting mixture into soft or hard gelatin capsules.

A preparation in the form of a syrup or elixir or for administration in the form of drops can contain the active ingredient together with a sweetener, which is preferably calorie-free, methylparaben and propylparaben as antiseptics, a flavoring and an appropriate color.

The water-dispersible powders or granules can contain the active ingredient mixed with dispersants or wetting agents, or suspension agents such as polyvinyl-pyrrolidone, as well as with sweeteners or taste correctors.

Rectal administration is affected using suppositories, which are prepared with binders melting at the rectal temperature, for example cocoa butter or polyethylene glycols.

Parenteral administration is effected using aqueous suspensions, isotonic saline solutions or sterile and injectable solutions which contain pharmacologically compatible dispersants and/or wetting agents, for example propylene glycol or butylene glycol.

The active principle can also be formulated as microcapsules, if appropriate with one or more carriers or additives.

In addition to the products of formula (I) above or one of their pharmaceutically acceptable salts, the compositions of the present invention can contain other active principles which may be useful in the treatment of the disorders or diseases indicated above.

Thus the present invention further relates to pharmaceutical compositions in which several active principles are present in association, one of them being a compound according to the invention.

Thus, according to the present invention, it is possible to prepare pharmaceutical compositions in which a compound according to the invention is present in association with a compound which acts on the reninangiotensin system, such as a converting enzyme inhibitor, an angiotensin II antagonist or a renin inhibitor. A compound according to the invention can also be associated for example with a peripheral vasodilator, a calcium inhibitor, a beta-blocking agent, an alpha-1-blocking agent or a diuretic. Such compositions will be useful in particular in the treatment of hypertension or heart failure.

It is also possible to associate two compounds according to the invention, namely a specific $V_1$ receptor antagonist with a specific $V_2$ receptor antagonist, or else a specific $V_1$ receptor antagonist with a specific oxytocin antagonist.

These associations will make it possible to reinforce the therapeutic activities of the compounds according to the invention.

The invention will now be described in greater detail by means of the non-limiting illustrative Preparations and Examples below.

PREPARATIONS

Preparation of the
1,3-dihydro-2H-benzimidazol-2-ones

Preparation 1

5-Chloro-1,3-dihydro-3-phenyl-2H-benzimidazol-2-one

This compound is prepared by the procedure described in Eur. J. Med. Chem.-Chimica Therapeutica, 1981, 16 (4), 321–326.

Preparation 2

5-Chloro-3-cyclohexyl-1,3-dihydro-2H-benzimidazol-2-one

A) 4-Chloro-2-cyclohexylamino-1-nitrobenzene

A mixture consisting of 19.4 g of 2,4-dichloro-1-nitrobenzene, 40 g of cyclohexylamine and 100 ml of 2-ethoxyethanol is refluxed for 12 hours.

The solvent is evaporated off under vacuum, the residue is taken up with ethyl ether, washed with $H_2O$ and dried over $Na_2SO_4$ and the solvent is evaporated off under vacuum to give 11.7 g of the expected product after crystallization from iso ether. M.p.=125° C.

B) 1-Amino-4-chloro-2-cyclohexylaminobenzene 12 g of the compound obtained in step A), 8 g of iron powder, 15 ml of water and 15 ml of ethanol are brought to the reflux point. 30 ml of concentrated hydrochloric acid in 20 ml of water and 20 ml of ethanol are then introduced dropwise over 30 minutes. The reaction medium is then refluxed for 1 hour 30 minutes.

After cooling, the reaction medium is poured onto ice and a saturated solution of $NaHCO_3$ is added. The product is extracted with AcOEt, washed with water, then with a saturated solution of $NaHCO_3$ and then with water and dried over $Na_2SO_4$ and the solvent is evaporated off under vacuum. The residue is chromatographed on silica using isopropyl ether as the eluent to give 9.4 g of the expected product, which is used as such in the next step.

C) 5-Chloro-3-cyclohexyl-1,3-dihydro-2H-benzimidazol-2-one

A mixture of 4.5 g of the compound obtained in step B) with 2.5 g of urea and 10 ml of 1,2,3,4-tetramethylbenzene is heated at 170°–180° C. for 90 minutes.

After cooling, the reaction medium is taken up with ethyl acetate, washed with water and dried over sodium sulfate and the solvent is evaporated off under vacuum. 3.5 g of the expected product are obtained after crystallization from heptane and recrystallization from AcOEt. M.p.=213° C.

This compound can also be prepared according to Eur. J. Med. Chem.-Chimica Therapeutica, 1981, 16 (4), 321–326.
M.p.=206°–208° C.

Preparation 3

3-(1-Benzylpiperid-4-yl)-5-chloro-1,3-dihydro-2H-benzimidazol-2-one

A) 2-[(1-Benzylpiperid-4-yl)amino]-4-chloro-1-nitrobenzene

A solution of 38.4 g of 2,4-dichloro-1-nitrobenzene in 160 ml of 2-ethoxyethanol is heated to 100° C. A solution of 152.23 g of N-benzyl-4-aminopiperidine in 40 ml of 2-ethoxyethanol is then added slowly. The mixture is refluxed for 5 hours. The solvent is evaporated off under vacuum, the residue is taken up with H₂O, extracted with AcOEt, washed with water and dried over Na₂SO₄ and the solvent is evaporated off under vacuum. The residue is chromatographed on silica using isopropyl ether as the eluent to give 24.4 g of the expected product after crystallization from isopropyl ether. M.p.=84° C.

B) 1-Amino-2-[(1-benzylpiperid-4-yl)amino]-4-chlorobenzene

A mixture of 20.75 g of the compound obtained in step A) and 10 g of iron powder in 19 ml of water and 19 ml of ethanol is brought to the reflux point. A solution of 37.5 ml of concentrated hydrochloric acid in 25 ml of water and 25 ml of ethanol is added dropwise to this mixture and reflux is maintained for 1 hour 30 minutes. After cooling, the reaction mixture is poured onto ice and then treated with a saturated solution of NaHCO₃ and extracted with AcOEt. The extract is washed with water and dried over Na₂SO₄ and the solvent is evaporated off under vacuum. The residue is chromatographed on silica using a DCM/MeOH mixture (92/8; v/v) as the eluent. 12.71 g of the expected product are obtained after crystallization from isopropyl ether. M.p.=108° C.

C) 3-(1-Benzylpiperid-4-yl)-5-chloro-1,3-dihydro-2H-benzimidazol-2-one

A mixture of 12.71 g of the compound obtained in step B) and 8.9 g of 1,1'-carbonyldiimidazole in 130 ml of acetonitrile is refluxed for 3 hours. The solvent is evaporated off under vacuum, the residue is taken up with water, extracted with DCM, washed with a saturated solution of NaHCO₃ and with water and dried over Na₂SO₄ and the solvent is evaporated off under vacuum. The residue is chromatographed on silica using a DCM/MeOH mixture (92/8; v/v) as the eluent. 8.9 g of the expected product are obtained after recrystallization from absolute ethanol. M.p.=204°–206° C.

Preparation 4

5-Chloro-3-cyclohexylmethyl-1,3-dihydro-2H-benzimidazol-2-one

A) 4-Chloro-1-nitro-2-(cyclohexylmethyl)aminobenzene

A solution of 13.6 g of cyclohexylmethylamine in 10 ml of 95° ethanol is added dropwise to a solution of 8.1 g of 1,2-dinitro-4-chlorobenzene in 20 ml of 95° ethanol. The temperature rises to 50° C. The reaction medium is stirred for 2 hours and the solvent is then evaporated off under vacuum. The residue is taken up with DCM, washed with water, then with 2N hydrochloric acid and then with water and dried over Na₂SO₄ and the solvent is then evaporated off under vacuum. The residue is chromatographed on silica using isopropyl ether as the eluent. 4.21 g of the expected product are obtained after recrystallization from heptane. M.p.=73° C.

B) 4-Chloro-1-amino-2-(cyclohexylmethyl)aminobenzene

A solution of 21.5 g of the product obtained in step A) and 13.4 g of iron powder in a mixture of 25 ml of water and 25 ml of ethanol is brought to the reflux point. A solution of 50 ml of concentrated hydrochloric acid in a mixture of 34 ml of water and 34 ml of ethanol is then added slowly. Reflux is maintained for 2 hours. The reaction medium is then poured onto ice, treated with a saturated solution of NaHCO₃ and then extracted with DCM, washed with water and dried over Na₂SO₄ and the solvent is evaporated off under vacuum. The residue is chromatographed on silica using DCM as the eluent. 7.2 g of the expected product are obtained after crystallization from heptane. M.p.=62° C.

C) 5-Chloro-3-cyclohexylmethyl-1,3-dihydro-2H-benzimidazol-2-one

A mixture of 7.2 g of the compound obtained in step B) and 6.7 g of 1,1'-carbonyldiimidazole in 100 ml of acetonitrile is refluxed for 5 minutes. The solvent is evaporated off under vacuum, the residue is taken up with water, extracted with DCM, washed with a saturated solution of NaHCO₃ and dried over Na₂SO₄ and the solvent is evaporated off under vacuum. The residue is chromatographed on silica using a DCM/MeOH mixture (95/5; v/v) as the eluent to give 5.6 g of the expected product. M.p.=173° C.

Preparation 5

5-Chloro-3-cycloheptyl-1,3-dihydro-2H-benzimidazol-2-one

A) 4-Chloro-2-cycloheptylamino-1-nitrobenzene

A mixture of 18.2 g of 4-chloro-1,2-dinitrobenzene and 31 g of cycloheptylamine in 55 ml of 95° EtOH is stirred for 15 hours at RT. The reaction mixture is concentrated under vacuum, the residue is extracted with AcOEt, washed with a 1N solution of HCl and with water and dried over Na₂SO₄ and the solvent is evaporated off under vacuum. The residue is chromatographed on silica using petroleum ether as the eluent to give 13 g of the expected product after crystallization from isopropanol.

B) 1-Amino-4-chloro-2-cycloheptylaminobenzene

A mixture of 12.9 g of the compound obtained in the previous step and 8 g of iron powder in 15 ml of water and 15 ml of EtOH is heated to the reflux point. A solution of 30 ml of concentrated HCl in 20 ml of EtOH and 20 ml of water is then added dropwise and reflux is maintained for 1 hour 30 minutes. After cooling, the reaction mixture is filtered on Célite®, the material on the filter is washed with MeOH and the filtrate is concentrated under vacuum. The residue is taken up with ice, rendered alkaline by the addition of a saturated solution of NaHCO₃, extracted with DCM, washed with water and dried over Na₂SO₄ and the solvent is evaporated off under vacuum. The residue is chromatographed on silica using petroleum ether and then iso ether as the eluent to give 10 g of the expected product in the form of an oil, which is used as such in the next step.

C) 5-Chloro-3-cycloheptyl-1,3-dihydro-2H-benzimidazol-2-one

A mixture of 9.9 g of the compound obtained in the previous step and 9.3 g of 1,1'-carbonyldiimidazole in 150 ml of acetonitrile is refluxed for 10 minutes. The solvent is evaporated off under vacuum, the residue is taken up with a saturated solution of NaHCO₃, extracted with DCM, washed with water and dried over Na₂SO₄ and the solvent is evaporated off under vacuum. The residue is taken up with 100 ml of iso ether and the precipitate formed is filtered off. The precipitate is chromatographed on silica using DCM and then a DCM/AcOEt mixture (80/20; v/v) as the eluent to give 8.1 g of the expected product. M.p.=201° C.

Preparation 6

3-Cyclohexyl-5-ethoxy-1,3-dihydro-2H-benzimidazol-2-one

A) 4-Ethoxy-1-nitro-2-cyclohexylaminobenzene

A solution of sodium ethylate is prepared by adding 0.5 g of sodium to 60 ml of ethanol. 5.1 g of 4-chloro-2-cyclohexylamino-1-nitrobenzene, described in Preparation 2 step A), are then added. 7.5 ml of tris-[2-(2-methoxyethoxy)ethyl]amine are then added and the mixture is refluxed for 3 hours. The solvent is evaporated off under vacuum, the residue is taken up with water, extracted with DCM, washed with water and dried over $Na_2SO_4$ and the solvent is evaporated off under vacuum. After chromatography on silica using DCM as the eluent, 4.26 g of the expected product are obtained in the form of a yellow oil, which crystallized from iso ether. M.p.=80°–82° C.

B) 4-Ethoxy-1-amino-2-cyclohexylaminobenzene

A mixture of 4.26 g of the compound obtained in step A) and 2.7 g of iron powder in 5.1 ml of water and 5.1 ml of ethanol is brought to the reflux point. A solution of 10 ml of concentrated HCl in 7 ml of water and 7 ml of ethanol is then added dropwise and reflux is maintained for a further 2 hours. After cooling, the reaction mixture is poured onto ice, treated with a saturated solution of $NaHCO_3$ and extracted with DCM and a gray insoluble material is filtered off on Célite®. After decantation, the organic phase is washed with water and dried over $Na_2SO_4$ and the solvent is evaporated off under vacuum to give 3.05 g of a black oil, which was used as such in the next step.

C) 3-Cyclohexyl-5-ethoxy-1,3-dihydro-2H-benzimidazol-2-one

A mixture of 3.05 g of the oil obtained in step B) and 1.6 g of urea in 8 ml of 1,2,3,4-tetramethylbenzene is heated at 170°–180° C. for 1 hour 30 minutes. After cooling, it is taken up with AcOEt, washed with water and dried over sodium sulfate and the solvent is evaporated off under vacuum. The residue is taken up with hexane and the brown precipitate formed is filtered off. The precipitate is chromatographed on silica using a DCM/AcOEt mixture (50/50; v/v) as the eluent to give 1.33 g of the expected product, which was precipitated with isopropyl ether. M.p.=203° C.

Preparation 7

3-Cyclohexyl-1,3-dihydro-5-methoxy-2H-benzimidazol-2-one

A) 2-Cyclohexylamino-4-methoxy-1-nitrobenzene

A solution of sodium methylate is prepared by adding 0.5 g of sodium to 60 ml of MeOH. 5.1 g of the compound obtained in Preparation 2 step A) and 7.5 ml of tris[2-(2-methoxyethoxy)ethyl]amine are then added successively and the mixture is refluxed for 24 hours. The solvent is evaporated off under vacuum, the residue is taken up with water, extracted with DCM, washed with water and dried over $Na_2SO_4$ and the solvent is evaporated off under vacuum to give 3.86 g of the expected product in the form of an oil, which crystallizes. M.p.=78°–80° C.

B) 1-Amino-2-cyclohexylamino-4-methoxybenzene

A mixture of 11.86 g of the compound obtained in the previous step, 7.9 g of iron powder, 15 ml of water and 15 ml of EtOH is heated to the reflux point and a solution of 29.4 ml of concentrated hydrochloric acid in 20 ml of water and 20 ml of EtOH is then added dropwise. The reaction mixture is refluxed for 2 hours. After cooling, the reaction mixture is poured onto ice, a saturated solution of $NaHCO_3$ is added, the product is extracted with DCM and a gray insoluble material is filtered off on Célite ®. After decantation of the filtrate, the organic phase is washed with a saturated solution of $NaHCO_3$ and with water and dried over $Na_2SO_4$ and the solvent is evaporated off under vacuum. The residue is chromatographed on silica using a DCM/MeOH mixture (98/2; v/v) as the eluent to give 7.5 g of the expected product in the form of a black oil, which is used as such in the next step.

C) 3-Cyclohexyl-1,3-dihydro-5-methoxy-2H-benzimidazol-2-one

A mixture of 7.5 g of the compound obtained in the previous step and 4.1 g of urea in 20 ml of 1,2,3,4-tetramethylbenzene is heated at 170°–180° C. for 1 hour 30 minutes. After cooling, the product is extracted with AcOEt, washed with water and dried over $Na_2SO_4$ and the solvent is evaporated off under vacuum. The residue is taken up with hexane and the brown precipitate formed is filtered off. The precipitate is chromatographed on silica using a DCM/AcOEt mixture (50/50; v/v) as the eluent to give 2.76 g of the expected product after crystallization from AcOEt. M.p.=163°–165° C.

Preparation 8

5-Ethoxy-1,3-dihydro-3-(4(a,e)-methylcyclohexyl)-2H-benzimidazol-2-one

A) 4-Chloro-2-[(4(a,e)-methylcyclohexyl)amino]-1-nitrobenzene 30 g of 4-methylcyclohexylamine (mixture of isomers) are added dropwise to a solution of 20 g of 4-chloro-1,2-dinitrobenzene in 80 ml of 95° EtOH and the mixture is stirred for 24 hours at RT. The reaction mixture is evaporated under vacuum, the residue is extracted with heptane and the solvent is evaporated off under vacuum to give 25 g of the expected product in the form of a red oil, which is used as such in the next step.

B) 4-Ethoxy-2-[(4(a,e)-methylcyclohexyl)amino]-1-nitrobenzene

This compound is prepared by the procedure described in Preparation 6 step A) starting from 25 g of the compound obtained in the previous step. 14 g of the expected product are obtained. M.p.=85° C.

C) 1-Amino-4-ethoxy-2-[(4(a,e)-methylcyclohexyl)amino]benzene and 1-amino-4-ethoxy-2-[(4(a)-methylcyclohexyl)amino]benzene A mixture of 14 g of the compound obtained in the previous step and 0.8 g of 5% palladium-on-charcoal in 150 ml of 95° EtOH is hydrogenated at RT under a pressure of 2 bar. The catalyst is filtered off on Célite® and the filtrate is evaporated under vacuum. The residue is taken up with hot heptane and, after cooling, the solid formed is filtered off to give 6 g of the expected product in the form of a mixture of the axial and equatorial isomers. M.p. =92° C. The previous filtration liquors are concentrated under vacuum to give 3 g of the axial isomer of the expected product.

D) 4-Ethoxy-1-ethoxycarboxamido-2-[(4(a,e)-methylcyclohexyl)amino]benzene

A mixture of 5.8 g of the compound obtained in the previous step and 10 g of ethyl chloroformate in 100 ml of chloroform is refluxed for 1 hour. The solvent is evaporated off under vacuum and the residue is chromatographed on silica using DCM as the eluent to give 5 g of the expected product, which is used as such in the next step.

E) 5-Ethoxy-1,3-dihydro-3-(4(a,e)-methylcyclohexyl)-2H-benzimidazol-2-one 5 g of the compound obtained in the previous step are added to a solution of sodium ethylate, prepared by adding 0.75 g of sodium to 30 ml of absolute EtOH, and the mixture is refluxed for 6 hours. The reaction mixture is evaporated under vacuum, the residue is extracted with DCM, washed with water and dried over $Na_2SO_4$ and the solvent is evaporated off under vacuum to give 3 g of the expected product after crystallization from iso ether. M.p.=190° C.

Preparation 9

5-Ethoxy-1,3-dihydro-3-(4(a)-methylcyclohexyl)-2H-benzimidazol-2-one, axial isomer A) 4-Ethoxy-1-ethoxycarboxamido-2-[(4(a)-methylcyclohexyl)amino]benzene This compound is prepared by the procedure described in Preparation 8 step D) starting from 3 g of the axial isomer of the compound obtained in Preparation 8 step C). It is chromatographed on silica using a DCM/AcOEt mixture (90/10; v/v) as the eluent to give 2.8 g of the expected product after crystallization from iso ether. M.p. =183° C.

B) 5-Ethoxy-1,3-dihydro-3-(4(a)-methylcyclohexyl)-2H-benzimidazol-2-one, axial isomer This compound is prepared by the procedure described in Preparation 8 step E) starting from 2.8 g of the compound obtained in the previous step. 1.3 g of the expected product are obtained after crystallization from iso ether. M.p.=170° C.

Preparation 10

5-Ethoxy-1,3-dihydro-3-(4(a,e)-methoxycyclohexyl)-2H-benzimidazol-2-one

A) 4(a,e)-Methoxycyclohexylamine

A mixture of 100 g of 4-methoxyaniline and 48 g of 5% palladium-on-charcoal in 400 ml of AcOH is hydrogenated for 3 hours at a temperature of 75°–80° C. under a pressure of 45 bar. The catalyst is filtered off, 20 ml of water are added to the filtrate and the filtrate is evaporated under vacuum. The residue is taken up with 100 ml of water, cooled to 0° C., rendered alkaline by the addition of concentrated NaOH, extracted with ether and dried over $Na_2SO_4$ and the solvent is evaporated off at atmospheric pressure. The oil obtained is distilled at atmospheric pressure to give 31 g of the expected product in the form of an oil. B.p.=183°–188° C.

B) 4-Chloro-2-[(4(a,e)-methoxycyclohexyl)amino]-1-nitrobenzene

A mixture of 12 g of 4-chloro-1,2-dinitrobenzene and 7 g of the compound obtained in the previous step in 30 ml of EtOH is stirred for 15 hours. The solvent is evaporated off under vacuum, the residue is extracted with ether, washed with water, with a 1N solution of NaOH, with a 1N solution of HCl and with water and dried over $Na_2SO_4$ and the solvent is evaporated off under vacuum. The residue is chromatographed on silica using DCM as the eluent to give 6.6 g of the expected product in the form of an oil, which is used as such in the next step.

C) 4-Ethoxy-2-[(4(a,e)-methoxycyclohexyl)amino]-1-nitrobenzene

This compound is prepared by the procedure described in Preparation 6 step A) starting from 15.4 g of the compound obtained in the previous step. 12 g of the expected product are obtained after crystallization from iso ether. M.p.=93° C.

D) 1-Amino-4-ethoxy-2-[(4(a,e)-methoxycyclohexyl)amino]benzene

A mixture of 10 g of the compound obtained in the previous step and 3 g of 5% palladium-on-charcoal in 100 ml of EtOH is hydrogenated for 4 hours at RT and at atmospheric pressure. The catalyst is filtered off and the filtrate is evaporated under vacuum to give 8.5 g of the expected product in the form of a red oil, which is used as such in the next step.

E) 4-Ethoxy-1-ethoxycarboxamido-2-[(4(a,e)methoxycyclohexyl)amino]benzene

A solution of 8.4 g of the compound obtained in the previous step and 13 g of triethylamine in 100 ml of DCM is cooled to 10° C. and a solution of 5 ml of ethyl chloroformate in 15 ml of THF is added dropwise. The mixture is stirred for 3 hours, the temperature being allowed to rise to RT, and the solvents are evaporated off under vacuum. The residue is extracted with iso ether, washed with water and with a 10% solution of $Na_2CO_3$ and dried over $Na_2SO_4$ and the solvent is evaporated off under vacuum to give 12 g of the expected product, which is used as such in the next step.

F) 5-Ethoxy-1,3-dihydro-3-(4(a,e)-methoxycyclohexyl)-2H-benzimidazol-2-one

A mixture of 12 g of the compound obtained in the previous step and 4.1 g of sodium ethylate in 150 ml of THF is refluxed for 4 hours. The reaction mixture is evaporated under vacuum, the residue is dissolved in 50 ml of water and acidified to pH 1 by the addition of 2N HCl and the precipitate formed is filtered off and washed with water. The precipitate is chromatographed on silica using DCM and then a DCM/ AcOEt mixture (70/30; v/v) as the eluent to give 7.8 g of the expected product. M.p.=201° C.

Preparation 11

5-Ethoxy-1,3-dihydro-3-[4(a,e)-(2-methoxyethoxy)cyclohexyl]-2H-benzimidazol-2-one A) 4-(2-Methoxyethoxy)-1-nitrobenzene A mixture of 40 g of 4-nitrophenol, 41 g of 1-bromo-2-methoxyethane, 45 g of $K_2CO_3$ and 80 ml of tris[2-(2-methoxyethoxy)ethyl]amine in 80 ml of acetone is refluxed for 20 hours. An insoluble material is filtered off and the filtrate is concentrated under vacuum. The residue is taken up with water and the precipitate formed is filtered off and washed with water. The precipitate is dissolved in AcOEt, washed with a 1N solution of NaOH, with water, with a 1N solution of HCl and with water and dried over $Na_2SO_4$ and the solvent is evaporated off under vacuum to give 59 g of the expected product, which is used as such in the next step.

B) 4-(2-Methoxyethoxy)aniline

A mixture of 59 g of the compound obtained in the previous step and 6 g of 5% palladium-on-charcoal in 400 ml of EtOH is hydrogenated for 5 hours at 40° C. and at atmospheric pressure. The catalyst is filtered off and the filtrate is evaporated under vacuum to give 43 g of the expected product, which is used as such in the next step.

C) 4(a,e)-(2-Methoxyethoxy)cyclohexylamine

This compound is prepared by the procedure described in Preparation 10 step A) starting from 43 g of the compound obtained in the previous step. The oil obtained is distilled under reduced pressure to give 19 g of the expected product in the form of an oil. B.p.=123°–127° C. under 15 mm Hg.

D) 4-Chloro-2-[[4(a,e)-(2-methoxyethoxy)cyclohexyl]amino]-1-nitrobenzene

A mixture of 19 g of the compound obtained in the previous step, 22.2 g of 4-chloro-1,2-dinitrobenzene and 20 ml of triethylamine in 30 ml of EtOH is stirred for 15 hours at RT. The reaction mixture is evaporated under vacuum, the residue is taken up with water, extracted with ether, washed with a 1N solution of HCl, with water, with a 1N solution of NaOH and with water and dried over $Na_2SO_4$ and the solvent is evaporated off under vacuum. The residue is chromatographed on silica using iso ether and then DCM as the eluent to give 20 g of the expected product in the form of an orange oil, which is used as such in the next step.

E) 4-Ethoxy-2-[[4(a,e)-(2-methoxyethoxy)cyclohexyl]amino]-1-nitrobenzene

A solution of sodium ethylate is prepared by adding 1.8 g of sodium to 50 ml of EtOH. 19.9 g of the compound obtained in the previous step, 30 ml of tris[2-(2-methoxyethoxy)ethyl]amine and 80 ml of EtOH are then added and the mixture is refluxed for 5 hours. The reaction mixture is evaporated under vacuum, the residue is taken up with a 2N solution of HCl, extracted with ether, washed with water and dried over $Na_2SO_4$ and the solvent is evaporated off under vacuum to give 17.5 g of the expected product, which is used as such in the next step.

F) 5-Ethoxy-1,3-dihydro-3-[4(a,e)-(2-methoxyethoxy)cyclohexyl]-2H-benzimidazol-2-one This compound is prepared by the procedures described in Preparation 10 steps D), E) and then F) starting from 17.4 g of the compound obtained in the previous step. 11.5 g of the expected product are obtained. M.p.=118°–120° C.

Preparation 12

5-Ethoxy-1,3-dihydro-3-(2-methoxy-1,1-dimethylethyl)-2H-benzimidazol-2-one

A) 4-Chloro-2-[(2-hydroxy-1,1-dimethylethyl)amino]-1-nitrobenzene

A mixture of 20 g of 4-chloro-1,2-dinitrobenzene and 36 g of 2-amino-2-methylpropan-1-ol in 100 ml of EtOH is refluxed for 36 hours. The reaction mixture is evaporated under vacuum, the residue is extracted with AcOEt, washed with a 1N solution of HCl and with water and dried over $Na_2SO_4$ and the solvent is evaporated off under vacuum. The residue is chromatographed on silica using DCM as the eluent to give 16 g of the expected product, which is used as such in the next step.

B) 4-Chloro-2-[(2-methoxy-1,1-dimethylethyl)amino]-1-nitrobenzene 1.6 g of sodium hydride are added in portions to a solution of 15 g of the compound obtained in the previous step in 200 ml of THF and the mixture is stirred for 30 minutes at RT. 6 ml of methyl iodide are then added and the mixture is stirred for 2 hours at RT. The solvent is evaporated off under vacuum, the residue is taken up with 300 ml of water, extracted with AcOEt and dried over $Na_2SO_4$ and the solvent is evaporated off under vacuum. The residue is chromatographed on silica using DCM as the eluent to give 12.5 g of the expected product, which is used as such in the next step.

C) 4-Ethoxy-2-[(2-methoxy-1,1-dimethylethyl)amino]-1-nitrobenzene

A solution of sodium ethylate is prepared by adding 2 g of sodium to 100 ml of EtOH. 12.5 g of the compound obtained in the previous step are then added and the mixture is refluxed for 5 hours. The reaction mixture is concentrated under vacuum, the residue is taken up with 300 ml of water, extracted with AcOEt and dried over $Na_2SO_4$ and the solvent is evaporated off under vacuum to give 12 g of the expected product, which is used as such in the next step.

D) 1-Amino-4-ethoxy-2-[(2-methoxy-1,1-dimethylethyl)amino]benzene

A mixture of 12 g of the compound obtained in the previous step and 1.2 g of 5% palladium-on-charcoal in 250 ml of AcOEt is hydrogenated for 24 hours at 40° C. and at atmospheric pressure. The catalyst is filtered off on Célite® and the filtrate is evaporated under vacuum to give 12 g of the expected product, which is used as such in the next step.

E) 4-Ethoxy-1-ethoxycarboxamido-2-[(2-methoxy-1,1-dimethylethyl)amino]benzene

A mixture of 12 g of the compound obtained in the previous step and 14 g of ethyl chloroformate in 200 ml of chloroform is refluxed for 2 hours. After cooling, it is washed with a 1N solution of NaOH and dried over $Na_2SO_4$ and the solvent is evaporated off under vacuum. The residue is chromatographed on silica using a DCM/MeOH mixture (99/1; v/v) as the eluent to give 8.4 g of the expected product. M.p.=138° C.

F) 5-Ethoxy-1,3-dihydro-3-(2-methoxy-1,1-dimethylethyl)-2H-benzimidazol-2-one

This compound is prepared by the procedure described in Preparation 8 step E) starting from 8.4 g of the compound obtained in the previous step. 4.9 g of the expected product are obtained after crystallization from EtOH. M.p.=149° C.

Preparation 13

5-Ethoxy-1,3-dihydro-3-(1,1,3,3-tetramethylbutyl)-2H-benzimidazol-2-one

A) 4-Chloro-2-[(1,1,3,3-tetramethylbutyl)amino]-1-nitrobenzene

A mixture of 20 g of 4-chloro-1,2-dinitrobenzene and 30 g of tert-octylamine in 300 ml of 95° EtOH is refluxed for 16 hours. The solvent is evaporated off under vacuum to give 13 g of the expected product after crystallization from an iso ether/heptane mixture (40/60; v/v). M.p.=108° C.

B) 4-Ethoxy-2-[(1,1,3,3-tetramethylbutyl)amino]-1-nitrobenzene

This compound is prepared by the procedure described in Preparation 12 step C) starting from 18 g of the compound obtained in the previous step. It is chromatographed on silica using heptane as the eluent to give 4 g of the expected product, which is used as such in the next step.

C) 1-Amino-4-ethoxy-2-[(1,1,3,3-tetramethylbutyl)amino]benzene

A mixture of 4 g of the compound obtained in the previous step and 0.2 g of 5% palladium-on-charcoal in 150 ml of AcOEt is hydrogenated at RT and at atmospheric pressure. The catalyst is filtered off on Célite® and the filtrate is evaporated under vacuum to give 3.6 g of the expected product, which is used as such in the next step.

D) 4-Ethoxy-1-ethoxycarboxamido-2-[(1,1,3,3-tetramethylbutyl)amino]benzene

A mixture of 3.6 g of the compound obtained in the previous step, 2 ml of ethyl chloroformate and 2 ml of triethylamine in 100 ml of chloroform is stirred for 1 hour. It is washed with a 1N solution of NaOH, with water, with a 1 N solution of HCl and with water and dried over $Na_2SO_4$ and the solvent is evaporated off under vacuum to give 4 g of the expected product, which is used as such in the next step.

E) 5-Ethoxy-1,3-dihydro-3-(1,1,3,3-tetramethylbutyl)-2H-benzimidazol-2-one

A solution of sodium ethylate is prepared from 0.6 g of sodium and 100 ml of EtOH. 4 g of the compound obtained in the previous step are added and the mixture is refluxed for 3 hours. The solvent is evaporated off under vacuum, the residue is taken up with 100 ml of water and the precipitate formed is filtered off and washed with water and then with iso ether to give 2.6 g of the expected product after drying. M.p.=157° C.

Preparation 14

3-(2-Chlorophenyl)-5-ethoxy-1,3-dihydro-2H-benzimidazol-2-one

A) 4-Chloro-2-[(2-chlorophenyl)amino]-1-nitrobenzene

A mixture of 101 g of 4-chloro-1,2-dinitrobenzene and 191 g of 2-chloroaniline in 750 ml of 95° EtOH is refluxed for 96 hours. The solvent is evaporated off under vacuum, the residue is extracted with DCM, washed with a 3 N solution of HCl and with water and dried over $Na_2SO_4$ and the solvent is evaporated off under vacuum. The residue is chromatographed on silica using a DCM/hexane mixture (50/50; v/v) as the eluent to give 7 g of the expected product after crystallization from EtOH. M.p.=97° C.

B) 2-[(2-Chlorophenyl)amino]-4-ethoxy-1-nitrobenzene

This compound is prepared by the procedure described in Preparation 6 step A) starting from 7 g of the compound obtained in the previous step. 3.3 g of the expected product are obtained after crystallization from iso ether.

C) 1-Amino-2-[(2-chlorophenyl)amino]-4-ethoxybenzene

A mixture of 3.3 g of the compound obtained in the previous step and 2 g of iron powder in 3 ml of water and 3 ml of EtOH is heated to the reflux point and a solution of 0.17 ml of concentrated HCl in 0.7 ml of water and 0.7 ml of EtOH is then added dropwise. The mixture is refluxed for two hours and then, after cooling, rendered alkaline by the addition of concentrated NaOH, the reaction mixture is filtered on Célite® and the material on the filter is washed copiously with AcOEt. After decantation of the filtrate, the organic phase is dried over $Na_2SO_4$ and the solvent is evaporated off under vacuum. The residue is chromatographed on silica using a DCM/AcOEt mixture (90/10; v/v) as the eluent to give 1.75 g of the expected product, which is used as such in the next step.

D)  2-[(2-Chlorophenyl)amino]-4-ethoxy-1-methoxycarboxamidobenzene

A mixture of 1.75 g of the compound obtained in the previous step and 3 g of methyl chloroformate in 30 ml of chloroform is refluxed for 3 hours. The solvent is evaporated off under vacuum, the residue is extracted with DCM, washed with water and dried over $Na_2SO_4$ and the solvent is evaporated off under vacuum to give 1.2 g of the expected product, which is used as such in the next step.

E) 3-(2-Chlorophenyl)-5-ethoxy-1,3-dihydro-2H-benzimidazol2-one

This compound is prepared by the procedure described in Preparation 8 step E) starting from 1.2 g of the compound obtained in the previous step. After evaporation of the reaction mixture under vacuum, the residue is taken up with AcOEt and washed with water and the product precipitates. The precipitate is filtered off to give 1 g of the expected product after drying. M.p.=213° C.

Preparation 15

5-Ethoxy-3-(tetrahydropyran-4-yl)-1,3-dihydro-2H-benzimidazol-2-one

A) Tetrahydro-4H-pyran-4-one oxime

A solution of 29 g of hydroxylamine hydrochloride in 90 ml of EtOH is added to a solution of 35 g of tetrahydro-4H-pyran-4-one in 225 ml of pyridine and the mixture is stirred for 48 hours at RT. The reaction mixture is concentrated to 50 ml, 500 ml of iced water are added, the resulting mixture is extracted 6 times with AcOEt and dried over $Na_2SO_4$ and the solvent is evaporated off under vacuum to give 26 g of the expected product. M.p.=94° C.

B) 4-Aminotetrahydropyran

A mixture of 32 g of the compound obtained in the previous step and 300 ml of EtOH is hydrogenated for 3 hours at 60° C. under a pressure of 20 bar in the presence of Raney® nickel. The catalyst is filtered off, the solvent is evaporated off under vacuum and the oil obtained is distilled at atmospheric pressure to give 18 g of the expected product. B.p.=150°–175° C.

C)  4-Chloro-1-nitro-2-[(tetrahydropyran-4-yl)amino]benzene

A mixture of 33 g of 4-chloro-1,2-dinitrobenzene, 18 g of the compound obtained in the previous step and 22 g of triethylamine in 250 ml of 96° EtOH is heated at 60° C. for 48 hours. After cooling, the precipitate formed is filtered off and washed with EtOH and then with iso ether to give 24.4 g of the expected product. M.p.=155° C.

D)  4-Ethoxy-1-nitro-2-[(tetrahydropyran-4-yl)amino]benzene

This compound is prepared by the procedure described in Preparation 12 step C) starting from 24.4 g of the compound obtained in the previous step. 21.4 g of the expected product are obtained after crystallization from iso ether. M.p.=117° C.

E) 1-Amino-4-ethoxy-2-[(tetrahydropyran-4-yl)amino]benzene

A mixture of 21.4 g of the compound obtained in the previous step and 2 g of 5% palladium-on-charcoal in 500 ml of AcOEt is hydrogenated at 40° C. and at atmospheric pressure. The catalyst is filtered off on Célite® and the filtrate is evaporated under vacuum to give 18 g of the expected product. M.p.=101° C.

F)  4-Ethoxy-2-[(tetrahydropyran-4-yl)amino]-1-methoxycarboxamidobenzene 30 ml of methyl chloroformate are added dropwise to a solution of 19 g of the compound obtained in the previous step and 15 ml of triethylamine in 500 ml of chloroform and the mixture is stirred for 3 hours at RT. It is washed with a 1N solution of HCl and with a 1N solution of NaOH and dried over $Na_2SO_4$ and the solvent is evaporated off under vacuum to give 13.8 g of the expected product after crystallization from an iso ether/EtOH mixture (80/20; v/v). M.p.=185° C.

G) 5-Ethoxy-3-(tetrahydropyran-4-yl)-1,3-dihydro-2H-benzimidazol-2-one

A mixture of 13.8 g of the compound obtained in the previous step with a solution of sodium ethylate, prepared from 3.5 g of sodium and 300 ml of EtOH, is refluxed for 3 hours. The solvent is evaporated off under vacuum, the residue is taken up with water and the precipitate formed is filtered off and washed with AcOEt to give 8.4 g of the expected product. M.p.=222° C.

Preparation 16

3-Cyclohexyl-5-cyclopentoxy-1,3-dihydro-2H-benzimidazol-2-one

A) 2-Cyclohexylamino-4-cyclopentoxy-1-nitrobenzene

A solution of sodium cyclopentylate, prepared from 0.9 g of sodium and 150 ml of cyclopentanol, is heated to 50° C., 10 g of the compound obtained in Preparation 2 step A) and 12 ml of tris[2-(2-methoxyethoxy)ethyl]amine are added and the mixture is then heated at 100° C. for 30 hours. The cyclopentanol is distilled off under vacuum, the residue is taken up with water, extracted with AcOEt, washed with water and dried over $Na_2SO_4$ and the solvent is evaporated off under vacuum. The residue is chromatographed on silica using heptane as the eluent to give 4.7 g of the expected product. M.p.=98° C.

B) 1-Amino-2-cyclohexylamino-4-cyclopentoxybenzene

A mixture of 4.7 g of the compound obtained in the previous step and 0.3 g of 5% palladium-on-charcoal in 120 ml of 95° EtOH is hydrogenated for 3 hours at RT under a pressure of 2 bar. The catalyst is filtered off on Célite® and the filtrate is evaporated under vacuum to give 4 g of the expected product. M.p.=80° C.

C)  2-Cyclohexylamino-4-cyclopentoxy-1-ethoxycarboxamidobenzene

A mixture of 4 g of the compound obtained in the previous step and 6 g of ethyl chloroformate in 50 ml of chloroform is refluxed for 2 hours. The reaction mixture is washed with water and dried over $Na_2SO_4$ and the solvent is evaporated off under vacuum. The residue is chromatographed on silica using a DCM/AcOEt mixture (75/25; v/v) as the eluent to give 2.6 g of the expected product after crystallization from iso ether. M.p.=202° C.

D) 3-Cyclohexyl-5-cyclopentoxy-1,3-dihydro-2H-benzimidazol-2-one 2.5 g of the compound obtained in the previous step are added to a solution of sodium ethylate, prepared from 0.2 g of sodium and 50 ml of EtOH, and the mixture is refluxed for 18 hours. The solvent is evaporated off under vacuum, the residue is extracted with AcOEt, washed with water and dried over $Na_2SO_4$ and the solvent is evaporated off under vacuum to give 1.7 g of the expected product after crystallization from iso ether. M.p.=242° C.

Preparation 17

3-Cyclohexyl-1,3-dihydro-5-(2-methoxyethoxy)-2H-benzimidazol-2-one

A)  2-Cyclohexylamino-4-(2-methoxyethoxy)-1-nitrobenzene 10 g of the compound obtained in Preparation 2 step A) and 12 ml of tris[2-(2-methoxyethoxy)ethyl]amine are added to a solution of sodium 2-methoxyethylate, prepared from 0.9 g of sodium and 100 ml of 2-methoxyethanol, and the mixture is then refluxed for 5 hours. The reaction mixture is evaporated under vacuum, the residue is extracted with AcOEt, washed with water and dried over $Na_2SO_4$ and the solvent is evaporated off under vacuum. The residue is chromatographed on silica using a DCM/heptane mixture (50/50; v/v) as the eluent to give 7 g of the expected product, which is used as such in the next step.

B) 1-Amino-2-cyclohexylamino-4-(2-methoxyethoxy)benzene

A mixture of 7 g of the compound obtained in the previous step and 0.5 g of 5% palladium-on-charcoal in 200 ml of 95° EtOH is hydrogenated at RT under a pressure of 2 bar. The catalyst is filtered off on Célite® and the filtrate is evaporated under vacuum to give 5 g of the expected product, which is used as such in the next step.

C) 2-Cyclohexylamino-1-ethoxycarboxamido-4-(2-methoxyethoxy)benzene

A mixture of 5 g of the compound obtained in the previous step and 6 g of ethyl chloroformate in 50 ml of chloroform is refluxed for 3 hours. The solvent is evaporated off under vacuum and the residue is chromatographed on silica using DCM as the eluent to give 6 g of the expected product. M.p.=145° C.

D) 3-Cyclohexyl-1,3-dihydro-5-(2-methoxyethoxy)-2H-benzimidazol-2-one 6 g of the compound obtained in the previous step are added to a solution of sodium ethylate, prepared from 0.45 g of sodium and 100 ml of EtOH, and the mixture is refluxed for 25 hours. The solvent is evaporated off under vacuum, the residue is extracted with AcOEt, washed with water and dried over $Na_2SO_4$ and the solvent is evaporated off under vacuum to give 2.2 g of the expected product after crystallization from iso ether. M.p.=182° C.

Preparation 18

5-Chloro-3-(3-chlorophenyl)-1,3-dihydro-2H-benzimidazol-2-one

A) 4-Chloro-2-[(3-chlorophenyl)amino]-1-nitrobenzene

A mixture of 50 g of 2,4-dichloro-1-nitrobenzene, 40 ml of 3-chloroaniline and 43 g of anhydrous sodium acetate in 220 ml of ethylene glycol is refluxed for 72 hours. After cooling, the precipitate formed is filtered off and washed with water to give 39 g of the expected product after crystallization from iso ether. M.p.=112° C.

B) 1-Amino-4-chloro-2-[(3-chlorophenyl)amino]benzene 64 g of tin powder are added in portions to a mixture of 38 g of the compound obtained in the previous step, 140 ml of concentrated HCl and 390 ml of EtOH, the temperature being kept below 50° C. The reaction mixture is stirred for 1 hour and filtered on Célite® and the filtrate is evaporated under vacuum. The residue is extracted with DCM, washed with water and dried over $Na_2SO_4$ and the solvent is evaporated off under vacuum to give 38 g of the expected product. M.p.=82° C.

C) 4-Chloro-2-[(3-chlorophenyl)amino]-1-ethoxycarboxamidobenzene 6.8 ml of ethyl chloroformate are added slowly to a mixture of 18 g of the compound obtained in the previous step and 10 g of potassium carbonate in 160 ml of DMF and 55 ml of water, the temperature being kept at 20° C. The reaction mixture is stirred for 1 hour, 300 ml of water are added, the mixture is extracted with DCM, washed with water and dried over $Na_2SO_4$ and the solvent is evaporated off under vacuum. The residue is chromatographed on silica using a cyclohexane/DCM mixture (80/20; v/v) as the eluent to give 19 g of the expected product. M.p.=96° C.

D) 5-Chloro-3-(3-chlorophenyl)-1,3-dihydro-2H-benzimidazol-2-one 18 g of the compound obtained in the previous step are added to a solution of sodium ethylate, prepared from 2.6 g of sodium and 100 ml of EtOH, and the mixture is heated at 60° C. for 1 hour. The solvent is evaporated off under vacuum, the residue is taken up with 200 ml of water and acidified to pH 1 by the addition of concentrated HCl and the precipitate formed is filtered off to give 12.6 g of the expected product. M.p.=245° C.

Preparation 19

5-Ethoxy-1,3-dihydro-3-[4(a,e)-(tetrahydropyran-2(R,S)-yloxy)cyclohexyl]-2H-benzimidazol-2-one A) 4-Chloro-2-[(4(a,e)-hydroxycyclohexyl)amino]-1-nitrobenzene A mixture of 19.8 g of 4-chloro-1,2-dinitrobenzene and 45 g of 4-aminocyclohexanol (mixture of isomers) in 75 ml of EtOH is stirred for 15 hours at RT. The reaction mixture is evaporated under vacuum, the residue is extracted with ether, washed with a 1N solution of HCl and with water and dried over $Na_2SO_4$ and the solvent is evaporated off under vacuum. The residue is chromatographed on silica using iso ether as the eluent to give 14.8 g of the expected product in the form of an oil, which is used as such in the next step.

B) 4-Chloro-2-[[4(a,e)-(tetrahydropyran-2(R,S)-yloxy)cyclohexyl]amino]-1-nitrobenzene A mixture of 15.5 g of the compound obtained in the previous step, 10.5 g of 3,4-dihydro-2H-pyran and 0.1 g of paratoluenesulfonic acid in 250 ml of ether is stirred for 20 hours at RT. The solvent is evaporated off under vacuum to give 23 g of the expected product in the form of an oil, which is used as such in the next step.

C) 4-Ethoxy-2-[[4(a,e)-(tetrahydropyran-2(R,S)-yloxy)cyclohexyl]amino]-1-nitrobenzene 21 g of the compound obtained in the previous step and 10 ml of tris[2-(2-methoxyethoxy)ethyl]amine are added to a solution of sodium ethylate, prepared from 1.8 g of sodium and 30 ml of EtOH, and the mixture is refluxed for 5 hours. The reaction mixture is evaporated under vacuum, the residue is taken up with water, cooled to 0° C., acidified to pH 1 by the addition of 1N HCl, extracted rapidly with ether, washed with water and dried over $Na_2SO_4$ and the solvent is evaporated off under vacuum to give 23 g of the expected product in the form of an oil, which is used as such in the next step.

D) 1-Amino-4-ethoxy-2-[[4(a,e)-(tetrahydropyran-2(R,S)-yloxy)cyclohexyl]amino]benzene A mixture of 23 g of the product obtained in the previous step, 3 g of 5% palladium-on-charcoal and 90 ml of EtOH is hydrogenated for 6 hours at 35°–40° C. and at atmospheric pressure. The catalyst is filtered off and the filtrate is evaporated under vacuum to give 20 g of the expected product in the form of an oil, which is used as such in the next step.

E) 4-Ethoxy-1-ethoxycarboxamido-2-[[4(a,e)(tetrahydropyran-2(R,S)-yloxy)cyclohexyl]amino]benzene A mixture of 19.9 g of the compound obtained in the previous step and 27 g of triethylamine in 150 ml of DCM is cooled to 5° C., a solution of 6.5 ml of ethyl chloroformate in 25 ml of THF is added dropwise and the mixture is stirred for 3 hours, the temperature being allowed to rise to RT. The reaction mixture is evaporated under vacuum, the residue is extracted with ether, washed with water and dried over $Na_2SO_4$ and the solvent is evaporated off under vacuum. The residue is chromatographed on alumina using iso ether as the eluent and the product obtained is then rechromatographed on silica using iso ether and then DCM as the eluent to give 4 g of the expected product in the form of an oil, which is used as such in the next step.

F) 5-Ethoxy-1,3-dihydro-3-[4(a,e)-(tetrahydropyran-2(R, S)yloxy)cyclohexyl]-2H-benzimidazol-2-one 4 g of the compound obtained in the previous step are added to a solution of sodium ethylate, prepared from 0.3 g of sodium and 50 ml of EtOH, and the mixture is refluxed for 3 hours. The reaction mixture is evaporated under vacuum, the residue is extracted with AcOEt, washed with water and dried over $Na_2SO_4$ and the solvent is evaporated off under vacuum to give 1.5 g of the expected product after crystallization from iso ether. M.p.=135°–145° C.

Preparation 20

5-Ethoxy-1,3-dihydro-3-[2-(N,N-diisopropylamino)ethyl]-2H-benzimidazol-2-one

A) 4-Chloro-2-[N-[2-(N',N'-diisopropylamino)ethyl]amino]-1-nitrobenzene 39 g of N,N-diisopropylethylenediamine are added to a solution of 19.5 g of 4-chloro-1,2-dinitrobenzene in 150 ml of EtOH. The temperature rises to 50° C. The reaction medium is stirred for 3 hours and the solvent is then evaporated off under vacuum. The residue is taken up with 200 ml of isopropanol, cooled to 0° C. and left to stand at this temperature and the precipitate formed is then filtered off to give 12 g of the expected product after recrystallization from isopropanol.

B) 4-Ethoxy-2-[N-[2-(N',N'-diisopropylamino)ethyl]amino]-1-nitrobenzene

This compound is prepared by the procedure described in Preparation 6 step A) starting from 11.3 g of the compound obtained in the previous step. It is chromatographed on silica using a DCM/MeOH mixture (97/3; v/v) as the eluent to give 6.7 g of the expected product after crystallization from heptane. M.p.=89° C.

C) 1-Amino-4-ethoxy-2-[N-[2-(N',N'-diisopropylamino)ethyl]amino]benzene

A mixture of 6.7 g of the compound obtained in the previous step and 0.55 g of 5% palladium-on-charcoal in 550 ml of EtOH is hydrogenated for 8 hours at RT and at atmospheric pressure. The catalyst is filtered off on CE'LITE® and the filtrate is evaporated under vacuum to give 5.8 g of the expected product, which is used as such in the next step.

D) 4-Ethoxy-1-ethoxycarboxamido-2-[N-ethoxycarbonyl-N-[2-(N',N'-diisopropylamino)ethyl]amino]benzene 5.5 ml of ethyl chloroformate are added dropwise to a solution of 5.8 g of the compound obtained in the previous step in 25 ml of chloroform and the mixture is refluxed for 20 hours. The solvent is evaporated off under vacuum, the residue is taken up with a saturated solution of $NaHCO_3$, extracted with DCM and dried over $Na_2SO_4$ and the solvent is evaporated off under vacuum. The residue is chromatographed on silica using a DCM/MeOH mixture (95/5; v/v) as the eluent to give 5.9 g of the expected product, which is used as such in the next step.

E) 5-Ethoxy-1,3-dihydro-3-[2-(N,N-diisopropylamino)ethyl]-2H-benzimidazol-2-one 5.9 g of the compound obtained in the previous step are added to a solution of sodium ethylate, prepared from 0.8 g of sodium and 35 ml of EtOH, and the mixture is refluxed for 3 hours. The solvent is evaporated off under vacuum, the residue is taken up with water, extracted with DCM and dried over $Na_2SO_4$ and the solvent is evaporated off under vacuum. The residue is taken up with iso ether and the precipitate formed is filtered off to give 2.4 g of the expected product. M.p.=120° C.

Preparation 21

5-Ethoxy-1,3-dihydro-3-[2-(morpholin-4-yl)ethyl]-2H-benzimidazol-2-one

A) 4-Chloro-2-[N-[2-(morpholin-4-yl)ethyl]amino]-1-nitrobenzene

A mixture of 19.5 g of 4-chloro-1,2-dinitrobenzene and 35 g of 4-(2-aminoethyl)morpholine in 180 ml of EtOH is stirred for 20 hours at RT. The precipitate formed is filtered off and washed with iso ether to give 17.1 g of the expected product after crystallization twice in succession from isopropanol.

B) 4-Ethoxy-2-[N-[2-(morpholin-4-yl)ethyl]amino]-1-nitrobenzene

This compound is prepared by the procedure described in Preparation 6 step A) starting from 8.6 g of the compound obtained in the previous step. It is chromatographed on silica using a DCM/MeOH mixture (99/1; v/v) as the eluent to give 4.3 g of the expected product. M.p.=107° C.

C) 1-Amino-4-ethoxy-2-[N-[2-(morpholin-4-yl)ethyl]amino]-1-nitrobenzene

A mixture of 4.3 g of the compound obtained in the previous step and 0.4 g of 5% palladium-on-charcoal in 400 ml of EtOH is hydrogenated for 1 hour at RT and at atmospheric pressure. The catalyst is filtered off on C élite® and the filtrate is evaporated under vacuum. The residue is chromatographed on silica using a DCM/ MeOH mixture (95/5; v/v) as the eluent to give 3.7 g of the expected product in the form of an oil, which is used as such in the next step.

D) 4-Ethoxy-1-ethoxycarboxamido-2-[N-[2-(morpholin-4-yl)ethyl]amino]benzene 3 ml of ethyl chloroformate are added dropwise at RT to a solution of 3.7 g of the compound obtained in the previous step in 20 ml of chloroform and the mixture is refluxed for 4 hours. The solvent is evaporated off under vacuum, the residue is taken up with a saturated solution of $NaHCO_3$, extracted with DCM and dried over $Na_2SO_4$ and the solvent is evaporated off under vacuum to give 4.5 g of the expected product, which is used as such in the next step.

E) 5-Ethoxy-1,3-dihydro-3-[2-(morpholin-4-yl)ethyl]-2H-benzimidazol-2-one 4.5 g of the compound obtained in the previous step are added to a solution of sodium ethylate, prepared from 0.6 g of sodium and 25 ml of EtOH, and the mixture is refluxed for 3 hours. The solvent is evaporated off under vacuum, the residue is taken up with water, extracted with DCM and dried over $Na_2SO_4$ and the solvent is evaporated off under vacuum. The residue is chromatographed on silica using a DCM/MeOH mixture (95/5; v/v) as the eluent. The product obtained is taken up with iso ether and the precipitate formed is filtered off to give 0.85 g of the expected product. M.p.=160° C.

Preparation 22

5-Ethoxy-1,3-dihydro-3-(4(a,e)-dimethylaminocyclohexyl)-2H-benzimidazol-2-one

A) 4-Dimethylaminocyclohexylamine

A mixture of 68 g of 4-dimethylaminoaniline and 34 g of 5% palladium-on-charcoal in 250 ml of AcOH is hydrogenated at a temperature of 75°–90° C. under a pressure of 50 bar. The catalyst is filtered off and washed with water and the filtrate is evaporated under vacuum. The residue is taken up with water, rendered alkaline by the addition of concentrated NaOH, extracted with AcOEt and dried over $Na_2SO_4$ and the solvent is evaporated off under vacuum. The oil obtained is distilled under reduced pressure to give 16.2 g of the expected product in the form of an oil. B.p.=102°–110° C. under 20 mm Hg.

B) 4-Chloro-2-[(4(a,e)-dimethylaminocyclohexyl)amino]-1-nitrobenzene

A mixture of 22 g of 4-chloro-1,2-dinitrobenzene, 16 g of the compound obtained in the previous step and 20 ml of triethylamine in 30 ml of EtOH is stirred for 20 hours at RT. The reaction mixture is evaporated under vacuum, the residue is taken up with water, extracted with AcOEt, washed with water and dried over $Na_2SO_4$ and the solvent is evaporated off under vacuum. The residue is chromatographed on alumina using DCM as the eluent to give 14.9 g of the expected product in the form of an oil, which crystallizes. M.p.=85° C.

C) 4-Ethoxy-2-[(4(a,e)-dimethylaminocyclohexyl)amino]-1-nitrobenzene 14.9 g of the compound obtained in the previous step and 15 ml of tris[2-(2-methoxyethoxy)ethyl]amine are added to a solution of sodium ethylate, prepared from 1.5 g of sodium and 80 ml of EtOH, and the mixture is refluxed for 5 hours. The reaction mixture is evaporated under vacuum, the residue is taken up with water, extracted with iso ether, washed with water and dried over $Na_2SO_4$ and the solvent is evaporated off under vacuum to give 9 g of the expected product after crystallization from iso ether. M.p. =75° C.

D) 1-Amino-4-ethoxy-2-[(4(a,e)-dimethylaminocyclohexyl)amino]benzene

A mixture of 9 g of the compound obtained in the previous step, 2 g of 5% palladium-on-charcoal and 40 ml of EtOH is hydrogenated for 3 hours at RT and at atmospheric pressure. The catalyst is filtered off and washed with MeOH and the filtrate is evaporated under vacuum to give 7.3 g of the expected product in the form of an oil, which is used as such in the next step.

E) 4-Ethoxy-1-ethoxycarboxamido-2-[(4(a,e)-dimethylaminocyclohexyl)amino]benzene A mixture of 7.2 g of the compound obtained in the previous step and 12 g of triethylamine in 70 ml of DCM is cooled to 10° C. and a solution of 2.9 ml of ethyl chloroformate in 10 ml of DCM is added dropwise. The mixture is stirred for 3 hours, the temperature being allowed to rise to RT, and evaporated under vacuum. The residue is taken up with water, extracted with DCM and dried over $Na_2SO_4$ and the solvent is evaporated off under vacuum to give 3.7 g of the expected product after crystallization from iso ether. M.p.=193°–195° C.

F) 5-Ethoxy-1,3-dihydro-3-(4(a,e)-dimethylaminocyclohexyl)-2H-benzimidazol-2-one 3.6 g of the compound obtained in the previous step are added to a solution of sodium ethylate, prepared from 0.3 g of sodium and 30 ml of EtOH, and the mixture is refluxed for 5 hours. The residue is taken up with water and the precipitate formed is filtered off and washed with water, with isopropanol and with pentane to give 2.15 g of the expected product. M.p.=215°–217° C.

Preparation 23

5-Ethoxy-1,3-dihydro-3-(4-methylpiperazin-1-yl)-2H-benzimidazol-2-one

A) 4-Chloro-2-[(4-methylpiperazin-1-yl)amino]-1-nitrobenzene

A mixture of 35 g of 4-chloro-1,2-dinitrobenzene and 20 g of 1-amino-4-methylpiperazine in 200 ml of 96° EtOH is stirred for 24 hours at RT. The reaction mixture is evaporated under vacuum and the residue is chromatographed on silica using a DCM/AcOEt mixture (80/20; v/v) as the eluent to give 17.5 g of the expected product after crystallization from an iso ether/heptane mixture (50/50; v/v). M.p.=108° C.

B) 4-Ethoxy-2-[(4-methylpiperazin-1-yl)amino]-1-nitrobenzene 17.5 g of the compound obtained in the previous step and 13 ml of tris[2-(2-methoxyethoxy)ethyl]amine are added to a solution of sodium ethylate, prepared from 1.5 g of sodium and 85 ml of EtOH, and the mixture is refluxed for 4 hours. The reaction mixture is evaporated under vacuum, the residue is taken up with water, extracted with DCM and dried over $Na_2SO_4$ and the solvent is evaporated off under vacuum to give 13.5 g of the expected product after crystallization from iso ether. M.p.=145° C.

C) 1-Amino-4-ethoxy-2-[(4-methylpiperazin-1-yl)amino]benzene

A mixture of 13.5 g of the compound obtained in the previous step, 0.75 g of 5% palladium-on-charcoal and 350 ml of 96° EtOH is hydrogenated for 3 hours at RT and at atmospheric pressure. The catalyst is filtered off and the filtrate is evaporated under vacuum to give 10.5 g of the expected product, which is used as such in the next step.

D) 4-Ethoxy-1-ethoxycarboxamido-2-[(4-methylpiperazin-1-yl)amino]benzene

A mixture of 5 g of the compound obtained in the previous step and 2.2 ml of triethylamine in 60 ml of DCM is cooled in an ice bath and a solution of 2.2 ml of ethyl chloroformate in 20 ml of DCM is added dropwise. The mixture is stirred for 16 hours, the temperature being allowed to rise to RT, and the solvent is evaporated off under vacuum. The residue is chromatographed on silica using a DCM/MeOH mixture (90/10; v/v) as the eluent to give 2.5 g of the expected product, which is used as such in the next step.

E) 5-Ethoxy-1,3-dihydro-3-(4-methylpiperazin-1-yl)-2H-benzimidazol-2-one

A solution of 2.5 g of the compound obtained above in 20 ml of EtOH is added to a solution of sodium ethylate, prepared from 0.36 g of sodium and 15 ml of EtOH, and the mixture is refluxed for 8 hours. It is evaporated under vacuum, the residue is taken up with water, extracted with AcOEt, washed with water and dried over $Na_2SO_4$ and the solvent is evaporated off under vacuum. The residue is chromatographed on silica using a DCM/AcOEt mixture (90/10; v/v) as the eluent to give 0.75 g of the expected product after crystallization from iso ether. M.p.=203° C.

Preparation 24

5-Ethoxy-1,3-dihydro-3-(morpholin-4-yl)-2H-benzimidazol-2-one

A) 4-Chloro-2-[(morpholin-4-yl)amino]-1-nitrobenzene

A mixture of 45 g of 4-chloro-1,2-dinitrobenzene, 25 g of 4-aminomorpholine and 30 g of triethylamine in 250 ml of 96° EtOH is stirred for 48 hours at RT. The precipitate formed is filtered off and washed with iso ether to give 30.2 g of the expected product. M.p.=155° C.

B) 4-Ethoxy-2-[(morpholin-4-yl)amino]-1-nitrobenzene 30.2 g of the compound obtained in the previous step are added to a solution of sodium ethylate, prepared from 3.5 g of sodium and 250 ml of EtOH, and the mixture is refluxed for 5 hours. The solvent is evaporated off under vacuum, the residue is extracted with AcOEt, washed with water and dried over $Na_2SO_4$ and the solvent is evaporated off under vacuum to give 19 g of the expected product after crystallization from EtOH. M.p.=152° C.

C) 1-Amino-4-ethoxy-2-[(morpholin-4-yl)amino]benzene

A mixture of 19 g of the compound obtained in the previous step and 2 g of 5% palladium-on-charcoal in 1000 ml of AcOEt is hydrogenated at RT and at atmospheric pressure. The catalyst is filtered off and the filtrate is evaporated under vacuum to give 14 g of the expected product in the form of an oil, which is used as such in the next step.

D) 4-Ethoxy-1-ethoxycarboxamido-2-[(morpholin-4-yl)amino]benzene

A mixture of 14 g of the compound obtained in the previous step and 5 ml of triethylamine in 300 ml of chloroform is cooled in an ice bath and 10 ml of ethyl chloroformate are added. The reaction mixture is stirred for 30 minutes at RT and washed with a 1N solution of NaOH, the organic phase is dried over $Na_2SO_4$ and the solvent is evaporated off under vacuum. The residue is taken up with iso ether, an insoluble material is filtered off and the filtrate is chromatographed on silica using a DCM/MeOH mixture (99/1; v/v) as the eluent to give 5 g of the expected product, which is used as such in the next step.

E) 5-Ethoxy-1,3-dihydro-3-(morpholin-4-yl)-2H-benzimidazol-2-one 5 g of the compound obtained in the previous step are added to a solution of sodium ethylate, prepared from 1 g of sodium and 50 ml of EtOH, and the mixture is refluxed for 5 hours. It is evaporated under vacuum, the residue is extracted with AcOEt, washed with water and dried over $Na_2SO_4$ and the solvent is evaporated off under vacuum to give 1.87 g of the expected product after crystallization from DCM and recrystallization from EtOH. M.p.=228° C.

Preparation 25

5-Ethoxy-1,3-dihydro-3-(4-methoxyphenyl)-2H-benzimidazol-2-one

A) 4-Chloro-2-[(4-methoxyphenyl)amino]-1-nitrobenzene

A mixture of 10 g of 4-chloro-1,2-dinitrobenzene, 6.5 g of 4-methoxyaniline and 16 g of 1,2,3,4-tetramethylbenzene is refluxed for 15 hours. After cooling, water is added, the mixture is extracted with AcOEt, washed with a 1N solution of HCl , with a 1N solution of NaOH and with water and dried over $Na_2SO_4$ and the solvent is evaporated off under vacuum. The residue is taken up with iso ether, a gummy insoluble material is separated off and the filtrate is chromatographed on alumina using iso ether as the eluent to give 4.6 g of the expected product after crystallization from isopropanol. M.p.=98° C.

B) 4-Ethoxy-2-[(4-methoxyphenyl)amino]-1-nitrobenzene 4.5 g of the compound obtained in the previous step and 5 ml of tris[2-(2-methoxyethoxy)ethyl]amine are added to a solution of sodium ethylate, prepared from 0.45 g of sodium and 20 ml of EtOH, and the mixture is refluxed for 3 hours. It is evaporated under vacuum, the residue is taken up with water, extracted with ether, washed with a 1N solution of HCl and with water and dried over $Na_2SO_4$ and the solvent is evaporated off under vacuum to give 2.2 g of the expected product after crystallization from iso ether. M.p.=109° C.

C) 1-Amino-4-ethoxy-2-[(4-methoxyphenyl)amino]benzene

A mixture of 2.2 g of the compound obtained in the previous step, 0.5 g of 5% palladium-on-charcoal and 20 ml of EtOH is hydrogenated for 8 hours at RT and at atmospheric pressure. The catalyst is filtered off and washed with EtOH and the filtrate is evaporated under vacuum to give 1.9 g of the expected product, which is used as such in the next step.

D) 4-Ethoxy-1-ethoxycarboxamido-2-[(4-methoxyphenyl)amino]benzene

A mixture of 1.9 g of the compound obtained in the previous step and 3 g of triethylamine in 20 ml of DCM is cooled to 5° C. and 1.1 g of ethyl chloroformate are added. The mixture is stirred for 3 hours, the temperature being allowed to rise to RT, and evaporated under vacuum. The residue is taken up with water and dried over $Na_2SO_4$ and the solvent is evaporated off under vacuum to give 2.4 g of the expected product, which is used as such in the next step.

E) 5-Ethoxy-1,3-dihydro-3-(4-methoxyphenyl)-2H-benzimidazol-2-one

A solution of 2.4 g of the compound obtained in the previous step in 15 ml of EtOH is added to a solution of sodium ethylate, prepared from 0.17 g of sodium and 10 ml of EtOH, and the mixture is refluxed for 4 hours. It is evaporated under vacuum, the residue is taken up with a 1N solution of HCl and the precipitate formed is filtered off and washed with water and then with DCM to give 1.7 g of the expected product. M.p.=204° C.

Preparation 26

5-Ethoxy-1,3-dihydro-3-(4-isopropylphenyl)-2H-benzimidazol-2-one

A) 4-Chloro-2-[(4-isopropylphenyl)amino]-1-nitrobenzene

A mixture of 15 g of 4-chloro-1,2-dinitrobenzene, 10 g of 4-isopropylaniline and 25 ml of Décaline® is refluxed for 15 hours. The reaction mixture is concentrated under 0.01 mm Hg, the residue is taken up with water, extracted with ether, washed with a 1N solution of HCl and with water and dried over $Na_2SO_4$ and the solvent is evaporated off under vacuum. The residue is chromatographed on silica using iso ether as the eluent to give 13 g of the expected product, which is used as such in the next step.

B) 4-Ethoxy-2-[(4-isopropylphenyl)amino]-1-nitrobenzene

This compound is prepared by the procedure described in Preparation 25 step B) starting from 13 g of the compound obtained in the previous step. It is chromatographed on silica using pentane as the eluent to give 4.4 g of the expected product. M.p.=100.5° C.

C) 1-Amino-4-ethoxy-2-[(4-isopropylphenyl)amino]benzene

This compound is prepared by the procedure described in Preparation 25 step C) starting from 4.3 g of the compound obtained in the previous step. This gives 4 g of the expected product, which is used as such in the next step.

D) 4-Ethoxy-1-ethoxycarboxamido-2-[(isopropylphenyl)amino]benzene

This compound is prepared by the procedure described in Preparation 25 step D) starting from 3.9 g of the compound obtained in the previous step. It is chromatographed on silica using iso ether as the eluent to give 5 g of the expected product, which is used as such in the next step.

E) 5-Ethoxy-1,3-dihydro-3-(4-isopropylphenyl)-2H-benzimidazol-2-one

This compound is prepared by the procedure described in Preparation 25 step E) starting from 4.9 g of the compound obtained in the previous step. 2.8 g of the expected product are obtained after crystallization from EtOH. M.p.=202° C.

Preparation 27

5-Ethoxy-1,3-dihydro-3-(indan-2-yl)-2H-benzimidazol-2-one

A) 4-Chloro-2-(indan-2-yl)amino-1-nitrobenzene 26 g of 2-aminoindane hydrochloride and then 20 g of 4-chloro-1,2-dinitrobenzene are added to a solution of sodium ethylate, prepared from 0.61 g of sodium and 200 ml of EtOH, and the mixture is stirred for 48 hours at RT. The solvent is evaporated off under vacuum, the residue is extracted with AcOEt, washed with water and dried over $Na_2SO_4$ and the solvent is evaporated off under vacuum to give 10.3 g of the expected product after crystallization from EtOH. M.p.=108° C.

B) 4-Ethoxy-2-(indan-2-yl)amino-1-nitrobenzene 10.3 g of the compound obtained in the previous step are added to a solution of sodium ethylate, prepared from 2 g of sodium and 100 ml of EtOH, and the mixture is refluxed for 4 hours. The solvent is evaporated off under vacuum, the residue is extracted with AcOEt, washed with water and dried over $Na_2SO_4$ and the solvent is evaporated off under vacuum. The residue is chromatographed on silica using DCM as the eluent to give 8.5 g of the expected product. M.p.=151° C.

C) 1-Amino-4-ethoxy-2-(indan-2-yl)aminobenzene

A mixture of 8.5 g of the compound obtained in the previous step and 1 g of 5% palladium-on-charcoal in 500 ml of AcOEt is hydrogenated at RT and at atmospheric pressure. The catalyst is filtered off and the filtrate is evaporated under vacuum to give 7.2 g of the expected product, which is used as such in the next step.

D) 4-Ethoxy-1-ethoxycarboxamido-2-(indan-2-yl)aminobenzene

A mixture of 7.2 g of the compound obtained in the previous step and 8.4 g of ethyl chloroformate in 100 ml of chloroform is refluxed for 2 hours. It is extracted with chloroform, washed with a 1N solution of NaOH and dried over $Na_2SO_4$ and the solvent is evaporated off under vacuum. The residue is chromatographed on silica using DCM as the eluent to give 3.5 g of the expected product. M.p.=122° C.

E) 5-Ethoxy-1,3-dihydro-3-(indan-2-yl)-2H-benzimidazol-2-one

A solution of sodium ethylate is prepared from 0.7 g of sodium and 50 ml of EtOH. 3.5 g of the compound obtained in the previous step are added and the mixture is refluxed for 3 hours. The solvent is evaporated off under vacuum, the residue is taken up with water, extracted with DCM and dried over $Na_2SO_4$ and the solvent is evaporated off under vacuum to give 2.6 g of the expected product after crystallization from EtOH. M.p.=225° C.

Preparation 28

3-(Adamant-1-yl)-5-ethoxy-1,3-dihydro-2H-benzimidazol-2-one

A) 2-(Adamant-1-yl)amino-4-chloro-1-nitrobenzene 15.5 ml of triethylamine and then a suspension of 15 g of 1-aminoadamantane in 50 ml of 96° EtOH are added to a solution of 20 g of 4-chloro-1,2-dinitrobenzene in 80 ml of 96° EtOH. The mixture is refluxed for 7 hours and, after cooling, the precipitate formed is filtered off to give 7 g of the expected product. M.p.=146° C.

B) 2-(Adamant-1-yl)amino-4-ethoxy-1-nitrobenzene 7 g of the compound obtained in the previous step and 8 ml of tris[2-(2-methoxyethoxy)ethyl]amine are added to a solution of sodium ethylate, prepared from 0.6 g of sodium and 70 ml of EtOH, and the mixture is refluxed for 3 hours. The solvent is evaporated off under vacuum, the residue is taken up with water, extracted with DCM and dried over $Na_2SO_4$ and the solvent is evaporated off under vacuum to give 6 g of the expected product. M.p.=147° C.

C) 2-(Adamant-1-yl)amino-1-amino-4-ethoxybenzene

A mixture of 6 g of the compound obtained in the previous step, 0.85 g of 5% palladium-on-charcoal and 70 ml of 96° EtOH is hydrogenated at RT under a pressure of 2 bar. The catalyst is filtered off and washed with AcOEt and the filtrate is evaporated under vacuum to give 4.7 g of the expected product, which is used as such in the next step.

D) 2-(Adamant-1-yl)amino-4-ethoxy-1-ethoxycarboxamidobenzene

A mixture of 4.7 g of the compound obtained in the previous step and 6 ml of ethyl chloroformate in 70 ml of chloroform is refluxed for 1 hour 30 minutes. The solvent is evaporated off under vacuum, the residue is taken up with an iso ether/AcOEt mixture (50/50; v/v) and the precipitate formed is filtered off. The precipitate is chromatographed on silica using DCM and then a DCM/AcOEt mixture (80/20; v/v) as the eluent to give 5 g of the expected product, which is used as such in the next step.

E) 3-(Adamant-1-yl)-5-ethoxy-1,3-dihydro-2H-benzimidazol-2-one

This compound is prepared by the procedure described in Preparation 27 step E) starting from 5 g of the compound obtained above. After evaporation of the solvent under vacuum, the residue is taken up with AcOEt and the precipitate formed is filtered off to give 2.5 g of the expected product. M.p.=264° C.

Preparation 29

3-Cycloheptyl-5-ethoxy-1,3-dihydro-2H-benzimidazol-2-one

A) 2-Cycloheptylamino-4-ethoxy-1-nitrobenzene 25 g of the compound obtained in Preparation 5 step A) and 30 ml of tris[2-(2-methoxyethoxy)ethyl]amine are added to a solution of sodium ethylate, prepared from 2.2 g of sodium and 250 ml of EtOH, and the mixture is refluxed for 24 hours. It is concentrated under vacuum and the residue is chromatographed on silica using a DCM/heptane mixture (50/50; v/v) as the eluent to give 14 g of the expected product. M.p.=83° C.

B) 1-Amino-2-cycloheptylamino-4-ethoxybenzene

A mixture of 13 g of the compound obtained in the previous step, 0.3 g of 5% palladium-on-charcoal and 250 ml of 95° EtOH is hydrogenated for 24 hours at RT under a pressure of 2 bar. The catalyst is filtered off and the filtrate is evaporated under vacuum. The residue is chromatographed on silica using a DCM/heptane mixture (50/50; v/v), then DCM and finally a DCM/AcOEt mixture (90/10; v/v) as the eluent to give 6 g of the expected product, which is used as such in the next step.

C) 4-Ethoxy-1-ethoxycarboxamido-2-cycloheptylaminobenzene

A mixture of 6 g of the compound obtained in the previous step and 7.5 g of ethyl chloroformate in 50 ml of chloroform is refluxed for 5 hours. It is concentrated under vacuum and the residue is chromatographed on silica using DCM as the eluent to give 4.7 g of the expected product after crystallization from iso ether. M.p.=172° C.

D) 3-Cycloheptyl-5-ethoxy-1,3-dihydro-2H-benzimidazol-2-one 4.5 g of the compound obtained in the previous step are added to a solution of sodium ethylate, prepared from 0.35 g of sodium and 100 ml of EtOH, and the mixture is refluxed for 24 hours. It is concentrated under vacuum, the residue is extracted with AcOEt, washed with water and dried over $Na_2SO_4$ and the solvent is evaporated off under vacuum to give 2.9 g of the expected product after crystallization from iso ether. M.p.=204° C.

Preparation 30

5-Chloro-3-(2-chlorophenyl)-1,3-dihydro-2H-benzimidazol-2-one

A) 1-Amino-4-chloro-2-[(2-chlorophenyl)amino]benzene

A mixture of 3 g of the compound obtained in Preparation 14 step A), 0.5 g of Raney® nickel and 100 ml of 95° EtOH is hydrogenated for 4 hours at RT under a pressure of 2 bar. The catalyst is filtered off and the filtrate is evaporated under vacuum to give 2 g of the expected product, which is used as such in the next step.

B) 5-Chloro-3-(2-chlorophenyl)-1,3-dihydro-2H-benzimidazol-2-one

A mixture of 2 g of the compound obtained in the previous step and 2 g of 1,1'-carbonyldiimidazole in 50 ml of acetonitrile is refluxed for 30 minutes. The reaction mixture is concentrated under vacuum, the residue is extracted with AcOEt, washed with a 1N solution of HCl, with water, with a saturated solution of $NaHCO_3$ and with water and dried over $Na_2SO_4$ and the solvent is evaporated off under vacuum to give 1 g of the expected product after crystallization from iso ether. M.p.=239° C.

Preparation 31

5-Ethoxy-1,3-dihydro-3-(pyrid-2-yl)-2H-benzimidazol-2-one

A) 4-Chloro-1-nitro-2-(pyrid-2-yl)aminobenzene

This compound is prepared by the procedure described in Eur. J. Med. Chem.-Chim. Ther., 1983, 18 (6), 495–500.

B) 4-Ethoxy-1-nitro-2-(pyrid-2-yl)aminobenzene 6.2 g of the compound obtained in the previous step are added to a solution of sodium ethylate, prepared from 0.8 g of sodium and 50 ml of EtOH, and the mixture is refluxed for 3 hours. The reaction mixture is concentrated under vacuum, the residue is extracted with AcOEt, washed with water and dried over $Na_2SO_4$ and the solvent is evaporated off under vacuum. The residue is chromatographed on silica using a DCM/pentane mixture (50/50; v/v) as the eluent to give 3.5 g of the expected product, which is used as such in the next step.

C) 1-Amino-4-ethoxy-2-(pyrid-2-yl)aminobenzene

A mixture of 3.5 g of the compound obtained in the previous step and 0.2 g of 5% palladium-on-charcoal in 250 ml of AcOEt is hydrogenated at RT and at atmospheric pressure. The catalyst is filtered off and the filtrate is evaporated under vacuum to give 2.6 g of the expected product. M.p.=95° C.

D) 4-Ethoxy-1-ethoxycarboxamido-2-(pyrid-2-yl)aminobenzene and 4-ethoxy-1-ethoxycarboxamido-2-[N-ethoxycarbonyl-N-(pyrid-2-yl)amino]benzene 2 ml of ethyl chloroformate are added to a solution of 3.6 g of the compound obtained in the previous step and 2 ml of triethylamine in 100 ml of DCM and the mixture is stirred for 2 hours at RT. The reaction mixture is concentrated under vacuum, the residue is extracted with ACOEt, washed with water and dried over $Na_2SO_4$ and the solvent is evaporated off under vacuum to give 3.2 g of a mixture of the two title compounds of step D), which is used as such in the next step.

E) 5-Ethoxy-1,3-dihydro-3-(pyrid-2-yl)-2H-benzimidazol-2-one 3.2 g of the mixture of compounds obtained in the previous step are added to a solution of sodium ethylate, prepared from 0.6 g of sodium and 100 ml of EtOH, and the mixture is refluxed for 3 hours. The reaction mixture is concentrated under vacuum, the residue is extracted with AcOEt, washed with water and dried over $Na_2SO_4$ and the solvent is evaporated off under vacuum to give 2.7 g of the expected product after crystallization from iso ether. M.p.=205° C.

Preparation 32

3-Cyclopentyl-5-ethoxy-1,3-dihydro-2H-benzimidazol-2-one

A) 4-Chloro-2-cyclopentylamino-1-nitrobenzene

A mixture of 20 g of 4-chloro-1,2-dinitrobenzene and 20 g of cyclopentylamine in 50 ml of 95° EtOH is stirred overnight at RT. The precipitate formed is filtered off and washed with 95° EtOH to give 14 g of the expected product. M.p.=75° C.

B) 2-Cyclopentylamino-4-ethoxy-1-nitrobenzene 20 ml of tris[2-(2-methoxyethoxy)ethyl]amine and 14 g of the compound obtained in the previous step are added to a solution of sodium ethylate, prepared from 2 g of sodium and 150 ml of EtOH, and the mixture is then refluxed for 24 hours. The reaction mixture is concentrated under vacuum, the residue is extracted with AcOEt, washed with water and dried over $Na_2SO_4$ and the solvent is evaporated off under vacuum. The residue is chromatographed on silica using a DCM/heptane mixture (50/50; v/v) as the eluent to give 10 g of the expected product, which is used as such in the next step.

C) 1-Amino-2-cyclopentylamino-4-ethoxybenzene

A mixture of 10 g of the compound obtained in the previous step and 0.6 g of 5% palladium-on-charcoal in 200 ml of 95° EtOH is hydrogenated for 3 hours at RT under a pressure of 2 bar. The catalyst is filtered off and the filtrate is evaporated under vacuum to give 8.2 g of the expected product, which is used as such in the next step.

D) 2-Cyclopentylamino-4-ethoxy-1-ethoxycarboxamidobenzene

A mixture of 8 g of the compound obtained in the previous step and 8 ml of ethyl chloroformate in 50 ml of chloroform is refluxed for 5 hours. The reaction mixture is concentrated under vacuum, the residue is taken up with a hot iso ether/AcOEt mixture (75/25; v/v) and the precipitate is filtered off and washed with iso ether to give 9.5 g of the expected product. M.p.=173° C.

E) 3-Cyclopentyl-5-ethoxy-1,3-dihydro-2H-benzimidazol-2-one 9.5 g of the compound obtained in the previous step are added to a solution of sodium ethylate, prepared from 0.9 g of sodium and 225 ml of EtOH, and the mixture is refluxed for 18 hours. The reaction mixture is concentrated under vacuum, the residue is extracted with AcOEt, washed with water and dried over $Na_2SO_4$ and the solvent is evaporated off under vacuum to give 4 g of the expected product after crystallization from an AcOEt/iso ether mixture (50/50; v/v). M.p.=178° C.

Furthermore, the benzenesulfonyl chlorides described in Table 1 below were prepared using the procedure described in the general section:

TABLE 1

[Structure: benzene ring with Cl-SO₂- at one position, OCH₃ ortho, and YR"₆ para]

| Y | R"₆ | m.p. °C. |
|---|---|---|
| S | $CH_3$ | 85 |
| O | $CH_2Bz$ | 95 |
| O | $CH_2CO_2Et$ | 89 |
| O | $(CH_2)_3Br$ | 106–108 |

EXAMPLE 1

5-Chloro-1,3-dihydro-1-(2-methoxy-4-nitrobenzenesulfonyl)-3-phenyl-2H-benzimidazol-2-one 0.15 g of sodium hydride as an 80% dispersion in oil was added in portions, with stirring, to a solution of 1.223 g of 5-chloro-1,3-dihydro-3-phenyl-2H-benzimidazol-2-one in 12 ml of DMF at room temperature; 1.384 g of 2-methoxy-4-nitrobenzenesulfonyl chloride were then introduced and the reaction medium was stirred at room temperature for 24 hours. The solvent was then evaporated off under vacuum and the residue obtained was taken up with water. It was then extracted with DCM, washed with water and then dried over sodium sulfate and the solvent was evaporated off to dryness. The residue obtained was chromatographed on silica using a DCM/AcOEt mixture (92/8; v/v) as the eluent to give the expected product in the form of a yellow product, which crystallized from absolute EtOH. m=1.870 g. M.p.>250° C.

EXAMPLE 2

3-Cyclohexyl-1,3-dihydro-5-methoxy-1-(4-nitrobenzenesulfonyl)-2H-benzimidazol-2-one 0.066 g of sodium hydride as an 80% dispersion in oil was added in portions, with stirring, to a solution of 0.493 g of 3-cyclohexyl-1,3-dihydro-5-methoxy-2H-benzimidazol-2-one in 5 ml of DMF. The mixture was stirred for 30 minutes; it was then cooled in an ice bath and 0.490 g of 4-nitrobenzenesulfonyl chloride was added. The mixture was stirred for 24 hours, the temperature being allowed to rise to room temperature. The solvent was evaporated off under vacuum and the residue was taken up with water. It was then extracted with DCM, washed with water and then dried over sodium sulfate and the solvent was evaporated off to dryness. The residue was chromatographed on silica using a DCM/AcOEt mixture (95/5; v/v) as the eluent.

The expected product was obtained in the form of a yellow solid, which was crystallized from absolute EtOH. m=0.580 g. M.p.=160° C.

EXAMPLE 3

5-Chloro-1,3-dihydro-1-(2-methoxy-4-nitrobenzenesulfonyl)-3-cyclohexyl-2H-benzimidazol-2-one 0.13 g of sodium hydride as an 80% dispersion in oil was added in portions, with stirring, to a solution of 1 g of 5-chloro-3-cyclohexyl-1,3-dihydro-2H-benzimidazol-2-one in 10 ml of DMF at room temperature; 1.1 g of 2-methoxy-4-nitrobenzenesulfonyl chloride were then introduced and the reaction medium was stirred at room temperature for 4 hours. The solvent was then evaporated off under vacuum and the residue obtained was taken up with water. It was then extracted with DCM, washed with water and then dried over sodium sulfate and the solvent was evaporated off to dryness. The residue obtained was chromatographed on silica using a DCM/AcOEt mixture (95/5; v/v) as the eluent to give the expected product in the form of a slightly yellow solid, which crystallized from absolute EtOH. m=1.52 g. M.p.=185° C.

EXAMPLE 4

5-Chloro-1,3-dihydro-1-(4-nitrobenzenesulfonyl)-3-cyclohexyl-2H-benzimidazol-2-one 0.066 g of sodium hydride as an 80% dispersion in oil was added in portions, with stirring, to a solution of 0.5 g of 5-chloro-3-cyclohexyl-1,3-dihydro-2H-benzimidazol-2-one in 5 ml of DMF. The mixture was stirred for 30 minutes; 0.49 g of 4-nitrobenzenesulfonyl chloride was then introduced. The reaction medium was stirred for 24 hours at room temperature. The solvent was evaporated off under vacuum and the residue was taken up with water. It was then extracted with DCM, washed with water and then dried over sodium sulfate and the solvent was evaporated off to dryness. The residue was chromatographed on silica using a DCM/AcOEt mixture (95/5; v/v) as the eluent.

The expected product was obtained in the form of a pale yellow solid, which was crystallized from absolute EtOH. m=0.57g. M.p.=162° C.

EXAMPLE 5

5-Ethoxy-1,3-dihydro-1-[2-methoxy-4-(N,N-dimethylamino)benzenesulfonyl]-3-cyclohexyl-2H-benzimidazol-2-one A) 5-Ethoxy-1,3-dihydro-1-(2-methoxy-4-nitrobenzenesulfonyl)-3-cyclohexyl-2H-benzimidazol-2-one 0.5 g of sodium hydride as a 60% dispersion in oil was added to a solution of 4.95 g of 5-ethoxy-3-cyclohexyl-1,3-dihydro-2H-benzimidazol-2-one in 40 ml of THF and 20 ml of DMF.

The reaction medium was stirred for 30 minutes at 20° C. and 5.3 g of 2-methoxy-4-nitrobenzenesulfonyl chloride in 15 ml of THF were then added over 5 minutes at 20° C. The reaction medium was stirred for 4 hours at 20° C. and then concentrated under vacuum and the residue was taken up with water. The precipitate was filtered off, crystallized from absolute ethanol and then recrystallized from isopropanol to give 9.1 g of the expected product in the form of a yellow solid. M.p.=162° C.

B) 5-Ethoxy-1,3-dihydro-1-(2-methoxy-4-aminobenzenesulfonyl)-3-cyclohexyl-2H-benzimidazol-2-one A suspension containing 8.9 g of the compound obtained in the previous step, 11 g of iron powder and 35 ml of 95° ethanol was brought to the reflux point. A solution of 4 ml of concentrated hydrochloric acid in 15 ml of ethanol was then added over 15 minutes to the resulting reaction mixture, followed by 10 ml of AcOH. The reaction mixture was refluxed for 3 hours. It was cooled, washed with a saturated aqueous solution of $NaHCO_3$, extracted with DCM, dried over $Na_2SO_4$ and concentrated. The residue was recrystallized from isopropyl ether to give 6.7 g of the expected product. M.p.=228° C.

C) 5-Ethoxy-1,3-dihydro-1-[2-methoxy-4-(N,N-dimethylamino)benzenesulfonyl]-3-cyclohexyl-2H-benzimidazol-2-one 0.5 g of sodium cyanoborohydride in 0.15 ml of AcOH was added at 20° C. to a suspension of 0.5 g of the compound obtained in the previous step in 10 ml of $CH_3CN$ and 4 ml of an aqueous solution of formaldehyde (37%) and the reaction mixture was then stirred for 48 hours at 20° C. The reaction medium was then taken up with ethyl ether, washed with water and then dried over sodium sulfate and concentrated. The residue was chromatographed on silica using DCM as the eluent to give 0.1 g of the expected product in the form of a yellow solid, which was crystallized from absolute ethanol and recrystallized from isopropanol. M.p.=220° C.

EXAMPLE 6

5-Ethoxy-1,3-dihydro-1-[2-methoxy-4-(Δ3-pyrrolin-1-yl)benzenesulfonyl]-3-cyclohexyl-2H-benzimidazol-2-one A suspension containing 2 g of the compound obtained in step B) of Example 5 and 1.5 g of cis-1,4-dichlorobut-2-ene in 30 ml of DMF and 1.5 ml of triethylamine was refluxed for 2 hours. The reaction medium was then poured into a water/ice mixture and extracted with AcOEt. The organic phase was washed with water, dried over sodium sulfate and then evaporated under vacuum. The residue was chromatographed on silica gel using DCM as the eluent to give 0.64 g of the expected product, which crystallizes from an ethyl acetate/iso ether mixture (50/50; v/v). M.p.=212° C.

EXAMPLE 7

5-Chloro-1,3-dihydro-1-(2-methoxy-4-aminobenzenesulfonyl)-3-cyclohexyl-2H-benzimidazol-2-one 1.8 g ($4.10^{-3}$ mol) of the compound obtained in Example 3 in 95° EtOH were hydrogenated under 50 bar in the presence of Raney® nickel. The catalyst was filtered off on Célite® and rinsed with hot 95° EtOH and the filtrate was evaporated under vacuum to give 1.22 g of the expected product in the form of a white solid. The product crystallized from absolute ethanol. M.p.=211° C.

EXAMPLE 8

5-Chloro-1,3-dihydro-1-(2-methoxy-4-aminobenzenesulfonyl)-3-phenyl-2H-benzimidazol-2-one A mixture of 1.8 g ($4.10^{-3}$ mol) of 5-chloro-1,3-dihydro-1-(2-methoxy-4- nitrobenzenesulfonyl)-3- phenyl-2H-benzimidazol-2-one, obtained in Example 1, and 1 g of Raney® nickel in 70 ml of 95° ethanol was hydrogenated for 24 hours at room temperature under a pressure of 50 bar. The catalyst was then filtered off on Célite® and the filtrate was evaporated under vacuum. The residue was chromatographed on silica using a DCM/MeOH mixture (99/1; v/v) as the eluent to give 0.6 g of the expected product in the form of an ochre solid. M.p.=205° C.

EXAMPLE 9

5-Ethoxy-1,3-dihydro-1-[2-methoxy-4-(2-ethylbutyrylamino)benzenesulfonyl]-3-cyclohexyl-2H-benzimidazol-2-one 0.5 g of the compound obtained in Example 5 step B) in 20 ml of DCM was mixed with 0.5 g of 2-ethylbutyroyl chloride and 0.5 g of pyridine. The mixture was concentrated under vacuum, extracted with ethyl ether and then washed with water, with 1N hydrochloric acid and then with water. The residue was chromatographed on silica using DCM as the eluent to give the expected product, which crystallized from isopropyl ether. m=0.17 g. M.p.=168° C.

EXAMPLE 10

5-Ethoxy-1,3-dihydro-1-[2-methoxy-4-(2-methylphenylcarbonylamino)benzenesulfonyl]-3-cyclohexyl-2H-benzimidazol-2-one 0.46 g of the compound prepared in Example 5 step B), 20 ml of DCM and 0.5 g of pyridine were mixed at 20° C. and 0.18 g of 2-methylbenzoyl chloride in 10 ml of DCM was then added. The reaction mixture was stirred for 16 hours and then concentrated under vacuum. The residue was washed with water, with 1N hydrochloric acid, with 10% sodium carbonate and then with water. It was dried over sodium sulfate and the solvent was then evaporated off to dryness to give the expected product in the form of a white solid, which crystallized from isopropyl ether. m=0.3 g. M.p.=180° C.

EXAMPLE 11

5-Ethoxy-1,3-dihydro-1-[2-methoxy-4-(diethylaminoacetamido)benzenesulfonyl]-3-cyclohexyl-2H-benzimidazol-2-one fumarate A) 5-Ethoxy-1,3-dihydro-1-(2-methoxy-4-chloroacetamidobenzenesulfonyl)-3-cyclohexyl-2H-benzimidazol-2-one 0.52 g of the compound obtained in Example 5 step B), 25 ml of DCM and 0.5 g of pyridine were mixed. 0.54 ml of chloroacetyl chloride in 10 ml of DCM was then added over 5 minutes at 20° C. The reaction mixture was stirred for 2 hours at 20° C. and then concentrated under vacuum at 20° C. The residue was extracted with AcOEt and washed with water, then with 1N hydrochloric acid and then with water. It was dried over sodium sulfate and the solvent was evaporated off to give the expected product, which crystallized from isopropyl ether. m=0.6 g. M.p.=232° C.

B) 5-Ethoxy-1,3-dihydro-1-[2-methoxy-4-(diethylaminoacetamido)benzenesulfonyl]-3-cyclohexyl-2H-benzimidazol-2-one fumarate 0.55 g of the compound obtained in step A) above was mixed at 20° C. with 20 ml of THF and 10 ml of diethylamine. The reaction mixture was left to stand for 15 hours and then concentrated under vacuum. The residue was taken up with water, extracted with AcOEt and washed with 1N HCl and with water; it was dried over $Na_2SO_4$ and the solvent was evaporated off under vacuum. The residue is chromatographed on silica using DCM and then DCM/AcOEt (95/5; v/v) as the eluent to give 0.5 g of a wax, which was converted to a salt with 0.1 g of fumaric acid in 20 ml of acetone. The salt obtained is soluble in ethyl ether. m=0.2 g. M.p.=124° C.

EXAMPLE 12

5-Ethoxy-1,3-dihydro-(2-methoxy-4-benzyloxycarbonylbenzenesulfonyl)-3-cyclohexyl-2H-benzimidazol-2-one 0.5 g of sodium hydride as a 60% dispersion in oil was added in small portions, at room temperature, to a solution of 2.4 g of 5-ethoxy-3-cyclohexyl-1,3-dihydro-2H-benzimidazol-2-one in 50 ml of THF and 50 ml of DMF and the mixture was stirred for half an hour, still at room temperature. 3.4 g of 2-methoxy-4-benzyloxycarbonylbenzenesulfonyl chloride were then added and the reaction medium was stirred for 4 hours at room temperature. It was concentrated under vacuum to remove the residual THF and the residue was taken up with water. It was then extracted with AcOEt and washed with water and the organic phase was dried over sodium sulfate and concentrated under vacuum. The residue obtained was then purified by chromatography on silica using DCM as the eluent. 4.2 g of the expected product were obtained in the form of a white solid by crystallization from iso ether. M.p.=131° C.

EXAMPLE 13

5-Ethoxy-1,3-dihydro-1-(2-methoxy-4-carboxybenzenesulfonyl)-3-cyclohexyl-2H-benzimidazol-2-one 4 g of 5-ethoxy-1,3-dihydro-1-(2-methoxy-4-benzyloxycarbonylbenzenesulfonyl)-3-cyclohexyl-2H-benzimidazol-2-one in 100 ml of AcOEt were hydrogenated at room temperature and at atmospheric pressure in the presence of 200 mg of Pd/C. The catalyst was filtered off on Célite® and the filtrate was concentrated under vacuum. 2.47 g of the expected compound were obtained in the form of a white solid by crystallization from iso ether. M.p.=205° C.

EXAMPLE 14

5-Ethoxy-1,3-dihydro-1-[2-methoxy-4-(N-(tert-butyl)carbamoyl)benzenesulfonyl]-3-cyclohexyl-2H-benzimidazol-2-one 700 mg of the compound obtained in the previous Example, 780 mg of BOP and 1 ml of tert-butylamine were mixed with 50 ml of DCM and 2 ml of DIPEA and the reaction medium was stirred for 30 minutes at room temperature. It was concentrated under vacuum and the residue was taken up with water and extracted with DCM. It was washed with 1N HCl and then with 1N NaOH and the organic phase was dried over sodium sulfate and concentrated under vacuum. The residue obtained was then purified by chromatography on silica using a DCM/ AcOEt mixture (97.5/2.5; v/v) as the eluent to give 500 mg of the expected compound in the form of a white solid. m=2.47 g. M.p.= 252° C.

EXAMPLE 15

5-Ethoxy-1,3-dihydro-1-[2-methoxy-4-(N-(1-ethoxycarbonyl-1-methylethyl)carbamoyl)benzenesulfonyl]-3-cyclohexyl-2H-benzimidazol-2-one 500 mg of the compound obtained in Example 13, 300 mg of 1-ethoxycarbonyl-1-methylethylamine hydrochloride and 550 mg of BOP were mixed with 2 ml of DIPEA and 50 ml of DCM and the reaction medium was stirred for 30 minutes at room temperature. It was then concentrated under vacuum and the residue was taken up with water and then extracted with AcOEt, washed successively with 1N HCl , with 1N NaOH and then with water, dried over sodium sulfate and concentrated under vacuum. The residue was purified by chromatography on a silica column using a DCM/AcOEt mixture (97/3; v/v) as the eluent. 170 mg of the expected product were obtained in the form of a white solid by crystallization from an AcOEt/iso ether mixture (10/90; v/v). M.p.=202° C.

EXAMPLE 16

5-Ethoxy-1,3-dihydro-1-[2-methoxy-4-(N',N'-diethylureido)benzenesulfonyl]-3-cyclohexyl-2H-benzimidazol-2-one
A) 5-Ethoxy-1,3-dihydro-1-[2-methoxy-4-phenoxycarbonylaminobenzenesulfonyl]-3-cyclohexyl-2H-benzimidazol-2-one 0.29 g of NaOH pellets in 2 ml of water was added at 5° C., with stirring, to a solution of 1.1 g of 5-ethoxy-1,3-dihydro-1-(2-methoxy-4-aminobenzenesulfonyl)-3-cyclohexyl-2H-benzimidazol-2-one, obtained in Example 5 step B), in 25 ml of THF. 1 ml of phenyl chloroformate was then added with continued stirring. The reaction mixture was then stirred for 5 hours, the temperature being allowed to rise to 20° C. The mixture was then concentrated under vacuum, the residue was taken up with water, extracted with ether and washed with water and the organic phase was dried over sodium sulfate and concentrated under vacuum. 1 g of the expected product was obtained by crystallization from iso ether. M.p.=197° C.
B) 5-Ethoxy-1,3-dihydro-1-[2-methoxy-4-(N',N'-diethylureido)benzenesulfonyl]-3-cyclohexyl-2H-benzimidazol-2-one 0.5 g of the product obtained in the previous step in 15 ml of EtOH and 0.5 g of diethylamine in 10 ml of DCM were mixed at 20° C., with stirring. The reaction mixture was then left to stand for 15 hours and then concentrated under vacuum. The residue was taken up with water, extracted with ether and then washed successively with water, with a 1N solution of NaOH and again with water. The organic phase was dried over sodium sulfate and concentrated under vacuum. The product crystallized from iso ether to give 0.33 g of the expected compound in the form of a yellowish solid. M.p.=165° C.

EXAMPLE 17

5-Chloro-1,3-dihydro-1-[2-methoxy-4-(N',N'-diethylureido)benzenesulfonyl]-3-cyclohexyl-2H-benzimidazol-2-one
A) 5-Chloro-1,3-dihydro-1-[2-methoxy-4-phenoxycarbonylaminobenzenesulfonyl]-3-cyclohexyl-2H-benzimidazol-2-one 0.24 g of NaOH pellets in 2 ml of water was added at 5° C., with stirring, to a solution of 1.05 g of the compound obtained in Example 7 in 25 ml of THF. 1 ml of phenyl chloroformate was then added with continued stirring. The reaction mixture was then stirred for 5 hours, the temperature being allowed to rise to 20° C. The mixture was then concentrated under vacuum, the residue was taken up with water, extracted with ether and washed with water and the organic phase was dried over sodium sulfate and concentrated under vacuum. 1.35 g of the expected product were obtained by crystallization from iso ether. M.p.=236° C.
B) 5-Chloro-1,3-dihydro-1-[2-methoxy-4-(N',N'-diethylureido)benzenesulfonyl]-3-cyclohexyl-2H-benzimidazol-2-one 0.5 g of the product obtained in the previous step in 15 ml of EtOH and 0.5 g of diethylamine in 10 ml of DCM were mixed at 20° C., with stirring. The reaction mixture was then left to stand for 20 hours and then concentrated under vacuum. The residue was taken up with a 1N solution of NaOH, extracted with AcOEt and washed with water and the organic phase was dried over sodium sulfate and concentrated under vacuum. 0.45 g of the expected product was obtained in the form of a white solid by crystallization from iso ether. M.p.=250° C.

EXAMPLE 18

5-Ethoxy-1,3-dihydro-1-[2-methoxy-4-(piperid-1-ylcarbonylamino)benzenesulfonyl]-3-cyclohexyl-2H-benzimidazol-2-one 2 ml of piperidine were added to a solution of 500 mg of the compound obtained in Example 16 step A) in 25 ml of DCM. The reaction mixture was then stirred for 18 hours at room temperature. It was concentrated to dryness and the resulting product was passed over silica using DCM and then a DCM/AcOEt mixture (95/5; v/v) as the eluent to give 0.36 g of the expected product in the form of white crystals. M.p. =232° C.

EXAMPLE 19

5-Chloro-1,3-dihydro-1-[2-methoxy-4-(N',N'-diethylureido)benzenesulfonyl]-3-cycloheptyl-2H-benzimidazol-2-one
A) 5-Chloro-1,3-dihydro-1-[2-methoxy-4-nitrobenzenesulfonyl]-3-cycloheptyl-2H-benzimidazol-2-one 600 mg of sodium hydride as a 60% dispersion in oil were added in portions, with stirring, to a solution of 3 g of 5-chloro-3-cycloheptyl-1,3-dihydro-2H- benzimidazol-2-one in 30 ml of THF. 3 g of 4-nitro-2- methoxybenzenesulfonyl chloride were then added and the reaction mixture was stirred for 18 hours. The reaction mixture was then poured into a water+ ice mixture, extracted with ethyl acetate and washed with water and the organic phase was dried over sodium sulfate and concentrated to dryness. 3.5 g of the expected product were obtained by crystallization from an iso ether/AcOEt mixture (60/40; v/v). M.p.=193° C.
B) 5-Chloro-1,3-dihydro-1-[2-methoxy-4-aminobenzenesulfonyl]-3-cycloheptyl-2H-benzimidazol-2-one A mixture of 1.5 g of the product obtained in the previous step, 6 ml of alcohol, 6 ml of water, 2 g of iron powder and 1 ml of concentrated HCl in 3 ml of water was refluxed for 4 hours. The reaction medium was then diluted in a water+ ice mixture, the insoluble material was filtered off and the precipitate obtained was washed with AcOEt. The filtrate was extracted with AcOEt and washed with water and the organic phase was dried over sodium sulfate and concentrated to dryness. 0.81 g of the expected product was obtained by crystallization from ethanol. M.p.=219° C.
C) 5-Chloro-1,3-dihydro-1-[2-methoxy-4-(phenoxycarbonylamino)benzenesulfonyl]-3-cycloheptyl-2H-benzimidazol-2-one 60 mg of sodium hydroxide pellets in 1 ml of water were added at a temperature less than or equal to 10° C., with stirring, to a solution of 0.5 g of the product obtained in the previous step in 15 ml of THF. 0.6 ml of phenyl chloroformate was then added and the reaction mixture was stirred for 3 hours. It was concentrated to dryness, the residue was taken up with ethyl acetate and washed with water and the organic phase was dried over sodium sulfate and concentrated to dryness. 0.59 g of the expected product was obtained by crystallization from iso ether. M.p.=234° C.

D) 5-Chloro-1,3-dihydro-1-[2-methoxy-4-(N',N'-diethylureido)benzenesulfonyl]-3-cycloheptyl-2H-benzimidazol-2-one 500 mg of the product obtained in the previous step and 2 ml of diethylamine were mixed with 30 ml of DCM and the reaction mixture was stirred for 2 hours at room temperature. It was then concentrated to dryness and the residue was crystallized from 30 ml of an AcOEt/iso ether mixture (50/50; v/v) to give 0.27 g of the expected compound in the form of white crystals. M.p.=218° C.

EXAMPLE 20

5-Chloro-1,3-dihydro-1-(3,4-dimethoxybenzenesulfonyl)-3-phenyl-2H-benzimidazol-2-one 66 mg of sodium hydride as an 80% dispersion in oil were added in portions to a solution of 490 mg of 5-chloro-1,3-dihydro-3-phenyl-2H-benzimidazol-2-one in 5 ml of DMF and the reaction medium was stirred for 30 minutes. 520 mg of 3,4-dimethoxybenzenesulfonyl chloride were then introduced and the reaction medium was stirred overnight at room temperature. The solvent was then evaporated off under vacuum and the residue obtained was taken up with water. It was then extracted with DCM, washed with water and then dried over sodium sulfate and the solvent was evaporated off to dryness. The residue obtained was chromatographed on silica using a DCM/AcOEt mixture (95/5; v/v) as the eluent to give the expected product in the form of a white solid, which crystallized from absolute EtOH. m=0.71 g. M.p.=154° C.

The compounds of formula (I) according to the invention described in Table 2 below were prepared by the procedure described above:

TABLE 2

| EX | $R_1$ | $R_2$ | $R_3$ | $R_5$ | $R_6$ | m.p. °C. |
|----|-------|-------|-------|-------|-------|----------|
| 21 | $CH_3O$ | H | cyclohexyl | 2-$CH_3O$ | 4-$CH_3O$ | 118 |
| 22 | $CH_3O$ | H | cyclohexyl | 3-$CH_3O$ | 4-$CH_3O$ | 139 |
| 23 | Cl | H | phenyl | 2-$CH_3O$ | 4-$CH_3O$ | 196 |
| 24 | $C_2H_5O$ | H | cyclohexyl | 2-$CH_3O$ | 4-$CH_3O$ | 163 |
| 25 | Cl | H | 4-benzylpiperidinyl | 2-$CH_3O$ | 4-$CH_3O$ | 88 |
| 26 | Cl | H | 4-benzylpiperidinyl | 3-$CH_3O$ | 4-$CH_3O$ | 95 |
| 27 | Cl | H | cyclohexylmethyl | 3-$CH_3O$ | 4-$CH_3O$ | 142 |

TABLE 2-continued

| EX | R₁ | R₂ | R₃ | R₅ | R₆ | m.p. °C. |
|----|----|----|----|----|----|----------|
| 28 | Cl | H | —CH₂—cyclohexyl | 2-CH₃O | 4-CH₃ | 136 |
| 29 | Cl | H | cyclohexyl | 3-CH₃O | 4-CH₃O | 148 |
| 30 | Cl | H | cyclohexyl | 2-CH₃O | 4-CH₃O | 156 |
| 31 | Cl | H | cycloheptyl | 2-CH₃O | 4-CH₃O | 153 |

EXAMPLE 32

N-Benzyl-N-methyl-4-[5-chloro-2,3-dihydro-1-(2,4-dimethoxybenzenesulfonyl)-2-oxo-1H-benzimidazol-3-yl] piperidinium iodide 0.75 g of the compound of Example 25 was mixed with 10 ml of methyl iodide in 200 ml of ethyl ether. The reaction medium was kept at 20° C. for 5 days. The precipitate formed was separated off, washed with ethyl ether and dried to give 0.35 g of the expected iodide. M.p.=178° C.

EXAMPLE 33

5-Ethoxy-1,3-dihydro-3-[2-(N,N-diisopropylamino)ethyl]-1-(2,4-dimethoxybenzenesulfonyl)-2H-benzimidazol-2-one 0.05 g of sodium hydride as a 60% dispersion in oil is added in portions to a solution of 0.5 g of 5-ethoxy-1,3-dihydro-3-[2-(N,N-diisopropylamino)ethyl]-2H-benzimidazol-2-one in 7 ml of THF and the mixture is stirred for 30 minutes at RT. 0.42 g of 2,4-dimethoxybenzenesulfonyl chloride is then added and the mixture is stirred for 1 hour at RT. The solvent is evaporated off under vacuum, the residue is taken up with water, extracted with AcOEt, washed with water and dried over Na₂SO₄ and the solvent is evaporated off under vacuum to give 0.7 g of the expected product after crystallization from iso ether. M.p.=132° C.

EXAMPLE 34

5-Ethoxy-1,3-dihydro-1-(2,4-dimethoxybenzenesulfonyl)-3-[2-(morpholin-4-yl)ethyl]-2H-benzimidazol-2-one This compound is prepared by the procedure described in EXAMPLE 33 starting from 0.6 g of 5-ethoxy-1,3-dihydro-3-[2-(morpholin-4-yl)ethyl]-2H-benzimidazol-2-one. 0.75 g of the expected product is obtained after crystallization from ether. M.p.=146°–149° C.

EXAMPLE 35

1-[4-(N'-tert-Butylureido)-2-methoxybenzenesulfonyl]-3-cyclohexyl-5-ethoxy-1,3-dihydro-2H-benzimidazol-2-one A mixture of 0.7 g of the compound obtained in EXAMPLE 16 step A), 1 ml of tert-butylamine and 25 ml of DCM is stirred for 48 hours at RT. The solvent is evaporated off under vacuum and the residue is chromatographed on silica using a DCM/AcOEt mixture (90/10; v/v) as the eluent to give 0.41 g of the expected product after crystallization from an AcOEt/iso ether mixture (50/50; v/v). M.p.=237° C.

EXAMPLE 36

1-[4-(N'-tert-Butyl-N'-methylureido)-2-methoxybenzenesulfonyl]-3-cyclohexyl-5-ethoxy-1,3-dihydro-2H-benzimidazol-2-one A mixture of 0.5 g of the compound obtained in EXAMPLE 16 step A), 1 ml of N-methyl-tert-butylamine and 20 ml of DCM is stirred for 2 hours at RT. The solvent is evaporated off under vacuum and the residue is chromatographed on silica using a DCM/AcOEt mixture (95/5; v/v) as the eluent to give 0.13 g of the expected product after crystallization from an iso ether/ AcOEt mixture (65/35; v/v). M.p.=208° C.

EXAMPLE 37

5-Ethoxy-1-[4-(N',N'-diethylureido)-2-methoxybenzenesulfonyl]-1,3-dihydro-3-(1,1,3,3-tetramethylbutyl)-2H-benzimidazol-2-one A) 5-Ethoxy-1,3-dihydro-1-(2-methoxy-4-nitrobenzenesulfonyl)-3-(1,1,3,3-tetramethylbutyl)-2H-benzimidazol-2-one 0.2 g of sodium hydride as a 60% dispersion in oil is added in portions to a solution of 1 g of 5-ethoxy-1,3-dihydro-3-(1,1,3,3-tetramethylbutyl)-2H- benzimidazol-2-one in 10 ml of THF and 20 ml of DMF and the mixture is stirred for 30 minutes at RT. 1.2 g of 2-methoxy-4-nitrobenzenesulfonyl chloride are then added and the mixture is stirred for 5 hours at RT. The reaction mixture is poured into 200 ml of water, extracted with AcOEt, washed with water and dried over $Na_2SO_4$ and the solvent is evaporated off under vacuum to give 1.1 g of the expected product after crystallization from iso ether. M.p.=158° C.

B) 1-(4-Amino-2-methoxybenzenesulfonyl)-5-ethoxy-1,3-dihydro-3-(1,1,3,3-tetramethylbutyl)-2H-benzimidazol-2-one A mixture of 1.1 g of the compound obtained in the previous step and 0.2 g of 5% palladium-on-charcoal in 200 ml of AcOEt is hydrogenated at RT and at atmospheric pressure. The catalyst is filtered off on Célite® and the filtrate is evaporated under vacuum to give 0.56 g of the expected product. M.p.=216° C.

C) 5-Ethoxy-1,3-dihydro-1-[2-methoxy-4-(phenoxycarboxamido)benzenesulfonyl]-3-(1,1,3,3-tetramethylbutyl)-2H-benzimidazol-2-one A solution of 0.25 g of NaOH pellets in 10 ml of water is added to a solution of 0.52 g of the compound obtained in the previous step in 30 ml of THF. 1 ml of phenyl chloroformate is then added and the mixture is stirred for 5 hours at RT. The reaction mixture is evaporated under vacuum, the residue is taken up with water, extracted with AcOEt, washed with water and dried over $Na_2SO_4$ and the solvent is evaporated off under vacuum to give 0.69 g of the expected product after crystallization from iso ether. M.p.=168° C.

D) 5-Ethoxy-1-[4-(N',N'-diethylureido)-2-methoxybenzenesulfonyl]-1,3-dihydro-3-(1,1,3,3-tetramethylbutyl)-2H-benzimidazol-2-one 1 ml of diethylamine is added to a solution of 0.67 g of the compound obtained in the previous step in 20 ml of DCM and the mixture is stirred for 6 hours at RT. The reaction mixture is diluted with DCM, washed with a 1N solution of HCl, with a 1N solution of NaOH and with water and dried over $Na_2SO_4$ and the solvent is evaporated off under vacuum. The residue is chromatographed on silica using a DCM/MeOH mixture (99/1; v/v) as the eluent to give 0.33 g of the expected product after crystallization from iso ether. M.p.=225° C.

EXAMPLE 38

5-Ethoxy-1-[4-(N',N'-diethylureido)-2-methoxybenzenesulfonyl]-1,3-dihydro-3-(4(a,e)-methylcyclohexyl)-2H-benzimidazol-2-one A) 5-Ethoxy-1,3-dihydro-1-(2-methoxy-4-nitrobenzenesulfonyl)-3-(4(a,e)-methylcyclohexyl)-2H-benzimidazol-2-one This compound is prepared by the procedure described in EXAMPLE 37 step A) starting from 1.4 g of 5-ethoxy-1,3-dihydro-3-(4(a,e)-methylcyclohexyl)-2H-benzimidazol-2-one and 1.5 ml of 2-methoxy-4-nitrobenzenesulfonyl chloride in 30 ml of DMF. 2 g of the expected product are obtained after crystallization from iso ether. M.p.=147° C.

B) 1-(4-Amino-2-methoxybenzenesulfonyl)-5-ethoxy-1,3-dihydro-3-(4(a,e)-methylcyclohexyl)-2H-benzimidazol-2-one A mixture of 2 g of the compound obtained in the previous step in 50 ml of 95° EtOH and 1.5 g of Raney® nickel is hydrogenated at RT under a pressure of 30 bar. The catalyst is filtered off on Célite® and the filtrate is evaporated under vacuum to give 0.5 g of the expected product. M.p.=126° C.

C) 5-Ethoxy-1,3-dihydro-1-[2-methoxy-4-(phenoxycarboxamido)benzenesulfonyl]-3-(4(a,e)-methylcyclohexyl)-2H-benzimidazol-2-one This compound is prepared by the procedure described in EXAMPLE 37 step C) starting from 0.5 g of the compound obtained in the previous step and 1.5 ml of phenyl chloroformate. 0.44 g of the expected product is obtained after crystallization from iso ether. M.p.=193° C.

D) 5-Ethoxy-1-[4-(N',N'-diethylureido)-2-methoxybenzenesulfonyl]-1,3-dihydro-3-(4(a,e)-methylcyclohexyl)-2H-benzimidazol-2-one 2 ml of diethylamine are added to a solution of 0.43 g of the compound obtained in the previous step in 30 ml of DCM and the mixture is stirred overnight at RT. The reaction mixture is evaporated under vacuum and the residue is chromatographed on silica using a DCM/AcOEt mixture (80/20; v/v) as the eluent to give 0.345 g of the expected product after crystallization from iso ether. M.p.=206° C.

EXAMPLE 39

5-Ethoxy-1-[4-(N',N'-diethylureido)-2-methoxybenzenesulfonyl]-1,3-dihydro-3-(4(a,e)-hydroxycyclohexyl)-2H-benzimidazol-2-one A) 5-Ethoxy-1,3-dihydro-3-[4(a,e)-(tetrahydropyran-2(R,S)-yloxy)cyclohexyl]-1-(2-methoxy-4-nitrobenzenesulfonyl)-2H-benzimidazol-2-one This compound is prepared by the procedure described in EXAMPLE 37 step A) starting from 1.45 g of 5-ethoxy-1,3-dihydro-3-[4(a,e)-(tetrahydropyran-2(R,S)-yloxy)cyclohexyl]- 2H-benzimidazol-2-one and 1.1 g of 2-methoxy-4-nitrobenzenesulfonyl chloride. This gives 2.5 g of an oil, which crystallizes. M.p.=132°–136° C.

B) 1-(4-Amino-2-methoxybenzenesulfonyl)-5-ethoxy-1,3-dihydro-3-[4(a,e)-(tetrahydropyran-2(R,S)-yloxy)cyclohexyl]-2H-benzimidazol-2-one A mixture of 2.4 g of the compound obtained in the previous step and 2 g of Raney® nickel in 30 ml of THF and 20 ml of MeOH is hydrogenated at 30° C. and at atmospheric pressure. The catalyst is filtered off and washed with DCM and the filtrate is concentrated under vacuum to give 2.2 g of the expected product, which is used as such in the next step.

C) 5-Ethoxy-1,3-dihydro-3-[4(a,e)-tetrahydropyran-2(R,S)-yloxy)cyclohexyl]-1-[2-methoxy-4-(phenoxycarboxamido)benzenesulfonyl]-2H-benzimidazol-2-one A mixture of 2.1 g of the compound obtained in the previous step and 3 ml of triethylamine in 10 ml of THF is cooled to 5° C. and a solution of 2 ml of phenyl chloroformate in 5 ml of THF is added. The reaction mixture is stirred for 3 hours at RT and evaporated under vacuum. The residue is taken up with water, extracted with AcOEt, washed with a saturated solution of $NaHCO_3$ and with water and dried over $Na_2SO_4$ and the solvent is evaporated off under vacuum to give 2.5 g of the expected product after crystallization from iso ether.

D) 5-Ethoxy-1-[4-(N',N'-diethylureido)-2-methoxybenzenesulfonyl]-1,3-dihydro-3-(4(a,e)-hydroxycyclohexyl)-2H-benzimidazol-2-one A mixture of 2.4 g of the compound obtained in the previous step and 8 g of diethylamine in 30 ml of THF is stirred for 20 hours at RT. It is evaporated under vacuum to give a yellow oil. This oil is dissolved in 20 ml of 96° EtOH, 2 ml of concentrated HCl are added and the mixture is then stirred for 2 hours at RT. The reaction mixture is evaporated under vacuum at 40° C., the residue is taken up with water, extracted with AcOEt, washed with a 1N solution of HCl, with water, with a 1N solution of NaOH and with water and dried over $Na_2SO_4$ and the solvent is evaporated off under vacuum to give 1.8 g of the expected product after crystallization from iso ether. M.p.=221° C.

EXAMPLE 40

3-(Adamant-1-yl)-5-ethoxy-1-[4-(N',N'-diethylureido)-2-methoxybenzenesulfonyl]-1,3-dihydro-2H-benzimidazol-2-one A) 3-(Adamant-1-yl)-5-ethoxy-1,3-dihydro-1-(2-methoxy-4-nitrobenzenesulfonyl)-2H-benzimidazol-2-one 0.35 g of sodium hydride as a 60% dispersion in oil is added in portions to a suspension of 2.5 g of 3-(adamant-1-yl)-5-ethoxy-1,3-dihydro-2H-benzimidazol-2-one in 10 ml of THF and 20 ml of DMF and the mixture is stirred for 30 minutes at RT. 2.2 g of 2-methoxy-4-nitrobenzenesulfonyl chloride are then added and the formation of a yellow precipitate is observed. The reaction mixture is poured into iced water and the precipitate obtained is filtered off and washed with water, with 95° EtOH and with ether to give 3.8 g of the expected product. M.p.=231° C.

B) 3-(Adamant-1-yl)-1-(4-amino-2-methoxybenzenesulfonyl)-5-ethoxy-1,3-dihydro-2H-benzimidazol-2-one A mixture of 3.8 g of the compound obtained in the previous step, 5 g of iron powder, 120 ml of 95° EtOH and 2 ml of water is heated to the reflux point and 2 ml of concentrated HCl are added dropwise. The mixture is refluxed for 2 hours and then, after cooling, 300 ml of AcOEt are added, the mixture is filtered on Célite® and the material on the filter is washed with AcOEt. After decantation of the filtrate, the organic phase is dried over $Na_2SO_4$ and the solvent is concentrated until the product precipitates. The precipitate is filtered off and washed with iso ether to give 1.5 g of the expected product. M.p.=248° C.

C) 3-(Adamant-1-yl)-5-ethoxy-1,3-dihydro-1-[2-methoxy-4-(phenoxycarboxamido)benzenesulfonyl]2H-benzimidazol-2-one A mixture of 0.5 g of the compound obtained in the previous step and 20 ml of THF is cooled to 10° C. and a solution of 0.06 g of NaOH pellets in 1 ml of water is added, followed by 0.6 ml of phenyl chloroformate. The mixture is stirred for 18 hours at RT and the solvent is evaporated off under vacuum. The residue is taken up with water and the precipitate formed is filtered off and washed with AcOEt to give 0.56 g of the expected product. M.p.=239° C.

D) 3-(Adamant-1-yl)-5-ethoxy-1-[4-(N',N'-diethylureido)-2-methoxybenzenesulfonyl]1,3-dihydro-2H-benzimidazol-2-one 2 ml of diethylamine are added to a solution of 0.55 g of the compound obtained in the previous step in 20 ml of DCM and the mixture is stirred for 3 hours at RT. The reaction mixture is washed with water and dried over $Na_2SO_4$ and the solvent is evaporated off under vacuum to give 0.36 g of the expected product after crystallization from AcOEt. M.p.=221° C.

EXAMPLE 41

3-(Adamant-1-yl)-5-ethoxy-1-[4-(3,3-diethylguanidino)-2-methoxybenzenesulfonyl]-1,3-dihydro-2H-benzimidazol-2-one hydrochloride monohydrate A mixture of 1.5 g of the compound obtained in EXAMPLE 40 step B), 1.5 g of N,N-diethylcyanamide, 20 ml of AcOEt and 3 ml of a 20% solution of HCl in EtOH is refluxed for 22 hours. 2 g of N,N-diethylcyanamide and 3 ml of a 20% solution of HCl in EtOH are then added and reflux is continued for 5 hours. After cooling, the reaction mixture is extracted with AcOEt, the organic phase is washed with water, with a 1N solution of $NaHCO_3$ and with water and dried over $Na_2SO_4$ and the solvent is evaporated off under vacuum. The residue is chromatographed on silica using a DCM/AcOEt mixture (94/6; v/v) as the eluent. The product obtained is dissolved in EtOH, 1 ml of concentrated HCl is added and the mixture is evaporated under vacuum to give 0.2 g of the hydrochloride of the expected product after crystallization from an EtOH/ether mixture (50/50; v/v). M.p.=186° C.

EXAMPLE 42

5-Chloro-3-(2-chlorophenyl)-1-[4-(N',N'-diethylureido)benzenesulfonyl]-1,3-dihydro-2H-benzimidazol-2-one 0.075 g of sodium hydride as a 60% dispersion in oil is added to a solution of 0.5 g of 5-chloro-3-(2-chlorophenyl)-1,3-dihydro-2H-benzimidazol-2-one in 40 ml of DMF and the mixture is stirred for 30 minutes at RT. 0.6 g of 4-(N',N'-diethylureido)benzenesulfonyl chloride is then added and the mixture is stirred for 4 hours at RT. The reaction mixture is poured into iced water, extracted with AcOEt, washed with water and dried over $Na_2SO_4$ and the solvent is evaporated off under vacuum. The residue is chromatographed on silica using a DCM/AcOEt mixture (95/5; v/v) as the eluent to give 0.45 g of the expected product. M.p.=222° C.

EXAMPLE 43

5-Ethoxy-1,3-dihydro-1-[4-(N',N'-diethylureido)-2-methoxybenzenesulfonyl]-3-(pyrid-2-yl)-2H-benzimidazol-2-one A) 5-Ethoxy-1,3-dihydro-1-(2-methoxy-4-nitrobenzenesulfonyl)-3-(pyrid-2-yl)-2H-benzimidazol-2-one This compound is prepared by the procedure described in EXAMPLE 37 step A) starting from 1 g of 5- ethoxy-1,3-dihydro-3-(pyrid-2-yl)-2H-benzimidazol-2-one and 1.2 g of 2-methoxy-4-nitrobenzenesulfonyl chloride. 1.2 g of the expected product are obtained after crystallization from iso ether. M.p.=175° C.

B) 1-(4-Amino-2-methoxybenzenesulfonyl)-5-ethoxy-1,3-dihydro-3-(pyrid-2-yl)-2H-benzimidazol-2-one A mixture of 1.2 g of the compound obtained in the previous step and 0.2 g of 5% palladium-on- charcoal in 200 ml of AcOEt is hydrogenated at RT and at atmospheric pressure. The catalyst is filtered off and the filtrate is evaporated under vacuum to give 0.82 g of the expected product after crystallization from iso ether. M.p.=208° C.

C) 5-Ethoxy-1,3-dihydro-1-[2-methoxy-4-(phenoxycarboxamido)benzenesulfonyl]-3-(pyrid-2-yl)-2H-benzimidazol-2-one A solution of 0.1 g of NaOH pellets in 20 ml of water is added to a solution of 0.82 g of the compound obtained in the previous step in 10 ml of THF. 1.5 ml of phenyl chloroformate are then added and the mixture is stirred for 2 hours at RT. The reaction mixture is extracted with AcOEt, washed with water and dried over $Na_2SO_4$ and the solvent is evaporated off under vacuum to give 0.7 g of the expected product, which is used as such in the next step.

D) 5-Ethoxy-1,3-dihydro-1-[4-(N',N'-diethylureido)-2methoxybenzenesulfonyl]-3-(pyrid-2-yl)-2H-benzimidazol-2-one 1 ml of diethylamine is added to a solution of 0.7 g of the compound obtained in the previous step in 20 ml of DCM and the mixture is stirred for 3 hours at RT. The reaction mixture is concentrated under vacuum, the residue is extracted with AcOEt, washed with a 1N solution of HCl and dried over $Na_2SO_4$ and the solvent is evaporated off under vacuum. The residue is chromatographed on silica using a DCM/MeOH mixture (99/1; v/v) as the eluent to give 0.32 g of the expected product after crystallization from an AcOEt/iso ether mixture. M.p.=171° C.

The compounds according to the invention collated in TABLE 3 below are prepared by the procedures described in the above EXAMPLES starting from the 1,3- dihydro-2H-benzimidazol-2-ones described in the above Preparations.

TABLE 3

| Examples | R₁ | R₃ | R₅ | R₆ | m.p. °C. crystallisation solvent |
|---|---|---|---|---|---|
| *44 (1) | —OEt | cyclohexyl | 2-OMe | 4-NHCON(Et)(iPr) | 197 iso ether/AcOEt |
| *45 (2) | —OEt | cyclohexyl | 2-OMe | 4-NHCON-(2,6-diMe-cyclohexyl) | 234 iso ether |
| *46 (3) | —OEt | —C(Me)₂—CH₂—OMe | 2-OMe | 4-NH₂ | 213 |
| *47 (4) | —OEt | —C(Me)₂—CH₂—OMe | 2-OMe | 4-NHCON(Et)₂ | 211 |
| *48 (5) | —OEt | cyclohexyl-OMe (a,e) | 2-OMe | 4-NO₂ | 108–111 |
| *49 (6) | —OEt | cyclohexyl-OMe (a,e) | 2-OMe | 4-NHCOO-Ph | 167–170 iso ether |
| *50 (7) | —OEt | cyclohexyl-OMe (a,e) | 2-OMe | 4-NHCON(Et)₂ | 215–217 iso ether |
| *51 (5) | —OEt | cyclohexyl-O—CH₂CH₂—OMe (a,e) | 2-OMe | 4-NO₂ | 136–138 |
| *52 (6) | —OEt | cyclohexyl-O—CH₂CH₂—OMe (a,e) | 2-OMe | 4-NHCOO-Ph | 150–153 iso ether |
| *53 (7) | —OEt | cyclohexyl-O—CH₂CH₂—OMe (a,e) | 2-OMe | 4-NHCON(Et)₂ | 138–140 iso ether |

TABLE 3-continued

| | | | | | |
|---|---|---|---|---|---|
| *54 (5) | —OEt | cyclohexyl-N(Me)Me (a,e) | 2-OMe | 4-NO$_2$ | 185 |
| *55 (8) | —OEt | cyclohexyl-N(Me)Me (a,e) | 2-OMe | 4-NH$_2$ | 253 |
| *56 (9) | —OEt | cyclohexyl-N(Me)Me (a,e) | 2-OMe | 4-NHCOO—Ph | 230–234 iso ether |
| *57 (10) | —OEt | cyclohexyl-N(Me)Me (a,e) | 2-OMe | 4-NHCON(Et)Et | 217–218 iso ether |
| *58 (5) | —OEt | N-Me piperazinyl | 2-OMe | 4-NO$_2$ | 200 iso ether |
| *59 (11) | —OEt | N-Me piperazinyl | 2-OMe | 4-NHCOO—Ph | 136 |
| *60 (12) | —OEt | N-Me piperazinyl | 2-OMe | 4-NHCON(Et)Et | 151 iso ether |
| *61 (5) | —OEt | morpholinyl | 2-OMe | 4-NO$_2$ | 193 EtOH |
| *62 (13) | —OEt | morpholinyl | 2-OMe | 4-NH$_2$ | 209 |
| *63 (14) | —OEt | morpholinyl | 2-OMe | 4-NHCOO—Ph | 215 |

TABLE 3-continued

| | | | | | |
|---|---|---|---|---|---|
| *64 (7) | —OEt | 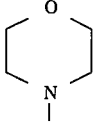 | 2-OMe | 4-NHCON(Et)(Et) | 242 |
| *65 (3) | —OEt |  | 2-OMe | 4-NH$_2$ | 192 |
| *66 (14) | —OEt | 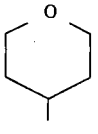 | 2-OMe | 4-NHCOO-phenyl | 215 |
| *67 (7) | —OEt | 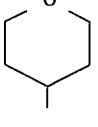 | 2-OMe | 4-NHCON(Et)(Et) | 201 |
| *68 (5) | —OEt | —CH$_2$CH$_2$—N(iPr)(iPr) | 2-OMe | 4-NO$_2$ | 172 iso ether |
| *69 (15) | —OEt | —CH$_2$CH$_2$—N(iPr)(iPr) | 2-OMe | 4-NH$_2$ | 177 |
| *70 (14) | —OEt | —CH$_2$CH$_2$—N(iPr)(iPr) | 2-OMe | 4-NHCOO-phenyl | 135–137 iso ether |
| *71 (7) | —OEt | —CH$_2$CH$_2$—N(iPr)(iPr) | 2-OMe | 4-NHCON(Et)(Et) | 168 iso ether |
| *72 (5) | —OEt | 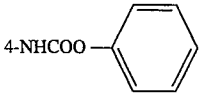 | 2-OMe | 4-NO$_2$ | 156 iso ether |
| *73 (16) | —OEt | 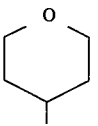 | 2-OMe | 4-NH$_2$ | 214 |
| *74 (14) | —OEt | 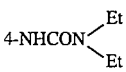 | 2-OMe | 4-NHCOO-phenyl | 138 iso ether |
| *75 (12) | —OEt | 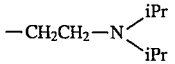 | 2-OMe | 4-NHCON(Et)(Et) | 235 iso ether |
| *76 (5) | —OEt | 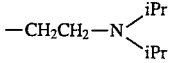 | 2-OMe | 4-NO$_2$ | 165 iso ether |

TABLE 3-continued
| | | | | | |
|---|---|---|---|---|---|
| *77 (17) | —OEt | 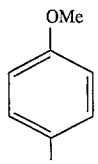 | 2-OMe | 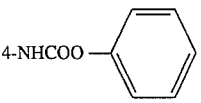 4-NHCOO— | 186 iso ether |
| *78 (7) | —OEt | 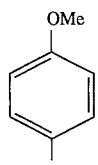 | 2-OMe | 4-NHCON(Et)(Et) | 157 iso ether |
| *79 (5) | —OEt | 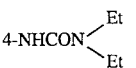 iPr | 2-OMe | 4-NO$_2$ | 134–138 iso ether |
| *80 (18) | —OEt | 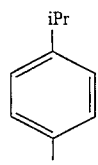 iPr | 2-OMe | 4-NH$_2$ | 108–115 |
| *81 (14) | —OEt | 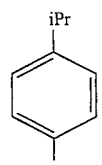 iPr | 2-OMe | 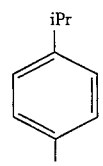 4-NHCOO— | 202–205 iso ether |
| *82 (19) | —OEt | 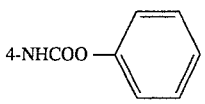 iPr | 2-OMe | 4-NHCON(Et)(Et) | 203 iso ether |
| *83 (5) | —OEt | 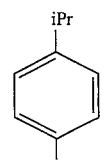 | 2-OMe | 4-NO$_2$ | 187 |
| *84 (20) | —OEt |  | 2-OMe | 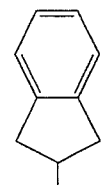 4-NHCOO— | 198 iso ether/EtOH |
| *85 (7) | —OEt | 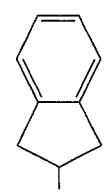 | 2-OMe | 4-NHCON(Et)(Et) | 207 |
| *86 (21) | —OCH$_2$CH$_2$—OMe | 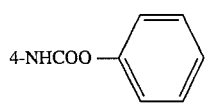 | 2-OMe | 4-NO$_2$ | 168 |

TABLE 3-continued

| | | | | | |
|---|---|---|---|---|---|
| *87 (18) | OCH$_2$CH$_2$—OMe | (cyclohexyl, zigzag) | 2-OMe | 4-NH$_2$ | 193 |
| *88 (4) | OCH$_2$CH$_2$—OMe | (cyclohexyl, zigzag) | 2-OMe | 4-NHCON(Et)(Et) | 205 iso ether |
| *89 (5) | —O-(tetrahydrofuryl) | (cyclohexyl, zigzag) | 2-OMe | 4-NO$_2$ | 113 |
| *90 (16) | —O-(tetrahydrofuryl) | (cyclohexyl, zigzag) | 2-OMe | 4-NH$_2$ | 130 |
| *91 (4) | —O-(tetrahydrofuryl) | (cyclohexyl, zigzag) | 2-OMe | 4-NHCON(Et)(Et) | 222 iso ether |
| *92 (5) | —OEt | (cyclohexyl) | 2-OMe | 4-NO$_2$ | 154 |
| *93 (22) | —OEt | (cyclohexyl) | 2-OMe | 4-NH$_2$ | 224 iso ether |
| *94 (4) | —OEt | (cyclohexyl) | 2-OMe | 4-NHCON(Et)(Et) | 208 iso ether |
| *95 (21) | —OEt | (cyclopentyl) | 2-OMe | 4-NO$_2$ | 139 |
| *96 (23) | —OEt | (cyclopentyl) | 2-OMe | 4-NH$_2$ | 198 |
| *97 (14) | —OEt | (cyclopentyl) | 2-OMe | 4-NHCOO-phenyl | 195 iso ether |
| *98 (12) | —OEt | (cyclopentyl) | 2-OMe | 4-NHCON(Et)(Et) | 204 AcOEt/iso ether |

(1) This compound is prepared by the procedure described in EXAMPLE 35 using N-ethylisopropylamine.
(2) This compound is prepared by the procedure described in EXAMPLE 35 using cis-2,6-dimethylpiperidine.
(3) This compound is prepared by the procedures described in EXAMPLE 37 step A) and then step B).
(4) This compound is prepared by the procedures described in EXAMPLE 37 step C) and then step D).
(5) This compound is prepared by the procedure described in EXAMPLE 37 step A).
(6) This compound is prepared by the procedures described in EXAMPLE 38 step B) (hydrogenation under a pressure of 70 bar) and then in EXAMPLE 37 step C).
(7) This compound is prepared by the procedure described in EXAMPLE 37 step D).
(8) A mixture of 2.9 g of the compound of EXAMPLE 54 in 30 ml of THF and 30 ml of MeOH and 1 g of Raney® nickel is hydrogenated at RT and at atmospheric pressure. The catalyst is filtered off and the filtrate is evaporated under vacuum.
(9) 1.3 g of the compound of EXAMPLE 55 are dissolved at 10° C. in 5 ml of phenyl chloroformate and the solution is stirred for 1 hour at 10–15° C. The reaction mixture is concentrated at 40° C. under 0.1 mm Hg, the residue is taken up with iced water, neutralized by the addition of concentrated NaOH, extracted with AcOEt and dried over Na$_2$SO$_4$ and the solvent is evaporated off under vacuum to give 0.7 g of the expected product.
(10) A mixture of 0.68 g of the compound of EXAMPLE 56, 2 g of diethylamine, 20 ml of THF and 20 ml of EtOH is heated at 40° C. until a solution is formed. This is stirred for 20 hours at RT. The precipitate formed is filtered off and washed with iso ether to give 0.38 g of the expected product.
(11) This compound is prepared by the procedures described in EXAMPLE 38 step B) and then in EXAMPLE 37 step C).
(12) This compound is prepared by the procedure described in EXAMPLE 38 step D).
(13) This compound is prepared by the procedure described in EXAMPLE 37 step B).
(14) This compound is prepared by the procedure described in EXAMPLE 37 step C).

TABLE 3-continued

(15) This compound is prepared by the procedure described in EXAMPLE 38 step B) (hydrogenation under a pressure of 50 bar).
(16) This compound is prepared by the procedure described in EXAMPLE 38 step B) (hydrogenation at atmospheric pressure).
(17) This compound is prepared by the procedures described in reference (8) and then in EXAMPLE 37 step C).
(18) This compound is prepared by the procedure described in reference (8) starting from the corresponding nitro derivative.
(19) A mixture of 1.1 g of the compound of EXAMPLE 81 and 5 ml of diethylamine in 20 ml of THF is stirred for 2 hours at RT.
It is evaporated under vacuum, the residue is extracted with AcOEt, washed with 1 N NaOH, with water, with 1 N HCl and
with water and dried over $Na_2SO_4$ and the solvent is evaporated off under vacuum.
The residue is chromatographed on silica using a DCM/AcOEt mixture (80/20; v/v) as the eluent.
(20) This compound is prepared by the procedures described in EXAMPLE 37 step B) and then step C).
(21) This compound is prepared by the procedure described in EXAMPLE 40 step A).
(22) A mixture of 0.8 g of the compound of EXAMPLE 92, 100 ml of 96° EtOH, 20 ml of AcOEt and 50 ml of MeOH is hydrogenated
at RT under a pressure of 2 bar in the presence of 0.5 g of Raney® nickel. The catalyst is filtered off and
the filtrate is evaporated under vacuum.
(23) A mixture of 1.4 g of the compound of EXAMPLE 95, 250 ml of 95° EtOH and 100 ml of AcOEt is hydrogenated
at RT under a pressure of 2 bar in the presence of Raney® nickel. The catalyst is filtered off and the filtrate is
evaporated under vacuum to give 1.1 g of the expected product.

(1) This compound is prepared by the procedure described in EXAMPLE 35 using N-ethylisopropylamine.

(2) This compound is prepared by the procedure described in EXAMPLE 35 using cis-2,6-dimethylpiperidine.

(3) This compound is prepared by the procedures described in EXAMPLE 37 step A) and then step B).

(4) This compound is prepared by the procedures described in EXAMPLE 37 step C) and then step D).

(5) This compound is prepared by the procedure described in EXAMPLE 37 step A).

(6) This compound is prepared by the procedures described in EXAMPLE 38 step B) (hydrogenation under a pressure of 70 bar) and then in EXAMPLE 37 step C).

(7) This compound is prepared by the procedure described in EXAMPLE 37 step D).

(8) A mixture of 2.9 g of the compound of EXAMPLE 54 in 30 ml of THF and 30 ml of MeOH and 1 g of Raney® nickel is hydrogenated at RT and at atmospheric pressure. The catalyst is filtered off and the filtrate is evaporated under vacuum.

(9) 1.3 g of the compound of EXAMPLE 55 are dissolved at 10° C. in 5 ml of phenyl chloroformate and the solution is stirred for 1 hour at 10°–15° C. The reaction mixture is concentrated at 40° C. under 0.1 mm Hg, the residue is taken up with iced water, neutralized by the addition of concentrated NaOH, extracted with AcOEt and dried over $Na_2SO_4$ and the solvent is evaporated off under vacuum to give 0.7 g of the expected product.

(10) A mixture of 0.68 g of the compound of EXAMPLE 56, 2 g of diethylamine, 20 ml of THF and 20 ml of EtOH is heated at 40° C. until a solution is formed. This is stirred for 20 hours at RT. The precipitate formed is filtered off and washed with iso ether to give 0.38 g of the expected product.

(11) This compound is prepared by the procedures described in EXAMPLE 38 step B) and then in EXAMPLE 37 step C).

(12) This compound is prepared by the procedure described in EXAMPLE 38 step D).

(13) This compound is prepared by the procedure described in EXAMPLE 37 step B).

(14) This compound is prepared by the procedure described in EXAMPLE 37 step C).

(15) This compound is prepared by the procedure described in EXAMPLE 38 step B) (hydrogenation under a pressure of 50 bar).

(16) This compound is prepared by the procedure described in EXAMPLE 38 step B) (hydrogenation at atmospheric pressure).

(17) This compound is prepared by the procedures described in reference (8) and then in EXAMPLE 37 step C).

(18) This compound is prepared by the procedure described in reference (8) starting from the corresponding nitro derivative.

(19) A mixture of 1.1 g of the compound of EXAMPLE 81 and 5 ml of diethylamine in 20 ml of THF is stirred for 2 hours at RT. It is evaporated under vacuum, the residue is extracted with AcOEt, washed with 1N NaOH, with water, with 1N HCl and with water and dried over $Na_2SO_4$ and the solvent is evaporated off under vacuum. The residue is chromatographed on silica using a DCM/AcOEt mixture (80/20; v/v) as the eluent.

(20) This compound is prepared by the procedures described in EXAMPLE 37 step B) and then step C).

(21) This compound is prepared by the procedure described in EXAMPLE 40 step A).

(22) A mixture of 0.8 g of the compound of EXAMPLE 92, 100 ml of 96° EtOH, 20 ml of AcOEt and 50 ml of MeOH is hydrogenated at RT under a pressure of 2 bar in the presence of 0.5 g of Raney® nickel. The catalyst is filtered off and the filtrate is evaporated under vacuum.

(23) A mixture of 1.4 g of the compound of EXAMPLE 95, 250 ml of 95° EtOH and 100 ml of AcOEt is hydrogenated at RT under a pressure of 2 bar in the presence of Raney® nickel. The catalyst is filtered off and the filtrate is evaporated under vacuum to give 1.1 g of the expected product.

EXAMPLE 99

3-Cyclohexyl-5-ethoxy-1,3-dihydro-1-[2-methoxy-4-[N-(1,1-dimethylpropyl)carbamoyl]benzenesulfonyl]-2H-benzimidazol-2-one A mixture of 1.09 g of the compound obtained in EXAMPLE 13, 1 ml of 1,1-dimethylpropylamine, 1.2 g of BOP, 1 ml of DIPEA and 20 ml of DCM is stirred for 2 hours at RT. The reaction mixture is evaporated under vacuum, the residue is extracted with AcOEt, washed with a 1N solution of HCl, with a 1N solution of NaOH and with water and dried over $Na_2SO_4$ and the solvent is evaporated off under vacuum. The residue is chromatographed on silica using a DCM/AcOEt mixture (99/1; v/v) as the eluent to give 0.88 g of the expected product in the form of white crystals. M.p.=219° C.

EXAMPLE 100

3-Cyclohexyl-5-ethoxy-1,3-dihydro-1-[2-methoxy-4-[N-(1,1,3,3-tetramethylbutyl)carbamoyl]benzenesulfonyl]-2H-benzimidazol-2-one A mixture of 0.620 g of the compound obtained in EXAMPLE 13, 1 ml of 1,1,3,3-tetramethylbutylamine, 0.7 g of BOP, 1 ml of DIPEA and 20 ml of DCM is stirred for 2 hours at RT. The reaction mixture is then washed with water, with a 1N solution of HCl and with a 1N solution of NaOH and dried over $Na_2SO_4$ and the solvent is evaporated off under vacuum. The residue is chromatographed on silica using DCM as the eluent to give 0.28 g of the expected product in the form of white crystals. M.p.=180° C.

EXAMPLE 101

3-Cyclohexyl-5-ethoxy-1,3-dihydro-1-[4-[N-(2-hydroxy-1,1-dimethylethyl)carbamoyl]-2-methoxybenzenesulfonyl]-2H-benzimidazol-2-one This compound is prepared by the procedure described in EXAMPLE 100 starting from 0.5 g of the compound obtained in EXAMPLE 13, 0.5 g of 2-amino-2- methylpropan-1-ol, 0.6 g of BOP, 1 ml of DIPEA and 20 ml of DCM. It is chromatographed on silica using a DCM/MeOH mixture (99/1; v/v) as the eluent to give 0.12 g of the expected product in the form of white crystals. M.p.=218° C.

EXAMPLE 102

3-Cyclohexyl-5-ethoxy-1,3-dihydro-1-[2-methoxy-4-[N-(2-methylphenyl)carbamoyl]benzenesulfonyl]-2H-benzimidazol-2-one A mixture of 0.44 g of the compound obtained in EXAMPLE 13 and 0.17 g of thionyl chloride in 1 ml of DMF and 20 ml of DCM is refluxed for 6 hours. The reaction mixture is evaporated under vacuum, 0.6 g of o-toluidine in 20 ml of DCM is added to the resulting acid chloride and the mixture is stirred for 1 hour at RT. The solvent is evaporated off under vacuum, the residue is extracted with AcOEt, washed twice with a 12N solution of HCl, with a 3N solution of NaOH and with water and dried over $Na_2SO_4$ and the solvent is evaporated off under vacuum. The residue is chromatographed on silica using a DCM/AcOEt mixture (98/2; v/v) as the eluent to give 0.14 g of the expected product in the form of white crystals. M.p.=179° C.

EXAMPLE 103

3-Cyclohexyl-5-ethoxy-1,3-dihydro-1-[2-methoxy-4-[N-(thiazol-2-yl)carbamoyl]benzenesulfonyl]-2H-benzimidazol-2-one This compound is prepared by the procedure described in EXAMPLE 100 starting from 1 g of the compound obtained in EXAMPLE 13, 0.3 g of 2-aminothiazole, 1.2 g of BOP, 1 ml of DIPEA and 20 ml of DCM. It is chromatographed on silica using a DCM/MeOH mixture (99.5/0.5; v/v) as the eluent to give 0.09 g of the expected product after crystallization from EtOH. M.p.=213° C.

EXAMPLE 104

3-Cyclohexyl-5-ethoxy-1,3-dihydro-1-[4-[N-(indan-2-yl)carbamoyl]-2-methoxybenzenesulfonyl]-2H-benzimidazol-2-one This compound is prepared by the procedure described in EXAMPLE 100 starting from 0.8 g of the compound obtained in EXAMPLE 13, 0.35 g of 2-aminoindane hydrochloride, 0.8 g of BOP, 2 ml of DIPEA and 20 ml of DCM. It is chromatographed on silica using a DCM/AcOEt mixture (96/4; v/v) as the eluent to give 0.7 g of the expected product in the form of white crystals. M.p.=160° C.

EXAMPLE 105

1-[4-[N-(Adamant-1-yl)carbamoyl]-2-methoxybenzenesulfonyl]-3-cyclohexyl-5-ethoxy-1,3-dihydro-2H-benzimidazol-2-one This compound is prepared by the procedure described in EXAMPLE 100 starting from 0.5 g of the compound obtained in EXAMPLE 13, 0.3 g of 1-aminoada- mantane hydrochloride, 0.5 g of BOP, 2 ml of DIPEA and 25 ml of DCM. It is chromatographed on silica using a DCM/MeOH mixture (99/1; v/v) as the eluent to give 0.27 g of the expected product after crystallization from an EtOH/iso ether mixture (80/20; v/v). M.p.=228° C.

EXAMPLE 106

3-Cyclohexyl-5-cyclopentoxy-1,3-dihydro-1-[2-methoxy-4-[N-(1,1-dimethylpropyl)carbamoyl]benzenesulfonyl]-2H-benzimidazol-2-one A) Methyl 4-[3-cyclohexyl-5-cyclopentoxy-2,3-dihydro-2-oxo-1H-benzimidazol-1-yl]sulfonyl-3-methoxybenzoate 0.095 g of sodium hydride as a 60% dispersion in oil is added in portions to a mixture of 0.7 g of 3- cyclohexyl-5-cyclopentoxy-1,3-dihydro-2H-benzimidazol-2-one, 50 ml of DMF and 50 ml of THF and the mixture is stirred for 30 minutes at RT. 0.6 g of 4-methoxycarbonyl-2-methoxybenzenesulfonyl chloride is then added and the mixture is stirred for 18 hours at RT. The reaction mixture is poured into a mixture of water and ice and the precipitate formed is filtered off and washed with water and then with heptane to give 1 g of the expected product, which is used as such in the next step.

B) 4-[3-Cyclohexyl-5-cyclopentoxy-2,3-dihydro-2-oxo-1H-benzimidazol-1-yl]sulfonyl-3-methoxybenzoic acid A solution of 0.2 g of NaOH pellets in 20 ml of water is added to a solution of 1 g of the compound obtained in the previous step in 40 ml of THF and the mixture is refluxed for 2 hours. It is concentrated under vacuum, the residue is dissolved in water and washed with AcOEt, the aqueous phase is acidified to pH 1 by the addition of concentrated HCl, extracted with AcOEt and dried over $Na_2SO_4$ and the solvent is evaporated off under vacuum to give 0.56 g of the expected product. M.p.=245° C.

C) 3-Cyclohexyl-5-cyclopentoxy-1,3-dihydro-1-[2-methoxy-4-[N-(1,1-dimethylpropyl)carbamoyl]benzenesulfonyl]-2H-benzimidazol-2-one This compound is prepared by the procedure described in EXAMPLE 100 starting from 0.55 g of the compound obtained in the previous step, 1 ml of 1,1- dimethylpropylamine, 0.6 g of BOP, 1.5 ml of DIPEA and 20 ml of DCM. It is chromatographed on silica using a DCM/AcOEt mixture (90/10; v/v) as the eluent to give 0.32 g of the expected product after crystallization from iso ether. M.p.=199° C.

EXAMPLE 107

3-Cyclohexyl-1,3-dihydro-5-(2-methoxyethoxy)-1-[2-methoxy-4-[N-(1,1-dimethylpropyl)carbamoyl]benzenesulfonyl]-2H-benzimidazol-2-one A) Methyl 4-[3-cyclohexyl-2,3-dihydro-5-(2-methoxyethoxy)-2-oxo-1H-benzimidazol-1-yl]sulfonyl-3-methoxybenzoate 0.095 g of sodium hydride as a 60% dispersion in oil is added in portions to a mixture of 0.7 g of 3-cyclohexyl-1,3-dihydro-5-(2-methoxyethoxy)-2H-benzimidazol-2-one and 50 ml of DMF and the mixture is stirred for 30 minutes at RT. 0.6 g of 4-methoxycarbonyl-2-methoxybenzenesulfonyl chloride is then added and the mixture is stirred for two hours at RT. The reaction mixture is poured into a mixture of water and ice, extracted with AcOEt, washed with water and dried over $Na_2SO_4$ and the solvent is evaporated off under vacuum to give 0.8 g of the expected product, which is used as such in the next step.

B) 4-[3-Cyclohexyl-2,3-dihydro-5-(2-methoxyethoxy)-2-oxo-1H-benzimidazol-1-yl]sulfonyl-3-methoxybenzoic acid This compound is prepared by the procedure described in EXAMPLE 106 step B) starting from 0.8 g of the compound obtained in the previous step. 0.6 g of the expected product is obtained. M.p.=105° C.

C) 3-Cyclohexyl-1,3-dihydro-5-(2-methoxyethoxy)-1-[2-methoxy-4-[N-(1,1-dimethylpropyl)carbamoyl]benzenesulfonyl]-2H-benzimidazol-2-one This compound is prepared by the procedure described in EXAMPLE 99 starting from 0.55 g of the compound obtained in the previous step, 1 ml of 1,1- dimethylpropylamine, 0.6 g of BOP, 1.5 ml of DIPEA and 20 ml of DCM. It is chromatographed on silica using a DCM/AcOEt mixture (95/5; v/v) as the eluent to give 0.4 g of the expected product after crystallization from hot iso ether. M.p.=163° C.

EXAMPLE 108

1-[4-(N-tert-Butylcarbamoyl)-2-methoxybenzenesulfonyl]-5-ethoxy-1,3-dihydro-3-(2-methoxy-1,1-dimethylethyl)-2H-benzimidazol-2-one A) Methyl 4-[5-ethoxy-2,3-dihydro-3-(2-methoxy-1,1-dimethylethyl)-2-oxo-1H-benzimidazol-1-yl]sulfonyl-3-methoxybenzoate 0.12 g of sodium hydride as a 60% dispersion in oil is added in portions to a mixture of 1 g of 5- ethoxy-1,3-dihydro-3-(2-methoxy-1,1-dimethylethyl)-2H-benzimidazol-2-one and 30 ml of THF and the mixture is stirred for 30 minutes at RT. 1.2 g of 4-methoxycarbonyl-2-methoxybenzenesulfonyl chloride are then added and the mixture is stirred for 2 hours at RT. It is concentrated under vacuum, the residue is extracted with AcOEt, washed with water and dried over $Na_2SO_4$ and the solvent is evaporated off under vacuum. The residue is chromatographed on silica using a DCM/AcOEt mixture (98/2; v/v) as the eluent to give 1.7 g of the expected product, which is used as such in the next step.

B) 4-[5-Ethoxy-2,3-dihydro-3-(2-methoxy-1,1-dimethylethyl)-2-oxo-1H-benzimidazol-1-yl]sulfonyl-3-methoxybenzoic acid A solution of 0.1 g of NaOH pellets in 30 ml of water is added to a solution of 1.7 g of the compound obtained in the previous step in 50 ml of THF and the mixture is stirred for 5 hours at RT. It is concentrated under vacuum, the residue is dissolved in 100 ml of water and washed with AcOEt, the aqueous phase is acidified to pH 1 by the addition of concentrated HCl and the precipitate formed is filtered off and washed with EtOH and then with iso ether to give 1.6 g of the expected product. M.p.=250° C.

C) 1-[4-(N-tert-Butylcarbamoyl)-2-methoxybenzenesulfonyl]-5-ethoxy-1,3-dihydro-3-(2-methoxy-1,1-dimethylethyl)-2H-benzimidazol-2-one This compound is prepared by the procedure described in EXAMPLE 99 starting from 0.8 g of the compound obtained in the previous step, 2 ml of tert- butylamine, 0.9 g of BOP, 2 ml of DIPEA and 30 ml of DCM. It is chromatographed on silica using a DCM/AcOEt mixture (96/4; v/v) as the eluent to give 0.48 g of the expected product in the form of white crystals. M.p.=181° C.

EXAMPLE 109

5-Ethoxy-1,3-dihydro-3-(tetrahydropyran-4-yl)-1-[2-methoxy-4-[N-(1,1-dimethylpropyl)carbamoyl]benzenesulfonyl]-2H-benzimidazol-2-one A) Methyl 4-[5-ethoxy-2,3-dihydro-3-(tetrahydropyran-4-yl)-2-oxo-1H-benzimidazol-1-yl]sulfonyl-3-methoxybenzoate 0.18 g of sodium hydride as a 60% dispersion in oil is added in portions to a mixture of 1 g of 5- ethoxy-1,3-dihydro-3-(tetrahydropyran-4-yl)-2H-benzimidazol-2-one, 30 ml of THF and 20 ml of DMF and the mixture is stirred for 30 minutes at RT. 1.2 g of 4- methoxycarbonyl-2-methoxybenzenesulfonyl chloride are then added and the mixture is stirred for 3 hours at RT. The reaction mixture is poured into 200 ml of water and the precipitate formed is filtered off and washed with iso ether to give 1.13 g of the expected product after drying. M.p.=165° C.

B) 4-[5-Ethoxy-2,3-dihydro-3-(tetrahydropyran-4-yl)-2-oxo-1H-benzimidazol-1-yl]sulfonyl-3-methoxybenzoic acid A solution of 0.5 g of NaOH pellets in 30 ml of water is added to a solution of 1.13 g of the compound obtained in the previous step in 20 ml of THF and the mixture is stirred for 16 hours at RT. The reaction mixture is washed with AcOEt, the aqueous phase is acidified to pH 1 by the addition of concentrated HCl, extracted with AcOEt and dried over $Na_2SO_4$ and the solvent is evaporated off under vacuum to give 0.8 g of the expected product after crystallization from iso ether. M.p.=255° C.

C) 5-Ethoxy-1,3-dihydro-3-(tetrahydropyran-4-yl)-1-[2-methoxy-4-[N-(1,1-dimethylpropyl)carbamoyl]benzenesulfonyl]-2H-benzimidazol-2-one This compound is prepared by the procedure described in EXAMPLE 99 starting from 0.39 g of the compound obtained in the previous step, 1 ml of 1,1- dimethylpropylamine, 0.45 g of BOP, 1 ml of DIPEA and 30 ml of DCM. It is chromatographed on silica using a DCM/MeOH mixture (99/1; v/v) as the eluent to give 0.28 g of the expected product in the form of white crystals. M.p.=183° C.

EXAMPLE 110

3-Cycloheptyl-5-ethoxy-1,3-dihydro-1-[2-methoxy-4-[N-(1,1-dimethylpropyl)carbamoyl]benzenesulfonyl]-2H-benzimidazol-2-one A) Methyl 4-[3-cycloheptyl-5-ethoxy-2,3-dihydro-2-oxo-1H- benzimidazol-1-yl]sulfonyl-3-methoxybenzoate 0.095 g of sodium hydride as a 60% dispersion in oil is added to a mixture of 0.7 g of 3-cycloheptyl-5-ethoxy-1,3-dihydro-2H-benzimidazol-2-one and 50 ml of DMF and the mixture is stirred for 30 minutes at RT. 0.7 g of 4-methoxycarbonyl-2-methoxybenzenesulfonyl chloride is then added and the mixture is stirred overnight at RT. The reaction mixture is poured into iced water and the precipitate formed is filtered off and washed with water to give 0.9 g of the expected product, which is used as such in the next step.

B) 4-[3-Cycloheptyl-5-ethoxy-2,3-dihydro-2-oxo-1H-benzimidazol-1-yl]sulfonyl-3-methoxybenzoic acid A solution of 0.3 g of NaOH pellets in 20 ml of water is added to a solution of 0.9 g of the compound obtained in the previous step in 40 ml of THF and the mixture is refluxed for 2 hours. After cooling, it is acidified to pH 1 by the addition of concentrated HCl and the precipitate formed is filtered off and washed with water. The precipitate is dissolved in AcOEt and dried over $Na_2SO_4$ and the solvent is evaporated off under vacuum to give 0.75 g of the expected product, which is used as such in the next step.

C) 3-Cycloheptyl-5-ethoxy-1,3-dihydro-1-[2-methoxy-4-[N-(1,1-dimethylpropyl)carbamoyl]benzenesulfonyl]-2H-benzimidazol-2-one This compound is prepared by the procedure described in EXAMPLE 99 starting from 0.75 g of the compound obtained in the previous step, 1.5 ml of 1,1- dimethylpropylamine, 0.85 g of BOP, 2 ml of DIPEA and 25 ml of DCM. It is chromatographed on silica using a DCM/AcOEt mixture (95/5; v/v) as the eluent to give 0.26 g of the expected product after crystallization from iso ether. M.p.=192° C.

EXAMPLE 111

5-Ethoxy-1,3-dihydro-1-[2-methoxy-4-(N,N-dimethylcarbamoyl)benzenesulfonyl]-3-(pyrid-2-yl)-2H-benzimidazol-2-one A) Methyl 4-[5-ethoxy-2,3-dihydro-2-oxo-3-(pyrid-2-yl)-1H-benzimidazol-1-yl]sulfonyl-3-methoxybenzoate 0.2 g of sodium hydride as a 60% dispersion in oil is added to a mixture of 1 g of 5-ethoxy-1,3-dihydro-3-(pyrid-2-yl)-2H-benzimidazol-2-one, 25 ml of DMF and 25 ml of THF and the mixture is stirred for 30 minutes at RT. 1 g of 4-methoxycarbonyl-2-methoxybenzenesulfonyl chloride is then added and the mixture is stirred for 3 hours at RT. The reaction mixture is concentrated under vacuum, the residue is taken up with water, extracted with AcOEt, washed with water and dried over $Na_2SO_4$ and the solvent is evaporated off under vacuum to give 1 g of the expected product, which is used as such in the next step.

B) 4-[5-Ethoxy-2,3-dihydro-2-oxo-3-(pyrid-2-yl)-1H-benzimidazol-1-yl]sulfonyl-3-methoxybenzoic acid A solution of 0.3 g of NaOH pellets in 20 ml of water is added to a solution of 1 g of the compound obtained in the previous step in 20 ml of THF and the mixture is stirred for 3 hours at RT. The reaction mixture is extracted with AcOEt, the aqueous phase is acidified to pH 1 by the addition of concentrated HCl, extracted with AcOEt and dried over $Na_2SO_4$ and the solvent is evaporated off under vacuum to give 0.72 g of the expected product after crystallization from iso ether. M.p.=241° C.

C) 5-Ethoxy-1,3-dihydro-1-[2-methoxy-4-(N, N-dimethylcarbamoyl)benzenesulfonyl]-3-(pyrid-2-yl)-2H-benzimidazol-2-one A mixture of 0.72 g of the compound obtained in the previous step, 0.17 g of dimethylamine hydrochloride, 2 ml of DIPEA, 0.9 g of BOP and 20 ml of DCM is stirred for 3 hours at RT. The reaction mixture is concentrated under vacuum, the residue is extracted with AcOEt, washed with water, with a 1N solution of HCl and with a 1N solution of NaOH and dried over $Na_2SO_4$ and the solvent is evaporated off under vacuum. The residue is chromatographed on silica using a DCM/AcOEt mixture (85/15; v/v) as the eluent to give 0.2 g of the expected product. M.p.=201° C.

EXAMPLE 112

5-Ethoxy-1,3-dihydro-1-[2-methoxy-4-[N-(1,1-dimethylpropyl)carbamoyl]benzenesulfonyl]-3-(pyrid-2-yl)-2H-benzimidazol-2-one A mixture of 0.3 g of the compound obtained in EXAMPLE 111 step B), 0.5 ml of 1,1-dimethylpropylamine, 0.5 ml of DIPEA, 0.35 g of BOP and 20 ml of DCM is stirred for 3 hours at RT. The reaction mixture is concentrated under vacuum, the residue is extracted with AcOEt, washed with a 1N solution of HCl and with a 1N solution of NaOH and dried over $Na_2SO_4$ and the solvent is evaporated off under vacuum. The residue is chromatographed on silica using a DCM/AcOEt mixture (90/10; v/v) as the eluent to give 0.15 g of the expected product after crystallization from iso ether.

NMR spectrum at 200 MHz in DMSO.

0.7 ppm : t : 3H
1.25 ppm : m : 9H
1.7 ppm : q : 2H
3.55 ppm : s : 3H
3.95 ppm : q : 2H
6.7 to 8.7 ppm : m : 11H

EXAMPLE 113

3-Cyclopentyl-5-ethoxy-1,3-dihydro-1-[2-methoxy-4-[N-(1,1-dimethylpropyl)carbamoyl]benzenesulfonyl]-2H-benzimidazol-2-one A) Methyl 4-[3-cyclopentyl-5-ethoxy-2,3-dihydro-2-oxo-1H-benzimidazol-1-yl]sulfonyl-3-methoxybenzoate This compound is prepared by the procedure described in EXAMPLE 107 step A) starting from 1 g of 3- cyclopentyl-5-ethoxy-1,3-dihydro-2H-benzimidazol-2-one and 1.2 g of 4-methoxycarbonyl-2-methoxybenzenesulfonyl chloride. It is chromatographed on silica using a DCM/AcOEt mixture (95/5; v/v) as the eluent to give 1.4 g of the expected product. M.p.=151° C.

B) 4-[3-Cyclopentyl-5-ethoxy-2,3-dihydro-2-oxo-1H-benzimidazol-1-yl]sulfonyl-3-methoxybenzoic acid This compound is prepared by the procedure described in EXAMPLE 106 step B) starting from 1.4 g of the compound obtained in the previous step. This gives 0.9 g of the expected product, which is used as such in the next step.

C) 3-Cyclopentyl-5-ethoxy-1,3-dihydro-1-[2-methoxy-4-[N-(1,1-dimethylpropyl)carbamoyl]benzenesulfonyl]-2H-benzimidazol-2-one A mixture of 0.9 g of the compound obtained in the previous step, 2 ml of 1,1-dimethylpropylamine, 1 g of BOP, 3 ml of DIPEA and 30 ml of DCM is stirred for 3 hours at RT. The reaction mixture is concentrated under vacuum and the residue is chromatographed on silica using a DCM/AcOEt mixture (90/10; v/v) as the eluent to give 0.32 g of the expected product after crystallization from iso ether. M.p.=210° C.

EXAMPLE 114

5-Chloro-3-(3-chlorophenyl)-1,3-dihydro-1-(2,4-dimethoxybenzenesulfonyl)-2H-benzimidazol-2-one A solution of 2 g of 5-chloro-3-(3-chlorophenyl)-1,3-dihydro-2H-benzimidazol-2-one in 170 ml of THF is cooled to −40° C. and 0.97 g of potassium tert- butylate is added. The mixture is stirred for 30 minutes at −10° C. and then cooled to −50° C. and a solution of 1.7 g of 2,4-dimethoxybenzenesulfonyl chloride in 70 ml of THF is added. The reaction mixture is stirred for 2 hours, the temperature being allowed to rise to RT, and then concentrated under vacuum. The residue is taken up with water, extracted with DCM and dried over $Na_2SO_4$ and the solvent is evaporated off under vacuum to give 2.3 g of the expected product after crystallization from a cyclohexane/DCM mixture (90/10; v/v). M.p.=173° C.

EXAMPLE 115

3-Cyclohexyl-5-ethoxy-1,3-dihydro-1-[2-methoxy-4-[N-(2-dimethylamino-1,1-dimethylethyl)carbamoyl]benzenesulfonyl]-2H-benzimidazol-2-one A mixture of 1 g of the compound obtained in EXAMPLE 13, 1 g of 2-dimethylamino -1,1- dimethylethylamine (synthesized according to J. Am. Chem. Soc., 1946, 68, 10–12), 1 g of BOP, 1 ml of DIPEA and 20 ml of DCM is stirred for 16 hours at RT. The reaction mixture is evaporated under vacuum, the residue is extracted with AcOEt, washed with a 1N solution of NaOH, extracted with a 6N solution of HCl, washed with AcOEt, the acidic aqueous phase is rendered alkaline by the addition of 2N NaOH, extracted with AcOEt and dried over $Na_2SO_4$ and the solvent is evaporated off under vacuum. The residue is chromatographed on silica using a DCM/MeOH mixture (99/1; v/v) as the eluent to give 0.65 g of the expected product after crystallization from iso ether. M.p.=161° C.

EXAMPLE 116

3-Cyclohexyl-5-ethoxy-1,3-dihydro-1-[2-methoxy-4-[N-(2-dimethylamino-1,1-dimethylethyl)carbamoyl]benzenesulfonyl]-2H-benzimidazol-2-one fumarate A mixture of 0.48 g of the compound obtained in EXAMPLE 115, 0.05 g of fumaric acid and 15 ml of acetone is refluxed for 5 minutes. The reaction mixture is concentrated under vacuum to give 0.13 g of the expected product after crystallization from ether. M.p.=135° C.

What is claimed is:

1. A compound of the formula

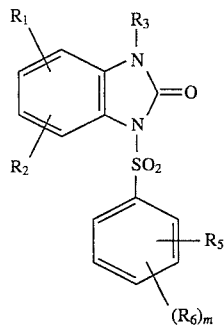

(I)

in which $R_1$ and $R_2$ are each independently a hydrogen; a halogen; a hydroxyl; an ω-halogeno($C_1$–$C_7$)alkoxy; a ($C_1$–$C_7$)alkyl; a trifluoromethyl; a ($C_1$–$C_7$) alkoxy; a polyhalogeno($C_1$–$C_7$)alkoxy; an ω-hydroxy($C_2$–$C_7$)alkoxy; an ω-methoxy($C_2$–$C_7$)alkoxy; an ω-amino($C_2$–$C_7$)alkoxy in which the amino is free or substituted by one or two ($C_1$–$C_7$)alkyls; a ($C_3$–$C_7$)cycloalkoxy; a ($C_3$–$C_7$)cycloalkylmethoxy; a phenoxy; a benzyloxy; a ($C_1$–$C_7$)alkylthio; a phenylthio; a nitro; an amino which is free or substituted by one or two ($C_1$–$C_7$)alkyls; a cyano; a formyl; a ($C_1$–$C_7$)alkylcarbonyl; a benzoyl; a formyloxy; a ($C_1$–$C_7$)alkylcarbonyloxy; a benzoyloxy; a ($C_1$–$C_7$)alkylsulfonamido; a phenylsulfonamido; a benzylsulfonamido; a ($C_1$–$C_7$)alkylcarbonylamino; a ($C_1$–$C_7$)alkoxycarbonylamino; a ureido which is unsubstituted or substituted by a phenyl, a benzyl or one or two ($C_1$–$C_7$)alkyls; or a thioureido which is unsubstituted or substituted by a phenyl, a benzyl or one or two ($C_1$–$C_7$)alkyls;

$R_3$ is $R_4$; a ($C_1$–$C_8$)alkylene substituted by $R_4$; a ($C_1$–$C_8$)alkylene substituted by a ($C_1$–$C_4$)alkoxy; an indanyl; a hexahydroindanyl; an adamantyl; a noradamantyl; a norbornyl; or a cyclohexyl substituted by a di($C_1$–$C_7$)alkylamino, a carboxyl, a ($C_1$–$C_4$)alkoxycarbonyl, a hydroxyl, a tetrahydropyran-2-yloxy, a ($C_1$–$C_4$)alkoxy($C_1$–$C_4$)alkoxy or a phenyl ($C_1$–$C_2$)alkoxy ($C_1$–$C_4$)alkoxy;

$R_4$ is a group —$NR_{16}R_{17}$; a ($C_3$–$C_7$)cycloalkyl which is unsubstituted or monosubstituted or disubstituted by a ($C_1$–$C_4$)alkyl or a ($C_1$–$C_4$)alkoxy; a group Ar; a furyl; a thienyl; a pyrrolyl; a triazolyl; a tetrazolyl; a pyridyl; a pyridyl N-oxide; a pyrimidinyl; a pyrazolyl; a pyrazinyl; a tetrahydropyran-4-yl; an azetidin-3-yl substituted in the 1-position by $R_{18}$; a piperid-4-yl substituted in the 1-position by $R_{18}$ or disubstituted in the 1-position by one or two ($C_1$–$C_7$)alkyls and/or one or two benzyls; a pyrrolidinyl; a perhydroazepinyl; or a morpholinyl;

$R_5$ and $R_6$ are each independently a hydrogen; a halogen; a ($C_1$–$C_7$)alkyl; a trifluoromethyl; a cyano; a nitro; a hydroxylamino; a carboxyl; a guanidino which is unsubstituted or substituted in the 1-position by a ($C_1$–$C_7$)alkyl and/or in the 3-position by one or two ($C_1$–$C_7$)alkyls, a phenyl or a benzyl and/or in the 2-position by a cyano; a group —$OR_7$; a group —$SR_7$; a ($C_1$–$C_7$)alkylcarbonyl; a formyl; a benzoyl; a ($C_1$–$C_7$)alkoxycarbonyl; a phenoxycarbonyl; a benzyloxycarbonyl; a group —$CONR_{19}R_{20}$; a group —$CSNR_{11}R_{27}$; a group —$SO_2NR_{21}R_{22}$; a ($C_1$–$C_7$)alkylsulfonamido; a benzylsulfonamido; a group —$NHSO_2$—Ar; a group —$NR_8R_9$; a group —CO—NH—$CR_{10}R_{23}$—$COR_{12}$; or a group —$CH_2NR_8R_9$;

$R_7$ is a hydrogen; a ($C_1$–$C_7$)alkyl; a phenyl; a benzyl; a ($C_3$–$C_7$)cycloalkyl; a ($C_2$–$C_7$)alkenyl; an ω-halogeno($C_2$–$C_7$)alkyl; a polyhalogeno($C_1$–$C_7$)alkyl; an ω-hydroxy($C_2$–$C_7$)alkyl; a ($C_1$–$C_7$)alkylcarbonyl; a formyl; a benzoyl; an ω-carboxy($C_1$–$C_7$)alkyl; an ω-($C_1$–$C_7$)alkoxycarbonyl($C_1$–$C_7$)alkyl; an ω-benzyloxycarbonyl($C_1$–$C_7$)alkyl; an ω-amino($C_2$–$C_7$)alkyl in which the amino group is free or substituted by one or two ($C_1$–$C_7$)alkyls, or in the form of an ammonium ion; or an ω-carbamoyl($C_1$–$C_7$)alkyl in which the carbamoyl is free or substituted by one or two ($C_1$–$C_7$)alkyls;

$R_8$ is hydrogen; a ($C_1$–$C_7$)alkyl; or a group —$CH_2$—Ar;

$R_9$ is hydrogen; a($C_1$–$C_7$)alkyl; a group—$CH_2$—Ar; a group Ar; a ($C_3$–$C_8$)alkenyl; a ($C_1$–$C_7$)alkylcarbonyl; a formyl; a ($C_1$–$C_7$)alkylthiocarbonyl; a ($C_3$–$C_7$)cycloalkylcarbonyl; a ($C_3$–$C_7$)cycloalkylthiocarbonyl; an ω-amino($C_2$–$C_7$)alkylcarbonyl in which the amino is free or substituted by one or two ($C_1$–$C_7$)alkyls; an ω-hydroxy($C_1$–$C_7$)alkylcarbonyl; an ω-benzyloxy($C_1$–$C_7$)alkylcarbonyl; a pyridylcarbonyl; a methylpyridylcarbonyl; a thienylcarbonyl; a group —CO—Ar; a group —CO—$CH_2$—Ar; a ($C_1$–$C_7$)alkoxycarbonyl; a phenoxycarbonyl; a phenoxythiocarbonyl; a benzyloxycarbonyl; a group —CO—$CR_{10}R_{23}$—$NR_{11}R_{27}$; a group —$CR_{10}R_{23}COR_{12}$; a group —$(CH_2)_tCOR_{12}$; a group —$CO(CH_2)_uCOR_{12}$; a group —$CONR_{14}R_{24}$; a group —$CSNR_{14}R_{24}$; or a heterocyclic radical selected from pyrazolyl, imidazolyl, triazolyl, tetrazolyl, pyridyl, pyridazinyl, pyrimidinyl and thiazolyl;

or else $R_8$ and $R_9$, together with the nitrogen atom to which they are bonded, form hydantoin, N-methylhydantoin or a heterocyclic radical selected from morpholin-4-yl, pyrrol-1-yl, Δ3-pyrrolin-1-yl, pyrrolidin-1-yl and isoindolin-2-yl, in which the benzene ring is unsubstituted or substituted by a halogen, a ($C_1$–$C_7$)alkyl, a trifluoromethyl or a methoxy;

$R_{10}$ and $R_{23}$ are each independently hydrogen; a ($C_1$–$C_7$)alkyl; or a benzyl;

or else $R_{10}$ and $R_{23}$, together with the carbon atom to which they are bonded, form a ($C_3$–$C_7$)cycloalkyl;

$R_{11}$ and $R_{27}$ are each independently hydrogen; or a $(C_1-C_7)$alkyl;

$R_{12}$ is a hydroxyl; a $(C_1-C_7)$alkoxy; or an amino which is free or substituted by one or two $(C_1-C_7)$alkyls;

$R_{14}$ is hydrogen; or a $(C_1-C_7)$alkyl;

$R_{24}$ is hydrogen; a $(C_1-C_7)$alkyl; a $(C_1-C_7)$alkyl substituted by $R_{15}$; a group Ar; a $(C_3-C_7)$cycloalkyl; or an adamantyl;

or $R_{14}$ and $R_{24}$, together with the nitrogen atom to which they are bonded, form a heterocycle selected from morpholine, thiomorpholine, piperazine, azetidine, pyrrolidine, piperidine and perhydroazepine, said heterocycle being unsubstituted or substituted by one or more methyl groups, a phenyl or an amino group which is free or carries a protecting group;

$R_{15}$ is a group Ar; a pyridyl; a hydroxyl; a $(C_1-C_7)$alkoxy; a group $-NR_{11}R_{27}$; a carboxyl; or a $(C_1-C_7)$alkoxycarbonyl;

$R_{16}$ and $R_{17}$ are each independently hydrogen; or a $(C_1-C_7)$alkyl;

or else $R_{16}$, and $R_{17}$, together with the nitrogen atom to which they are bonded, form a heterocycle selected from morpholine, thiomorpholine, azetidine, pyrrolidine, piperidine and piperazine, substituted in the 4-position by $R_{18}$, and perhydroazepine;

$R_{18}$ is a hydrogen; a $(C_1-C_7)$alkyl; a phenyl; a benzyl; a $(C_1-C_7)$alkylcarbonyl; a formyl; a benzoyl; a $(C_1-C_7)$alkoxycarbonyl; a phenoxycarbonyl; or a carbamoyl which is free or substituted by one or two $(C_1-C_7)$alkyls;

$R_{19}$ is hydrogen; or a $(C_1-C_8)$alkyl;

$R_{20}$ is a hydrogen; a $(C_1-C_8)$alkyl; a $(C_3-C_7)$cycloalkyl which is unsubstituted or substituted by a $(C_1-C_4)$alkyl; a group Ar; a pyridyl; a methylpyridyl; a piperid-4-yl substituted in the 1-position by $R_{18}$; a piperid-1-yl; a pyrrolidin-1-yl; a morpholin-4-yl; a thiazol-2-yl; an indanyl; an adamantyl; or a $(C_1-C_7)$alkyl substituted by one or more halogens or $R_{26}$;

or else $R_{19}$ and $R_{20}$, together with the nitrogen atom to which they are bonded, form a heterocyclic radical $R_{25}$;

$R_{21}$ and $R_{22}$ are each independently hydrogen; or a $(C_1-C_7)$alkyl;

or else $R_{21}$ and $R_{22}$, together with the nitrogen atom to which they are bonded, form a heterocyclic radical $R_{25}$;

$R_{25}$ is a morpholin-4-yl; a thiomorpholin-4-yl; an azetidin-1-yl which is unsubstituted or substituted in the 3-position by a group $-NR_{11}R_{27}$, a $(C_1-C_7)$alkyl, a phenyl, a benzyl or a $(C_1-C_7)$alkylcarbonyl; a perhydroazepin-1-yl; a piperazin-1-yl which is unsubstituted or substituted in the 4-position by a $(C_1-C_7)$alkyl, a phenyl, a benzyl, a $(C_1-C_7)$alkylcarbonyl, a $(C_1-C_7)$alkoxycarbonyl or a benzyloxycarbonyl; a piperid-1-yl which is unsubstituted or substituted in the 4-position by a $(C_1-C_7)$alkyl, a phenyl, a benzyl, a $(C_1-C_7)$alkylcarbonyl or a group $-NR_{11}R_{27}$; or a pyrrolidin-1-yl which is unsubstituted or substituted by a $(C_1-C_7)$alkyl, a phenyl, a benzyl, a $(C_1-C_7)$alkylcarbonyl, a hydroxymethyl, a carboxyl, a $(C_1-C_7)$alkoxycarbonyl or a carbamoyl which is unsubstituted or substituted by one or two $(C_1-C_7)$alkyls;

$R_{26}$ is a hydroxyl; a $(C_1-C_7)$alkoxy; a cyano; a carboxyl; a $(C_1-C_7)$alkoxycarbonyl; a benzyloxycarbonyl; a group $-NR_{11}R_{27}$; a carbamoyl which is free or substituted by one or two $(C_1-C_7)$alkyls; a pyrrolidin-1-ylcarbonyl; a piperid-1-ylcarbonyl; a perhydroazepin-1-ylcarbonyl; a group Ar; a $(C_3-C_7)$cycloalkyl; an adamantyl; or a heterocyclic radical selected from a pyridyl, a methylpyridyl, a furanyl, a tetrahydrofuranyl, a thienyl, a methylthienyl, a pyrrolidin-1-yl, a piperid-1-yl and a perhydroazepin-1-yl;

Ar is a phenyl which is unsubstituted or monosubstituted or polysubstituted by a substituent selected from a halogen atom, a $(C_1-C_7)$alkyl, a trifluoromethyl, a hydroxyl, a $(C_1-C_7)$alkoxy, a carboxyl, a $(C_1-C_7)$alkoxycarbonyl, a $(C_1-C_7)$alkylcarbonyloxy, a nitro, a cyano, an amino, a $(C_1-C_7)$alkylamino and a di$(C_1-C_7)$alkylamino, said substituents being identical or different;

t is an integer which may vary from 2 to 5;

u is an integer which may vary from 0 to 5; and m is 1-4, provided that when m is 2-4 each $R_6$ independently represents a halogen, a $(C_1-C_7)$alkyl or a $(C_1-C_7)$alkoxy; and its salts.

2. A compound according to claim 1 of the formula

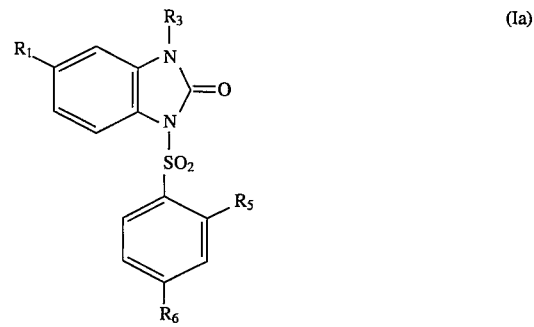

(Ia)

in which:

$R_1$ is a $(C_1-C_4)$alkoxy or a chlorine or fluorine atom;

$R_5$ is a hydrogen or a methoxy;

$R_6$ is a $(C_1-C_7)$alkylcarboxamido, a group $-NHCOAr$, a group $-CONR_{19}R_{20}$, a group $-NR_8CONR_{14}R_{24}$, a $(C_1-C_7)$alkoxy or an amino which is free or substituted by one or two $(C_1-C_7)$alkyls; and the substituents $R_3$, Ar, $R_8$, $R_9$, $R_{20}$, $R_{14}$ and $R_{24}$ are as defined for the compound of formula (I) in claim 1; and its salts.

3. A compound according to claim 1, of the formula

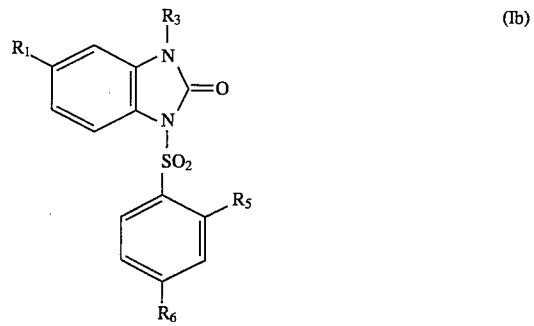

(Ib)

in which $R_1$ is an ethoxy or a chlorine;

$R_3$ is a cyclohexyl or a group Ar;

$R_5$ is a hydrogen or a methoxy;

$R_6$ is a group $-CONR_{19}R_{20}$ or a group $-NR_8CONR_{14}R_{24}$; and the substituents Ar, $R_{19}$, $R_{20}$, $R_8$, $R_-$ and $R_{24}$ are as defined for the compound of formula (I) in claim 1; and its salts.

4. A compound according to claim 3, wherein $R_1$ is ethoxy, $R_3$ is a group Ar, $R_5$ is methoxy and $R_6$ is a group —$CONR_{19}R_{20}$ or a group —$NR_8CONR_{14}R_{24}$; and its salts.

5. A pharmaceutical composition containing an effective amount of a compound according to claim 1 or a pharmaceutically acceptable salt thereof, in combination with suitable excipients.

6. A pharmaceutical composition containing (i) an effective amount of a compound according to claim 1 or a pharmaceutically acceptable salt thereof; (ii) an effective amount of a compound selected from the group consisting of a converting enzyme inhibitor, an angiotensin II antagonist, a renin inhibitor, a peripheral vasodilator, a calcium inhibitor, a beta-blocking agent, an alpha-1-blocking agent and a diuretic; and (iii) suitable excipients.

7. A pharmaceutical composition containing effective amounts of two compounds of formula (I) or of pharmaceutically acceptable salts thereof, one being a specific $V_1$ receptor antagonist and the other being a specific $V_2$ receptor antagonist, in combination with suitable excipients:

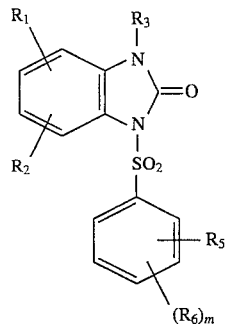

(I)

in which:

$R_1$ and $R_2$ are each independently a hydrogen; a halogen; a hydroxyl; an ω-halogeno($C_1$–$C_7$)alkoxy; a ($C_1$–$C_7$)alkyl; a trifluoromethyl; a ($C_1$–$C_7$)alkoxy; a polyhalogeno($C_1$–$C_7$)alkoxy; an ω-hydroxy($C_2$–$C_7$)alkoxy; an ω-methoxy($C_2$–$C_7$)alkoxy; an ω-amino($C_2$–$C_7$)alkoxy in which the amino is free or substituted by one or two ($C_1$–$C_7$)alkyls; a ($C_3$–$C_7$)cycloalkoxy; a ($C_3$–$C_7$)cycloalkylmethoxy; a phenoxy; a benzyloxy; a ($C_1$–$C_7$)alkylthio; a phenylthio; a nitro; an amino which is free or substituted by one or two ($C_1$–$C_7$)alkyls; a cyano; a formyl; a ($C_1$–$C_7$)alkylcarbonyl; a benzoyl; a formyloxy; a ($C_1$–$C_7$)alkylcarbonyloxy; a benzoyloxy; a ($C_1$–$C_7$)alkylsulfonamido; a phenylsulfonamido; a benzylsulfonamido; a ($C_1$–$C_7$)alkylcarbonylamino; a ($C_1$–$C_7$)alkoxycarbonylamino; a ureido which is unsubstituted or substituted by a phenyl, a benzyl or one or two ($C_1$–$C_7$)alkyls; or a thioureido which is unsubstituted or substituted by a phenyl, a benzyl or one or two ($C_1$–$C_7$)alkyls;

$R_3$ is $R_4$; a ($C_1$–$C_8$)alkyl; a ($C_1$–$C_8$)alkylene substituted by $R_4$; a ($C_1$–$C_8$)alkylene substituted by a ($C_1$–$C_4$)alkoxy; an indanyl; a hexahydroindanyl; an adamantyl; a noradamantyl; a norbornyl; or a cyclohexyl substituted by a di($C_1$–$C_7$)alkylamino, a carboxyl, a ($C_1$–$C_4$)alkoxycarbonyl, a hydroxyl, a tetrahydropyran-2-yloxy, a ($C_1$–$C_4$)alkoxy($C_1$–$C_4$)alkoxy or a phenyl($C_1$–$C_2$)alkoxy($C_1$–$C_2$)alkoxy;

$R_4$ is a group —$NR_{16}R_{17}$; a ($C_3$–$C_7$)cycloalkyl which is unsubstituted or monosubstituted or disubstituted by a ($C_1$–$C_4$)alkyl or a ($C_1$–$C_4$)alkoxy; a group Ar; a furyl; a thienyl; a pyrrolyl; a triazolyl; a tetrazolyl; a pyridyl; a pyridyl N-oxide; a pyrimidinyl; a pyrazolyl; a pyrazinyl; a tetrahydropyran-4-yl; an azetidin-3-yl substituted in the 1-position by $R_{18}$; a piperid-4-yl substituted in the 1-position by $R_{18}$ or disubstituted in the 1-position by one or two ($C_1$–$C_7$)alkyls and/or one or two benzyls; a pyrrolidinyl; a perhydroazepinyl; or a morpholinyl;

$R_5$ and $R_6$ are each independently a hydrogen; a halogen; a ($C_1$–$C_7$)alkyl; a trifluoromethyl; a cyano; a nitro; a hydroxylamino; a carboxyl; a guanidino which is unsubstituted or substituted in the 1-position by a ($C_1$–$C_7$)alkyl and/or in the 3-position by one or two ($C_1$–$C_7$)alkyls, a phenyl or a benzyl and/or in the 2-position by a cyano; a group —$OR_7$; a group —$SR_7$; a ($C_1$–$C_7$)alkylcarbonyl; a formyl; a benzoyl; a ($C_1$–$C_7$)alkoxycarbonyl; a phenoxycarbonyl; a benzyloxycarbonyl; a group —$CONR_{19}R_{20}$; a group —$CSNR_{11}R_{27}$; a group —$SO_2$-$NR_{21}R_{22}$; a ($C_1$–$C_7$)alkylsulfonamido; a benzylsulfonamido; a group —$NHSO_2$—Ar; a group —$NR_8R_9$; a group —CO—NH—$CR_{10}R_{23}$—CO—$R_{12}$; or a group —$CH_2NR_8R_9$;

$R_7$ is a hydrogen; a ($C_1$–$C_7$)alkyl; a phenyl; a benzyl; a ($C_3$–$C_7$)cycloalkyl; a ($C_2$–$C_7$)alkenyl; an ω-halogeno($C_2$–$C_7$)alkyl; a polyhalogeno($C_1$–$C_7$)alkyl; an ω-hydroxy($C_2$–$C_7$)alkyl; a ($C_1$–$C_7$)alkylcarbonyl; a formyl; a benzoyl; an ω-carboxy($C_1$–$C_7$)alkyl; an ω-($C_1$–$C_7$)alkoxy-carbonyl($C_1$–$C_7$)alkyl; an ω-benzyloxycarbonyl ($C_1$–$C_7$)alkyl; an ω-amino($C_2$–$C_7$)alkyl in which the amino group is free or substituted by one or two ($C_1$–$C_7$)alkyls, or in the form of an ammonium ion; or an ω-carbamoyl($C_1$–$C_7$)alkyl in which the carbamoyl is free or substituted by one or two ($C_1$–$C_7$)alkyls;

$R_8$ is hydrogen; a ($C_1$–$C_7$)alkyl; or a group —$CH_2$—Ar;

$R_9$ is hydrogen; a($C_1$–$C_7$)alkyl; a group—$CH_2$—Ar; a group Ar; a ($C_3$–$C_8$)alkenyl; a ($C_1$–$C_7$)alkylcarbonyl; a formyl; ($C_1$–$C_7$)alkylthiocarbonyl; a ($C_3$–$C_7$)cycloalkylcarbonyl; a ($C_3$–$C_7$)cycloalkylthiocarbonyl; an ω-amino($C_2$–$C_7$)alkylcarbonyl in which the amino is free or substituted by one or two ($C_1$–$C_7$)alkyls; an ω-hydroxy($C_1$–$C_7$)alkylcarbonyl; an ω-benzyloxy($C_1$–$C_7$)alkylcarbonyl; a pyridylcarbonyl; a methylpyridylcarbonyl; a thienylcarbonyl; a group —CO—Ar; a group —CO—$CH_2$—Ar; a ($C_1$–$C_7$)alkoxycarbonyl; a phenoxycarbonyl; a phenoxythiocarbonyl; a benzyloxycarbonyl; a group —CO—$CR_{10}R_{23}$—$NR_{11}R_{27}$; a group —$CR_{10}R_{23}COR_{12}$; a group ($CH_2$)$_t$$COR_{12}$; a group —CO($CH_2$)$_u$$COR_{12}$; a group —$CONR_{14}R_{24}$; a group —$CSNR_{14}R_{24}$; or a heterocyclic radical selected from pyrazolyl, imidazolyl, triazolyl, tetrazolyl, pyridyl, pyridazinyl, pyrimidinyl and thiazolyl;

or else $R_8$ and $R_9$, together with the nitrogen atom to which they are bonded, form hydantoin, N-methylhydantoin or a heterocyclic radical selected from morpholin-4-yl, pyrrol-1-yl, Δ3-pyrrolin-1-yl, pyrrolidin-1-yl and isoindolin-2-yl, in which the benzene ring is unsubstituted or substituted by a halogen, a ($C_1$–$C_7$)alkyl, a trifluoromethyl or a methoxy;

$R_{10}$ and $R_{23}$ are each independently hydrogen; a ($C_1$–$C_7$)alkyl; or a benzyl;

or else $R_{10}$ and $R_{23}$, together with the carbon atom to which they are bonded, form a ($C_3$–$C_7$)cycloalkyl;

$R_{11}$ and $R_{27}$ are each independently hydrogen; or a $(C_1-C_7)$alkyl;

$R_{12}$ is a hydroxyl; a $(C_1-C_7)$alkoxy; or an amino which is free or substituted by one or two $(C_1-C_7)$alkyls;

$R_{14}$ is hydrogen; or a $(C_1-C_7)$alkyl;

$R_{24}$ is hydrogen; a $C_1-C_7$ alkyl;

a $(C_1-C_7)$alkyl substituted by $R_{15}$; a group Ar; a $(C_3-C_7)$cycloalkyl; or an adamantyl;

or $R_{14}$ and $R_{24}$, together with the nitrogen atom to which they are bonded, form a heterocycle selected from morpholine, thiomorpholine, piperazine, azetidine, pyrrolidine, piperidine and perhydroazepine, said heterocycle being unsubstituted or substituted by one or more methyl groups, a phenyl or an amino group which is free or carries a protecting group;

$R_{15}$ is a group Ar; a pyridyl; a hydroxyl; a $(C_1-C_7)$alkoxy; a group —$NR_{11}R_{27}$; a carboxyl; or a $(C_1-C_7)$alkoxycarbonyl;

$R_{16}$ and $R_{17}$ are each independently hydrogen; or a $(C_1-C_7)$alkyl;

or else $R_{16}$ and $R_{17}$, together with the nitrogen atom to which they are bonded, form a heterocycle selected from morpholine, thiomorpholine, azetidine, pyrrolidine, piperidine and piperazine, substituted in the 4-position by $R_{18}$, and perhydroazepine;

$R_{18}$ is a hydrogen; a $(C_1-C_7)$alkyl; a phenyl; a benzyl; a $(C_1-C_7)$alkylcarbonyl; a formyl; a benzoyl; a $(C_1-C_7)$alkoxycarbonyl; a phenoxycarbonyl; or a carbamoyl which is free or substituted by one or two $(C_1-C_7)$alkyls;

$R_{19}$ is hydrogen; or a $(C_1-C_8)$alkyl;

$R_{20}$ is a hydrogen; a $(C_1-C_8)$alkyl; a $(C_3-C_7)$cycloalkyl which is unsubstituted or substituted by a $(C_1-C_4)$alkyl; a group Ar; a pyridyl; a methylpyridyl; a piperid-4-yl substituted in the 1-position by $R_{18}$; a piperid-1-yl; a pyrrolidin-1-yl; a morpholin-4-yl; a thiazol-2-yl; an indanyl; an adamantyl; or a $(C_1-C_7)$alkyl substituted by one or more halogens or $R_{26}$;

or else $R_{19}$ and $R_{20}$, together with the nitrogen atom to which they are bonded, form a heterocyclic radical $R_{25}$;

$R_{21}$ and $R_{22}$ are each independently hydrogen; or a $(C_1-C_7)$alkyl;

or else $R_{21}$ and $R_{22}$, together with the nitrogen atom to which they are bonded, form a heterocyclic radical $R_{25}$;

$R_{25}$ is a morpholin-4-yl; a thiomorpholin-4-yl; an azetidin-1-yl which is unsubstituted or substituted in the 3-position by a group —$NR_{11}R_{27}$, a $(C_1-C_7)$alkyl, a phenyl, a benzyl or a $(C_1-C_7)$alkylcarbonyl; a perhydroazepin-1-yl; a piperazin-1-yl which is unsubstituted or substituted in the 4-position by a $(C_1-C_7)$alkyl, a phenyl, a benzyl, a $(C_1-C_7)$alkylcarbonyl, a $(C_1-C_7)$alkoxycarbonyl or a benzyloxycarbonyl; a piperid-1-yl which is unsubstituted or substituted in the 4-position by a $(C_1-C_7)$alkyl, a phenyl, a benzyl, a $(C_1-C_7)$alkylcarbonyl or a group —$NR_{11}R_{27}$; or a pyrrolidin-1-yl which is unsubstituted or substituted by a $(C_1-C_7)$alkyl, a phenyl, a benzyl, a $(C_1-C_7)$alkylcarbonyl, a hydroxymethyl, a carboxyl, a $(C_1-C_7)$alkoxycarbonyl or a carbamoyl which is unsubstituted or substituted by one or two $(C_1-C_7)$alkyls;

$R_{26}$ is a hydroxyl; a $(C_1-C_7)$alkoxy; a cyano; a carboxyl; a $(C_1-C_7)$alkoxycarbonyl; a benzyloxycarbonyl; a group —$NR_{11}R_{27}$; a carbamoyl which is free or substituted by one or two $(C_1-C_7)$alkyls; a pyrrolidin-1-ylcarbonyl; a piperid-1-ylcarbonyl; a perhydroazepin-1-ylcarbonyl; a group Ar; a $(C_3-C_7)$cycloalkyl; an adamantyl; or a heterocyclic radical selected from a pyridyl; a methylpyridyl; a furanyl; a tetrahydrofuranyl, a thienyl; a methylthienyl; a pyrrolidin-1-yl, a piperid-1-yl and a perhydroazepin-1-yl;

Ar is a phenyl which is unsubstituted or monosubstituted or polysubstituted by a substituent selected from the group consisting of a halogen atom, a $(C_1-C_7)$alkyl, a trifluoromethyl, a hydroxyl, a $(C_1-C_7)$alkoxy, a carboxyl, a $(C_1-C_7)$alkoxycarbonyl, a $(C_1-C_7)$alkylcarbonyloxy, a nitro, a cyano, an amino, a $(C_1-C_7)$alkylamino and a di$(C_1-C_7)$alkylamino, said substituents being identical or different;

t is an integer which may vary from 2 to 5;

u is an integer which may vary from 0 to 5; and m is 1-4, provided that when m is 2-4 each $R_6$ independently represents a halogen, a $(C_1-C_7)$alkyl or a $(C_1-C_7)$alkoxy.

8. A pharmaceutical composition containing effective amounts of two compounds of formula (I) or of pharmaceutically acceptable salts thereof, one being a specific $V_1$ receptor antagonist and the other being a specific oxytocin antagonist, in combination with suitable excipients:

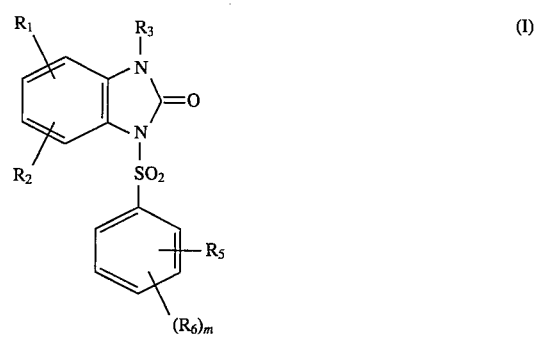

in which:

$R_1$ and $R_2$ are each independently a hydrogen; a halogen; a hydroxyl; an ω-halogeno$(C_1-C_7)$alkoxy; a $(C_1-C_7)$alkyl; a trifluoromethyl; a $(C_1-C_7)$alkoxy; a polyhalogeno$(C_1-C_7)$alkoxy; an ω-hydroxy$(C_2-C_7)$alkoxy; an ω-methoxy$(C_2-C_7)$alkoxy; an ω-amino$(C_2-C_7)$alkoxy in which the amino is free or substituted by one or two $(C_1-C_7)$alkyls; a $(C_3-C_7)$cycloalkoxy; a $(C_3-C_7)$cycloalkylmethoxy; a phenoxy; a benzyloxy; a $(C_1-C_7)$alkylthio; a phenylthio; a nitro; an amino which is free or substituted by one or two $(C_1-C_7)$alkyls; a cyano; a formyl; a $(C_1-C_7)$alkylcarbonyl; a benzoyl; a formyloxy; a $(C_1-C_7)$alkylcarbonyloxy; a benzoyloxy; a $(C_1-C_7)$alkylsulfonamido; a phenylsulfonamido; a benzylsulfonamido; a $(C_1-C_7)$alkylcarbonylamino; a $(C_1-C_7)$alkoxycarbonylamino; a ureido which is unsubstituted or substituted by a phenyl, a benzyl or one or two $(C_1-C_7)$alkyls; or a thioureido which is unsubstituted or substituted by a phenyl, a benzyl or one or two $(C_1-C_7)$alkyls;

$R_3$ is $R_4$; a $(C_1-C_8)$alkyl; a $(C_1-C_8)$alkylene substituted by $R_4$; a $(C_1-C_8)$alkylene substituted by a $(C_1-C_4)$alkoxy; an indanyl; a hexahydroindanyl; an adamantyl; a noradamantyl; a norbornyl; or a cyclohexyl substituted by a di$(C_1-C_7)$alkylamino, a carboxyl, a $(C_1-C_4)$alkoxycarbonyl, a hydroxyl, a tetrahydropyran-2-yloxy, a $(C_1-C_4)$alkoxy$(C_1-C_4)$alkoxy or a phenyl$(C_1-C_2)$alkoxy$(C_1-C_4)$alkoxy;

$R_4$ is a group —$NR_{16}R_{17}$; a $(C_3-C_7)$cycloalkyl which is unsubstituted or monosubstituted or disubstituted by a $(C_1-C_4)$alkyl or a $(C_1-C_4)$alkoxy; a group Ar; a furyl; a thienyl; a pyrrolyl; a triazolyl; a tetrazolyl; a pyridyl; a pyridyl N-oxide; a pyrimidinyl; a pyrazolyl; a pyrazinyl; a tetrahydropyran-4-yl; an azetidin-3-yl substituted in the 1-position by $R_{18}$; a piperid-4-yl substituted in the 1-position by $R_{18}$ or disubstituted in the 1-position by one or two $(C_1-C_7)$alkyls and/or one or two benzyls; a pyrrolidinyl; a perhydroazepinyl; or a morpholinyl;

$R_5$ and $R_6$ are each independently a hydrogen; a halogen; a $(C_1-C_7)$alkyl; a trifluoromethyl; a cyano; a nitro; a hydroxylamino; a carboxyl; a guanidino which is unsubstituted or substituted in the 1-position by a $(C_1-C_7)$alkyl and/or in the 3-position by one or two $(C_1-C_7)$alkyls, a phenyl or a benzyl and/or in the 2-position by a cyano; a group —$OR_7$; a group —$SR_7$; a $(C_1-C_7)$alkylcarbonyl; a formyl; a benzoyl; a $(C_1-C_7)$alkoxycarbonyl; a phenoxycarbonyl; a benzyloxycarbonyl; a group —$CONR_{19}R_{20}$; a group —$CSNR_{11}R_{27}$; a group —$SO_2$—$NR_{21}R_{22}$; a $(C_1-C_7)$alkylsulfonamido; a benzylsulfonamido; a group —$NHSO_2$-Ar; a group —$NR_8R_9$; a group —CO—NH—$CR_{10}R_{23}$—CO—$R_{12}$; or a group —$CH_2NR_8R_9$;

$R_7$ is a hydrogen; a $(C_1-C_7)$alkyl; a phenyl; a benzyl; a $(C_3-C_7)$cycloalkyl; a $(C_2-C_7)$alkenyl; an ω-halogeno$(C_2-C_7)$alkyl; a polyhalogeno$(C_1-C_7)$alkyl; an ω-hydroxy$(C_2-C_7)$alkyl; a $(C_1-C_7)$alkylcarbonyl; a formyl; a benzoyl; an ω-carboxy$(C_1-C_7)$alkyl; an ω-$(C_1-C_7)$alkoxy-carbonyl$(C_1-C_7)$alkyl; an ω-benzyloxycarbonyl$(C_1-C_7)$alkyl; an ω-amino$(C_2-C_7)$alkyl in which the amino group is free or substituted by one or two $(C_1-C_7)$alkyls, or in the form of an ammonium ion; or an ω-carbamoyl$(C_1-C_7)$alkyl in which the carbamoyl is free or substituted by one or two $(C_1-C_7)$alkyls;

$R_8$ is hydrogen; a $(C_1-C_7)$alkyl; or a group —$CH_2$—Ar;

$R_9$ is hydrogen; a $(C_1-C_7)$alkyl; a group —$CH_2$—Ar; a group Ar; a $(C_3-C_8)$alkenyl; a $(C_1-C_7)$alkylcarbonyl; a formyl; a $(C_1-C_7)$alkylthiocarbonyl; a $(C_3-C_7)$cycloalkylcarbonyl; a $(C_3-C_7)$cycloalkylthiocarbonyl; an ω-amino$(C_2-C_7)$alkylcarbonyl in which the amino is free or substituted by one or two $(C_1-C_7)$alkyls; an ω-hydroxy$(C_1-C_7)$alkylcarbonyl; an ω-benzyloxy$(C_1-C_7)$alkylcarbonyl; a pyridylcarbonyl; a methylpyridylcarbonyl; a thienylcarbonyl; a group —CO—Ar; a group —CO—$CH_2$—Ar; a $(C_1-C_7)$alkoxycarbonyl; a phenoxycarbonyl; a phenoxythiocarbonyl; a benzyloxycarbonyl; a group —CO—$CR_{R23}$—$NR_{11}R_{27}$; a group —$CR_{10}R_{23}COR_{12}$; a group —$(CH_2)_tCOR_{12}$; a group —$CO(CH_2)_uCOR_{12}$; a group —$CONR_{14}R_{24}$; a group —$CSNR_{14}R_{24}$; or a heterocyclic radical selected from pyrazolyl, imidazolyl, triazolyl, tetrazolyl, pyridyl, pyridazinyl, pyrimidinyl and thiazolyl;

or else $R_8$ and $R_9$, together with the nitrogen atom to which they are bonded, form hydantoin, N-methylhydantoin or a heterocyclic radical selected from morpholin-4-yl, pyrrol-1-yl, Δ3-pyrrolin-1-yl, pyrrolidin-1-yl and isoindolin-2-yl, in which the benzene ring is unsubstituted or substituted by a halogen, a $(C_1-C_7)$alkyl, a trifluoromethyl or a methoxy;

$R_{10}$ and $R_{23}$ are each independently hydrogen; a $(C_1-C_7)$alkyl; or a benzyl;

or else $R_{10}$ and $R_{23}$, together with the carbon atom to which they are bonded, form a $(C_3-C_7)$cycloalkyl;

$R_{11}$ and $R_{27}$ are each independently hydrogen; or a $(C_1-C_7)$alkyl;

$R_{12}$ is a hydroxyl; a $(C_1-C_7)$alkoxy; or an amino which is free or substituted by one or two $(C_1-C_7)$alkyls;

$R_{14}$ is hydrogen; or a $(C_1-C_7)$alkyl;

$R_{24}$ is hydrogen; a $(C_1-C_7)$alkyl; a $(C_1-C_7)$alkyl substituted by $R_{15}$; a group Ar; a $(C_3-C_7)$cycloalkyl; or an adamantyl;

or $R_{14}$ and $R_{24}$, together with the nitrogen atom to which they are bonded, form a heterocycle selected from morpholine, thiomorpholine, piperazine, azetidine, pyrrolidine, piperidine and perhydroazepine, said heterocycle being unsubstituted or substituted by one or more methyl groups, a phenyl or an amino group which is free or carries a protecting group;

$R_{15}$ is a group Ar; a pyridyl; a hydroxyl; a $(C_1-C_7)$alkoxy; a group —$NR_{11}R_{27}$; a carboxyl; or a $(C_1-C_7)$alkoxycarbonyl;

$R_{16}$ and $R_{17}$ are each independently hydrogen; or a $(C_1-C_7)$alkyl;

or else $R_{16}$ and $R_{17}$, together with the nitrogen atom to which they are bonded, form a heterocycle selected from morpholine, thiomorpholine, azetidine, pyrrolidine, piperidine and piperazine, substituted in the 4-position by $R_{18}$, and perhydroazepine;

$R_{18}$ is a hydrogen; a $(C_1-C_7)$alkyl; a phenyl; a benzyl; a $(C_1-C_7)$alkylcarbonyl; a formyl; a benzoyl; a $(C_1-C_7)$alkoxycarbonyl; a phenoxycarbonyl; or a carbamoyl which is free or substituted by one or two $(C_1-C_7)$alkyls;

$R_{19}$ is hydrogen; or a $(C_1-C_8)$alkyl;

$R_{20}$ is a hydrogen; a $(C_1-C_8)$alkyl; a $(C_3-C_7)$cycloalkyl which is unsubstituted or substituted by a $(C_1-C_4)$alkyl; a group Ar; a pyridyl; a methylpyridyl; a piperid-4-yl substituted in the 1-position by $R_{18}$; a piperid-1-yl; a pyrrolidin-1-yl; a morpholin-4-yl; a thiazol-2-yl; an indanyl; an adamantyl; or a $(C_1-C_7)$alkyl substituted by one or more halogens or $R_{26}$;

or else $R_{19}$ and $R_{20}$, together with the nitrogen atom to which they are bonded, form a heterocyclic radical $R_{21}$ and $R_{22}$ are each independently hydrogen; or a $(C_1-C_7)$alkyl;

or else $R_{21}$ and $R_{22}$, together with the nitrogen atom to which they are bonded, form a heterocyclic radical $R_{25}$;

$R_{25}$ is a morpholin-4-yl; a thiomorpholin-4-yl; an azetidin-1-yl which is unsubstituted or substituted in the 3-position by a group —$NR_{11}R_{27}$, a $(C_1-C_7)$alkyl, a phenyl, a benzyl or a $(C_1-C_7)$alkylcarbonyl; a perhydroazepin-1-yl; a piperazin-1-yl which is unsubstituted or substituted in the 4-position by a $(C_1-C_7)$alkyl, a phenyl, a benzyl, a $(C_1-C_7)$alkylcarbonyl, a $(C_1-C_7)$alkoxycarbonyl or a benzyloxycarbonyl; a piperid-1-yl which is unsubstituted or substituted in the 4-position by a $(C_1-C_7)$alkyl, a phenyl, a benzyl, a $(C_1-C_7)$alkylcarbonyl or a group —$NR_{11}R_{27}$; or a pyrrolidin-1-yl which is unsubstituted or substituted by a $(C_1-C_7)$alkyl, a phenyl, a benzyl, a ($C_1$–$C_7$)alkylcarbonyl, a hydroxymethyl, a carboxyl, a ($C_1$–$C_7$)alkoxycarbonyl or a carbamoyl which is unsubstituted or substituted by one or two ($C_1$–$C_7$)alkyls;

$R_{26}$ is a hydroxyl; a ($C_1$–$C_7$)alkoxy; a cyano; a carboxyl; a ($C_1$–$C_7$)alkoxycarbonyl; a benzyloxycarbonyl; a group —$NR_{11}R_{27}$; a carbamoyl which is free or substituted by one or two ($C_1$–$C_7$)alkyls; a pyrrolidin-1-ylcarbonyl; a piperid-1-ylcarbonyl; a perhydroazepin-1-ylcarbonyl; a group Ar; a ($C_3$–$C_7$)cycloalkyl; an adamantyl; or a heterocyclic radical selected from a pyridyl; a methylpyridyl; a furanyl; a tetrahydrofuranyl, a thienyl; a methylthienyl; a pyrrolidin-1-yl, a piperid-1-yl and a perhydroazepin-1-yl;

Ar is a phenyl which is unsubstituted or monosubstituted or polysubstituted by a substituent selected from the group consisting of a halogen atom, a ($C_1$–$C_7$)alkyl, a trifluoromethyl, a hydroxyl, a ($C_1$–$C_7$)alkoxy, a carboxyl, a ($C_1$–$C_7$)alkoxycarbonyl, a ($C_1$–$C_7$)alkylcarbonyloxy, a nitro, a cyano, an amino, a ($C_1$–$C_7$)alkylamino and a di($C_1$–$C_7$)alkylamino, said substituents being identical or different;

t is an integer which may vary from 2 to 5;

u is an integer which may vary from 0 to 5; and m is 1-4, provided that when m is 2-4 each $R_6$ independently represents a halogen, a ($C_1$–$C_7$)alkyl or a $C_1$–$C_7$)alkoxy.

9. A pharmaceutical composition containing an effective amount of a compound according to claim 2 or a pharmaceutically acceptable salt thereof, in combination with suitable excipients.

10. A pharmaceutical composition containing an effective amount of a compound according to claim 3 or a pharmaceutically acceptable salt thereof, in combination with suitable excipients.

11. A pharmaceutical composition containing an effective amount of a compound according to claim 4 or a pharmaceutically acceptable salt thereof, in combination with suitable excipients.

12. A pharmaceutical composition containing (i) an effective amount of a compound according to claim 2 or a pharmaceutically acceptable salt thereof; (ii) an effective amount of a compound selected from the group consisting of a converting enzyme inhibitor, an angiotensin II antagonist, a renin inhibitor, a peripheral vasodilator, a calcium inhibitor, a beta-blocking agent, an α-1-blocking agent and a diuretic; and (iii) suitable excipients.

13. A pharmaceutical composition containing (i) an effective amount of a compound according to claim 3 or a pharmaceutically acceptable salt thereof; (ii) an effective amount of a compound selected from the group consisting of a converting enzyme inhibitor, an angiotensin II antagonist, a renin inhibitor, a peripheral vasodilator, a calcium inhibitor, a beta-blocking agent, an α-1-blocking agent and a diuretic; and (iii) suitable excipients.

14. A pharmaceutical composition containing (i) an effective amount of a compound according to claim 4 or a pharmaceutically acceptable salt thereof; (ii) an effective amount of a compound selected from the group consisting of a converting enzyme inhibitor, an angiotensin II antagonist, a renin inhibitor, a peripheral vasodilator, a calcium inhibitor, a beta-blocking agent, an α-1-blocking agent and a diuretic; and (iii) suitable excipients.

* * * * *